United States Patent [19]
Byers et al.

[11] Patent Number: 5,512,283
[45] Date of Patent: Apr. 30, 1996

[54] METHODS FOR THE SELECTIVE SUPPRESSION OF AN IMMUNE RESPONSE TO DUST MITE DER PI

[75] Inventors: Vera S. Byers, San Francisco, Calif.; Robert W. Baldwin, Long Eaton, England

[73] Assignee: Allergene, Inc., San Mateo, Calif.

[21] Appl. No.: 123,746

[22] Filed: Sep. 16, 1993

Related U.S. Application Data

[63] Continuation-in-part of PCT/US93/02082, Mar. 10, 1993, continuation-in-part of Ser. No. 11,050, Jan. 29, 1993, abandoned, and Ser. No. 849,222, Mar. 10, 1992, abandoned, which is a continuation-in-part of Ser. No. 549,184, Jul. 6, 1990, abandoned.

[51] Int. Cl.$^6$ .................. A61K 35/16; A61K 39/00; A61K 39/395; A61K 16/00

[52] U.S. Cl. .................. 424/171.1; 424/130.1; 424/278.1; 530/388.22; 530/388.75; 530/389.7; 530/868

[58] Field of Search .................. 530/388.22, 388.75, 530/389.7, 868; 424/130.1, 171.1, 278.1

[56] References Cited

U.S. PATENT DOCUMENTS

| | | |
|---|---|---|
| 4,740,371 | 4/1988 | Saint-Remy et al. . |
| 5,026,545 | 6/1991 | Saint-Remy et al. . |
| 5,286,628 | 2/1994 | Akagawa et al. . |

FOREIGN PATENT DOCUMENTS

| | | |
|---|---|---|
| 0287361A3 | 10/1988 | European Pat. Off. . |
| 0498124A1 | 8/1992 | European Pat. Off. . |
| WO84/02848 | 8/1984 | WIPO . |

OTHER PUBLICATIONS

Waldmann [Science 252:1657–1662 (1991)].
Harris et al. ITIBTECH 11:42–44 (1993)].
Osband et al. [Immunotherapy 11(6):193–195 (1990)].
Dillman [Ann. Internal Med. 111:592–600 (1989)].
Hird et al. [Genes and Cancer (1990) chapter 17].
Eddy et al. [J. Immunology 138:1693–1698 (1987)].
Jerne [Ann. Immunol. 125:373–389 (1974)].
Lombardero et al. [J. Immunology 144:1353–1360 (1990)].
Mascola et al., 1994, AIDS Vaccines: are we ready for human efficacy trials? JAMA 272(6):488–489.
Hoyne et al., 1993, Comparison of antigen presentation by lymph node cells from protein and peptide–primted mice. Immunology 78(1):58–64.
Le Mao et al., 1992, Identification of allergenic epitopes on Der f I, a major allergen of *Dermatophagoides* farinae, using monoclonal antibodies. Mol Immunol 29(2):205–211.
Abramowicz et al., 1992 New Eng J Med p736.
Didierlaurent et al., 1991, Measurement of IgE specific to a major allergen of house dust mite: Der p I. J Immunol Methods 145(1–2):33–41.
Austin et al., 1991, Induction of delayed hypersensitivity to human tumor cells with a human monoclonal anti–idiotypic antibody. J Natl Cancer Inst 83(17):1245–8.
Machiels et al., 1990, Allergic bronchial asthma due to *Dermatophagoides pteronyssinus* hypersensitivity can be efficiently treated by inoculation of allergen–antibody complexes. J Clin Invest 85:1024–1035.
Kurata et al., 1990, J Immunol 144:4526.
Morikawa et al., 1990, B–Cell mediated regulation of delayed–type hypersensitivity. Cellular Immunol 131:338–351.
Baskar et al., 1990, "The presentation of L–tyrosine–azobenzenearsonate by different mouse Ia molecules uses a common agretope," Mol Immunol 27:79–86.
Konishi and Uehara, 1990, Enzyme–linked immunosorbent assay for quantifying antigens of *Dermatophagoides* farinae and *D. pteronyssinus* (Acari: Pyroglyphidae) in house dust samples. J Med Entomol 27(6):993–998.
Luczynska et al., 1989, A two–site monoclonal antibody ELISA for the quantification of the major *Dermatophagoides* spp. allergens, Der p I and Der f I. J Immunol Methods 118(2):227–235.
Rajnavolgyi et al., 1989, "Structural characteristics influencing the carrier function of synthetic branched polypeptides based on poly[Lys–(DL–Ala)3] backbone," Mol Immunol 26:949–958.
Bigby et al., 1989, "Production of hapten–specific T cell hybridomas and their use to study the effect of ultraviolet B irradiation on the development of contact hypersensitivity," J Immunol 143:3867–3872.
Heymann et al., 1989, Antigenic and structural analysis of group II allergens (Der f I and Der p II) from house dust mites (Dermatophagoides spp). J Allergy Clin Immunol 83(6):1055–1067.
Riechmann et al., 1988, Nature 332:323–327.
Owhashi et al., 1988, Protection from experimental allergic encephalomyelitis conferred by a monoclonal antibody directed against a shared idiotype on rat T cell receptors specific for myelin basic protein, J Exp Med 168:2153–2164.

(List continued on next page.)

*Primary Examiner*—Donald E. Adams
*Attorney, Agent, or Firm*—Pennie & Edmonds

[57] ABSTRACT

The present invention provides novel compositions and methods useful in the modulation or selective suppression of host immune responses to an immunogen of interest, particularly to immunogens which are exogenous antigens or allergens. Subject compositions include antibody, antibody derived, and antibody-like molecules of primary antigen reactivity with respect to the immunogen of interest. Antibodies or antibody-like or antibody-derived molecules include antibody fragments such as Fab, and complementarity determining region peptides (CDRs) which may be grafted into a framework region of any species, particularly human. They also include human antibodies, derived from sensitized human lymphocytes produced by cell fusion with heterohybridomas, or by DNA cloning and expression. Other compositions include T cell receptor (TCR) molecules, obtained either from T cell clones or hybridomas or as purified TCR preparations. Immunoreactive peptides corresponding to some or all of the complementarity determining regions or hypervariable regions of the TCR are also employed.

10 Claims, 28 Drawing Sheets

OTHER PUBLICATIONS

Sikorska et al., 1988, J Biol Resp Med 7:327–358.

Kalish et al., 1988, Urushiol (poison ivy)–triggered suppressor T cell clone generated from peripheral blood. J Clin Invest 82:825–832.

Thompson et al., 1988, "IgE antibodies to *D. pteronyssinus* in atropic patients," Immunology 64:311–314.

Kappler et al., 1988, "Self–tolerance eliminates T cells specific for Mis–modified products of the major histocompatibility complex," Nature 332:35–40.

Lind et al., 1988, The binding of mouse hybridoma and human IgE antibodies to the major fecal allergen, Der p I, of *Dermatophagoides pteronyssinus*. Relative binding site location and species specificity studied by solid–phase inhibition assays with radiolabelled antigen. J Immunol 140(12):4256–4262.

van der Zee et al., 1988, Skin tests and histamine release with P1–depleted *Dermatophagoides pteronyssinus* body extracts and purified P1. J Allergy Clin Immunol 81 (5 Pt 1):884–896.

Buus et al., 1987, "The interaction between protein–derived immunogenic peptides and Ia," Immunol Rev (Denmark) 98:115–141.

Chapman et al., 1987, Epitope mapping of two major inhalant allergens, Der p I and Der f I, from mites of the genus *Dermatophagoides*. J Immunol 139:1479–1484.

Chapman et al., 1987, "Monoclonal immunoassays for major dust mite (Dermatophagoides) allergens, Der p I and Der f I, and quantitative analysis of the allergen content of mite and house dust extracts," J Allergy Clin Immunol 80(2):184–194.

Dunn et al., 1987, Regulation of murine contact sensitivity to urushiol components by serum factors. J Invest Dermatol 89:296–298.

Horn and Lind, 1987, Selection and characterization of monoclonal antibodies against a major allergen in *Dermatophagoides pteronyssinus*. Species–specific and common epitopes in three Dermatophagoides species. In Arch Allergy Appl Immunol 83(4):404–409.

Thomas et al., 1987, "Production of monoclonal antibodies selective for aggregation–competent chick neural retina cells. An immunosuppressive approach," J Immunol Methods (Netherlands) 97:237–243.

Norton and Benjamini, 1987, "Studies on the suppression of the immune response to a defined protein epitope by anti––idiotypic antibodies," Cellular Immunol 109:419–428.

Platts–Mills and Chapman, 1987, J Allergy Clin Immunol 80:755–775.

Heymann et al., 1986, Antigen Der f I from the dust mite *Dermatophagoides* farinae: structural comparison with Der p I from *Dermatophagoides pteronyssinus* and epitope specificity of murine IgG and human IgE antibodies. J Immunol 137(9):2841–2847.

Ley et al., 1986, Isolation and characterization of the main allergen of *Dermatophagoides* farinae by monoclonal antibodies that recognize IgE related epitopes. Mol Immunol 23(12):1311–1318.

Machtinger et al., 1986, Cow's milk allergy in breast–fed infants: the role of allergen and maternal secretory IgA antibody. J Allergy Clin Immunol 77:341–347.

Wetterwald et al., 1986, "Suppression of the established IgE antibody responses with isologous anti–idiotypic antibodies in guinea pigs," 23(3):347–356.

Chapman et al., 1985, Recognition of species–specific and cross–reacting antigenic determinants on house dust mite (Dermatophagoides) allergens using monoclonal antibodies. Int Arch Allergy Appl Immunol 77(1–2):166–168.

Ley et al., 1985, Identification of a novel allergen molecule from *Dermatophagoides* by monoclonal antibodies. Immunol Lett 11(2):89–93.

Chapman, et al., 1984, Recognition of two *dermatophagoides* pteronyssinus–specific epitopes on antigen P1 by using monoclonal antibodies: binding to each epitope can be inhibited by serum from dust mite–allergic patients. J Immunol 133(5):2488–2495.

Paul et al., 1984 p229.

Dunn et al., 1982, "A murine model system for contact sensitization to poison oak or ivy urushiol components," Cellular Immunol 68:377–388.

Epstein et al., 1982, "Induction of antigen specific hyposensitization to poison oak in sensitized adults," Arch Dermatol 118:630–633.

Infante et al., 1982, "Definition of T cell idiotypes using anti–idiotypic antisera produced by Immunization with T cell clones," J Exp Med 155:1100–1107.

Krilis et al., 1981, "Standardization of allergens: lectins and monoclonal antibodies as primary standards for house dust mite allergens," Int Archs Allergy appl Immun 66(Suppl. 1):252–258.

Epstein et al., 1981, "Induction of persistent tolerance to urushiol in humans," J Allergy Clin Immunol 68:20–25.

Liberato et al., 1981, J Med Chem 24:28–33.

Claman et al., 1980, "Suppressive mechanisms involving sensitization and tolerance in contact allergy," Immunol Rev (Denmark) 50:105–132.

Stockinger et al., 1979, On the feedback regulation of humoral immune response. I. Evidence for "B Suppressor Cells". Immunology 36:87–94.

Klaus et al., 1978, Antigen antibody complexes elicit anti––idiotypic antibodies to self–idiotopes. Nature 272:265–266.

Jerne et al., 1974, Towards a network theory of the immune system. Ann Immunol 125:373–389.

McConnell, 1971, "Studies on actively allergized cells. III. Suppression of the allergic response with specific antibody and the effect of this treatment on plaque– and rosette–forming cells," International Archives if Allergy 40:287–304.

Baer et al., 1970, "The immunochemistry if immune tolerance. II. The relationship of chemical structure to the induction of immune tolerance to catechols," J Immunol 104:178–184.

Chang et al., 1969, Study of the mechanism of the suppression of active antibody synthesis by passively administered antibody. J Immunol 102:37–41.

Baer et al., 1967, "Delayed contact hypersensitivity to catechols. II. Cutaneous toxicity of catechols chemically related to the active principles of poison ivy," J Immunol 99:365–369.

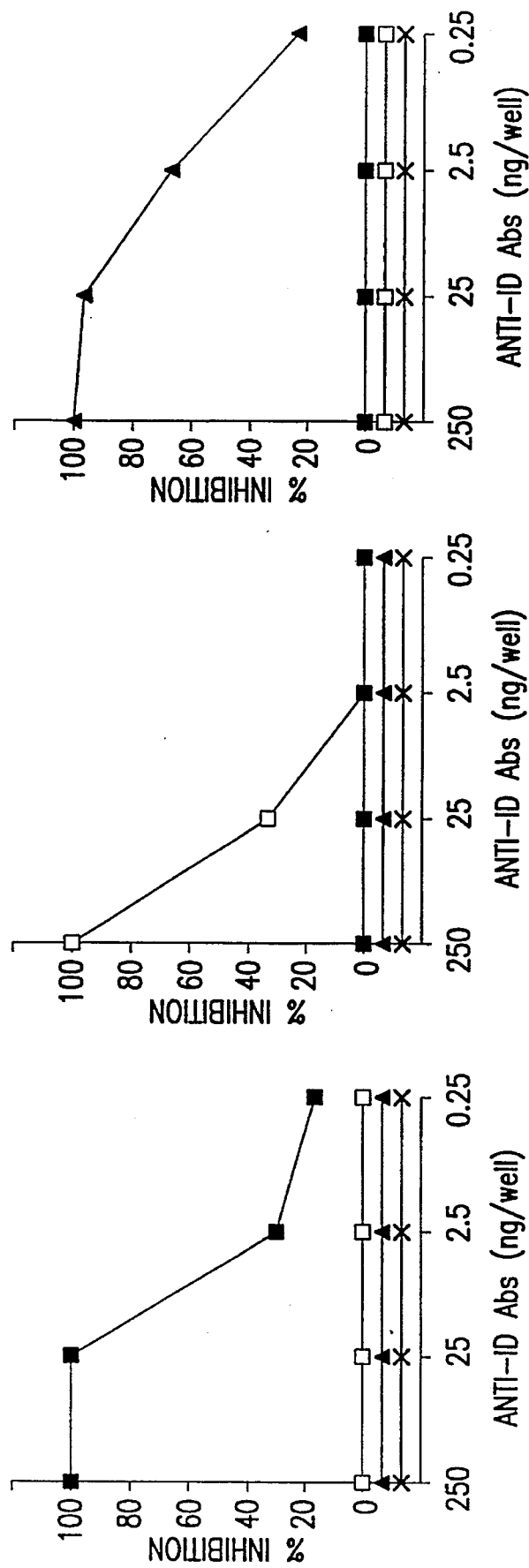

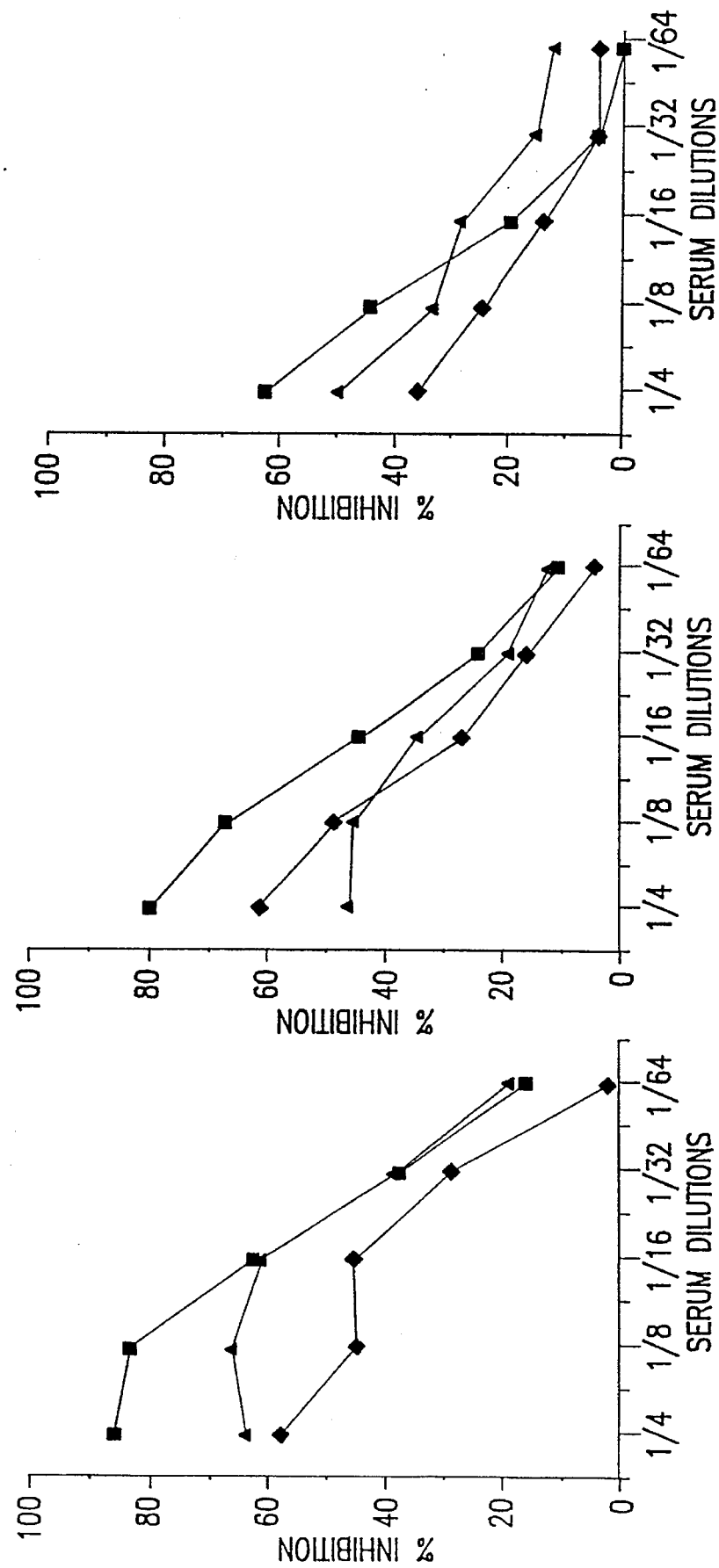

METHODS FOR THE SELECTIVE SUPPRESSION OF AN IMMUNE RESPONSE TO DUST MITE DER PI

This application is a continuation-in-part of U.S. applications Ser. No. PCT/US/02082 filed Mar. 10, 1993, abandoned, U.S. Ser. No. 08/011,050 filed Jan. 29, 1993, abandoned, U.S. Ser. No. 07/849,222 filed Mar. 10, 1992, abandoned, the latter being a continuation-in-part of U.S. Ser. No. 07/549,184 filed Jul. 6, 1990 abandoned, which are hereby incorporated by reference.

TABLE OF CONTENTS

1. Field of the invention
2. Background of the invention
   2.1 Allergic diseases
      2.1.1 IgE mediated diseases: Asthma, allergic rhinitis and atopic dermatitis
      2.1.2 Dust mite allergens
      2.1.3 Rye grass allergens
      2.1.4 TC mediated allergic skin disease: Poison oak and ivy dermatitis
   2.2 IgG mediated response to protein antigens: RTA
   2.3 Immunology of allergic diseases
   2.4 Immunotherapy with allergens
      2.4.1 Immunotherapy with anti-idiotypic antibodies (Ab 2)
      2.4.2 Immunotherapy with Ab1 antibodies
3. Brief description of the figures
4. Summary of the invention
5. Detailed description of the invention
   5.1 Production of monoclonal antibodies
   5.2 Production of humanized monoclonal antibodies
   5.3 Chimerization-humanization of murine monoclonal antibodies
   5.4 Selection of Ab1s
      5.4.1 Demonstration that the selected monoclonal antibody recognizes a human IgE immunodominant protein in the allergen mixture in those cases in which the allergen is a mixture rather than a single component
      5.4.2 Demonstration that the selected monoclonal antibody recognizes a human IgE immunodominant epitope on the protein
      5.4.3 Demonstration that the selected monoclonal antibody stimulates an anti-idiotype specificity similar to that induced in humans, including those receiving allergen specific immunotherapy
      5.4.4 Demonstration that treatment of animals with the Mab significantly down-regulates the immune response against the allergen
6. Example: Ab1s to dust mite allergens
   6.1 Dust mite allergens
   6.2 Dust mite preparations
      6.2.1 Purified Group I Mite Allergens
      6.2.2 Purification of Group II Mite Allergens
   6.3 Production of murine anti Der p and anti Der f monoclonal antibodies
      6.3.1 Immunization protocol
      6.3.2 Hybridoma selection protocol
      6.3.3 Anti-idiotypic antibody response to murine anti-Der p and anti-Der f monoclonal antibodies
   6.4 Murine anti-Der p hybridoma cell lines
      6.4.1 Mab 1102/H11
      6.4.2 Mab 1107/2B11
      6.4.3 Other murine anti-dust mite Mab
   6.5 Selection of murine anti-Der p Mab for down-regulating immune responses to Der p I and Der p II allergens
      6.5.1 Anti Der p I Mab 2C7
      6.5.2 Mab idiotype characterization
      6.5.3 Relationship between Der p I epitopes inducing human IgE antibodies and those reacting with murine Anti-Der p I Mabs
      6.5.4 Identification of idiotypes of Mab 2C7 and Human anti-Der p I IgE Antibody
   6.6 Chimerization-humanization of murine monoclonal antibodies
   6.7 CDR grafting
7. Example: production of human anti-Der p monoclonal antibodies
   7.1 Hybridoma Production
      7.1.1 Fusion Protocol
      7.1.2 Lymphocyte Preparation
      7.1.3 In vitro stimulation
   7.2 Hybridoma Selection
   7.3 Epstein-Barr Virus Transformation
   7.4 Repertoire Cloning
   7.5 Results
      7.5.1 DM27 1E11
      7.5.2 Other human anti-dust mite Mab
      7.5.3 In Vivo Testing of Anti-Der p Mab for Down-Regulating T Lymphocyte Mediated Responses to Dust Mite Allergens
8. Inhibition of Delayed Type Hypersensitivity (DTH) Responses in Mice to Dust Mite Allergens
   8.1 Induction of DTH in Mice to Dust Mite Extracts
   8.2 Suppression of Der p I induced DTH Response in Mice Treated with Anti-Der p Mab
   8.3 Decrease in T cell reactivity by in vitro parameters
   8.4 Assessment of down regulation of IgE anti-DMA response
      8.4.1 SCID mouse model
      8.4.2 Normal mouse model
      8.4.3 Aerosol-sensitized mouse model
9. Example: Inhibition of Allergic Response to Dust Mite Allergens
   9.1 Development of an IgE Dust Mite Murine Model to Detect Serum IgE Responses
      9.1.1 Sensitization with Aerosolized Dust Mite Allergen
   9.2 Immune Response Against Der p I
      9.2.1 Passive Cutaneous Anaphylaxis (PCA)
   9.3 Suppression of Anti-Der p I IgE Responses
      9.3.1 Passive Cutaneous Anaphylaxis Assay
      9.3.2 Determination of Murine Serum Anti-Der p I IgE Antibody Levels
      9.3.3 ELISA Assay Anti-Der p I IgE Antibody
      9.3.4 Results
10. Example: Use of anti-urushiol monoclonal antibodies (AB1) to down regulate the T cell response to poison oak and ivy allergy
    10.1 Preparation of 3-n-Alkylcatechol Conjugates for Use as Immunogens
       10.1.1 Reaction of auto-oxidized urushiol to proteins
       10.1.2 Conjugation of Alkylcatechol to Protein through its n Acetyl Cysteine Intermediate to Common Protein Carriers
       10.1.3 Conjugation of 3-n-pentadecylcatechol (PDC) to Polyaspartic Acid 10.2 Production of Anti-Urushiol Monoclonal Antibodies and TCR's.

10.3 Immunoreactivity of Mab 991

10.4 Down-regulation of Delayed Type Hypersensitivity Responses to Urushiol 10.5 Anti-urushiol antibodies 10.5.1 Production by simple immunization with urushiol-carrier with or without adjuvant 10.5.2 Production of anti-urushiol responses using additional immune manipulation 10.5.3 Use of urushiol alone as B cell immunogen 10.5.4 Use of lymphocytes from sensitized humans 10.6 Production of Anti-Urushiol Monoclonal Antibody ($Ab_1$)

10.6.1 Murine monoclonal antibodies 10.6.2 Production of human monoclonal antibodies 10.6.2.1 From murine monoclonal antibodies 10.7 Production of Anti-Urushiol T Cell Receptors For Use As Immunogens 10.7.1 Production of urushiol specific T cell l Poison oak and ivy dermatitis is one example of a direct T cell mediated allergic reaction. This reaction occurs against the hapten urushiol when it contacts the skin, bronchial epithelium or the like. The hapten is a mixture of 3-n-alkylcatechols found in the oil of the plant, which conjugates to body proteins. The conjugate stimulates T cells to directly attack the skin or other cells to which the hapten is bound.

T cell etiology of the disease has been confirmed by studies in animal models of poison oak dermatitis which include the guinea pig and mouse. Transfer studies in animals have demonstrated the allergic reaction can be transferred from sensitized to naive animals by T lymphocytes. Human and animal studies have identified the specificity of the T cell reaction against the allergen. Both the specificity and antigenicity of the compounds reside primarily in the common catechol structure. The immunologic reactions seen with urushiol are typical of those caused by various identified contact sensitizers, such as chlorinated hydrocarbons and epoxy resins.

In humans, oral hyposensitization is quite effective although cumbersome since it requires 3–6 months of daily administration of the oil. Although antibodies against urushiol have never been directly demonstrated, the antibody fraction of sera from desensitized patients will transfer tolerance to mice, suggesting a role for regulatory antibodies.

2.2 IgG mediated response to protein antigens: RTA

There are other cases in which undesirable immune responses occur to protein antigens, such as ricin A chain (RTA) a protein which, when coupled to a targeting agent such as a lymphokine or monoclonal antibody such as Mab 791T/36 (immunotoxin), directed against colorectal cancer, can kill the targeted cell. RTA is a very potent immunogen, and a single injection of immunotoxin in animals or humans produces a vigorous IgG immune response against all parts of the molecule.

2.3 Immunology of allergic diseases

T lymphocytes, predominantly the CD4+ subset (Th2), play a central role in the initiation and maintenance of aero-allergen-mediated immune responses (Peltz, 1991; O'Hehir et al., 1991; Romagnani, 1992). Following exposure of susceptible subjects, T lymphocytes collaborate with B lymphocytes in producing cytokines. These interact with T and B cells, as well as other cells of the immune network such as macrophages. The lymphokines stimulate the enhanced production of helper T cells and B cells. Helper T cells further differentiate into two distinct subsets (Th1 and Th2) with characteristic lymphokine profiles. Th2 cells produce interleukin 4 (IL4), which is one signal required for IgE antibody synthesis. A second signal for IgE synthesis is produced following cognate T-B cell interactions involving recognition of T cell receptor/CD3 complex and major histocompatibility complex class II molecules (Romagnoni, 1990; Geha, 1992).

In addition to their role in IgE production, Th2 lymphocytes produce other lymphokines, particularly interleukin 5 (IL5), which are required for eosinophil recruitment and for initiating eosinophil mediated toxic responses (Clutterbuck et al., 1988, *Blood* 73:1504; Lopez et al., 1988, *J. Exp. Med.* 167:219). Il5 also-promotes most cell degranulation with release of cytokines, basic granule proteins, and platelet-activating factor. The T lymphocyte is critical for both immediate and late phase reactions, but is more directly involved in the late phase. This is demonstrated by the fact that steroids are active in preventing the late phase, but not the immediate phase reaction.

This overall pattern of immune responses to allergens implicates T cells as pivotal in the generation of immunoglobulin E and eosinophilia, two major components of an allergic response to aero-allergens (O'Hehir et al., 1991, *Ann. Rev. Immunol.* 9:67–95). Control of T cell responses to allergens through intervention at any of several points in the immune pathway therefore constitutes a major approach to treating allergic diseases. This is illustrated by the results from treatment of severe chronic asthmatics with cyclosporin A. Cyclosporin A is a potent immunosuppressive agent which acts principally on T lymphocytes. Patients treated with cyclosporin A showed a clinically significant improvement in their asthma symptoms.

2.4 Immunotherapy with allergens

Immunotherapy of allergic diseases including asthma, allergic rhinitis, as well as urushiol dermatitis has been undertaken for many years using hyposensitization with crude allergen extracts. This form of immunotherapy is effective in many patients and can provide lasting benefit even after immunotherapy has been discontinued (Busse, 1988, *J. All. Clin. Immunol.* 82:890–900). Immunotherapy with grass extracts has proven useful in treating allergic rhinitis and asthma (Creticos and Norman, 1987, *JAMA* 258:2874–2880; Creticos, 1989, *J. All. Clin. Immunol.* 83:554–562; Reid et al., 1986, *J. All. Clin. Immunol.* 78:590–600). In like fashion, patients with severe asthma achieved significant improvement following treatment with DMA-antibody complex (Machiels et al., 1990, *J. Clin. Invest.* 85:1024–1035), also clinical improvement and decreased bronchial sensitivity on bronchial provocation in children immunized for three years with a house dust extract (Creticos and Norman, 1987, *JAMA* 258:2874–2880, Creticos, 1990, *J. All. Clin. Immunol.* 83:554–562; Bousquet et al., 1985, *J. All. Clin. Immunol.* 76:734–744), and in patients with allergic rhinitis desensitized with either purified AgE from ragweed, or with the whole extract (Norman et al., 1968, *J. All.* 42:93–108). Similarly, with poison oak/ivy urushiol, oral hyposensitization is quite effective although cumbersome since it requires 3–6 months of daily administration of the oil. Indirect evidence for a regulatory role for anti-idiotypic antibodies and/or regulatory T cells is provided by several experimental and clinical studies. Subjects hyposensitized with urushiol generate immunoglobulins which can transfer tolerance to mice (Stampf et al., 1990, *J. Invest Derm.*). However, there are numerous difficulties with this form of treatment. Allergen extracts are crude, so that treatment schedules are not able to be standardized. Also, prolonged courses of treatment result in low patient compliance. Since the precise immune mechanism activated by hyposensitization with allergic extracts is not known, the cause of therapeutic failures usually cannot be established.

Several mechanisms may be postulated whereby immunoregulation of T cell dependent allergic responses can be achieved. One mechanism is to interfere with antigen processing and presentation to the T cell. Another is to tolerize the T cell, either directly or by production of T suppressor cells. This process will block either cognate T-B cell interactions or production of cytokines.

Indirect evidence for a regulatory role for anti-idiotypic antibodies and/or regulatory T cells is provided by several experimental and clinical studies. Subjects hyposensitized with urushiol generate immunoglobulins which can transfer tolerance to mice (Byers et al., 1990). In immediate type hypersensitivity, a general finding during hyposensitization is an initial increase in IgE antibodies, followed by a decrease. Concomitantly, there is an increase in the allergen specific IgG (Creticos, PS, *JAMA* 268:2834–2839). When the specificity of the response is investigated carefully, it is found that auto-anti-idiotypic antibodies develop (Gurka et al., 1988, *Ann. Allergy* 61:239–243). This has been shown to be the case in rye grass hyposensitization as well. Clinically, anti-idiotypic antibodies are elevated in human subjects following hyposensitization with rye grass extracts concomitant with reduction in allergic rhinitis (Hebert et al., 1990, *Clin. Exp. Immunol.* 80:413–419).

2.4.1 Immunotherapy with anti-idiotypic antibodies (Ab 2)

While transfer of anti-idiotypic antibodies results in suppression of both T and B lymphocyte initiated response, immunotherapy with monoclonal or polyclonal anti-idiotypic antibodies has not been successfully developed for allergic diseases, since the responses in experimental systems have been contradictory. In one example, treatment of mice with polyclonal anti-idiotypic antibodies generated against a mouse monoclonal antibody reacting with a tobacco mosaic virus protein polypeptide suppressed the ability of mice to generate antibody responses to the decapeptide (Norton and Benjamini, 1987, *Cell Immunol.* 109:418–419). In another example, polyclonal anti-idiotypic antibodies produced by immunization of guinea pigs with polyclonal anti-benzylpenicilloyl antibody were shown to down regulate the anti-benzyl penicillin IgE antibody responses when given either pre or post sensitization (Wetterwald et al., 1986, *Mol. Immunol.* 23:347–356). Also, polyclonal anti-idiotypic antibodies to a monoclonal antibody which reacted with a decapeptide of tobacco mosaic virus suppressed the induction of antibodies (the class is unknown) to this decapeptide in mice, when administered prior to sensitization (Norton and Benjamini, 1987). Clinically, transfer of serum from bee keepers who had tolerated multiple bee stings into individuals who previously developed anaphylaxis to desensitization allowed the receipts to undergo successful desensitization (Bousquet, 1987, *J. All. Clin. Immunol.* 79:947–954), and it is shown that the transferred whole sera contained anti-idiotypic antibodies against bee venom (Boutin et al., 1993, *J. All. Clin. Immunol.* in press). This has been explained by transfer of Ab2s which down regulated the response. Recently it has been confirmed that in one patient successfully treated in this way, the transferred whole sera did contain anti-idiotypic antibodies against bee venom. A decrease in skin test reactivity also was observed after transfer (Hebert, 1991).

In general, however, treatment with monoclonal Ab2 antibodies has been undertaken to up-regulate responses to specific antigens. These include cancer and viral antigens (Fung et al., 1990, *J. Immunol.* 145:2199–2206; Raychaudhuri et al., 1990, *J. Immunol.* 145:760–767, reviewed in Kohler et al., 1989, *Clin. Immunol. and Immunopath.* 52:104–116). Several of these are in clinical trials, for example against cancer antigens (Robins et al., 1991, *Can. Res.* 51:5425–5429). Consistent with these findings, vaccination with a monoclonal Ab2 directed against Lol p I allergen produced up-regulation of the IgE and IgG anti-Lol p I antibodies (Boutin et al., 1991, *J. All. Clin. Immunol.* 87 (abstract) page 197). In all cases the up-regulation has been explained by the induction of AB3 antibodies.

2.4.2 Immunotherapy with Ab1 antibodies

Regulation of the immune response by Ab1s has been investigated. Monoclonal antibodies against bovine serum albumin, given to virgin mice in the absence of adjuvant, could down-regulate the IgG response to later immunization with that antigen (Eddy et al., 1987, *J. Immunol.* 138:1693–1698). Polyclonal antibodies against sheep red cells administered pre-sensitization could also nonspecifically down-regulate the IgG response to that antigen (Heyman and Wigzell, 1984, *J. Immunol.* 132:1136–1143). The authors suggested that this effect was due to nonspecific antigen blockade by the Fc portion of the molecule. However, these studies did not demonstrate modulation of an established immune response.

Saint-Remy et al. have shown in several publications (Macheils et al., 1990, *J. Clin Invest.* 85:1024–1035; Saint-Remy et al., 1988, *Eur. J. Immunol.* 18:1009–1014) that autologous antigen-antibody complexes, made by adding antigen to sera from patients who were refractory to hyposensitization, could down-regulate the IgE response to a variety of allergic diseases including asthma and atopic dermatitis. After administration of antigen-antibody complexes, the level of anti-idiotypic antibodies was increased; this was associated with clinical improvement.

The mechanism of action in these studies has not been well investigated. Multiple mechanisms are probable, including nonspecific blockage of antigen processing via the Fc receptor, and antigen specific blockage of antigen processing (Heyman et al., 1990, *Immunol. Today* 11:310–313; Wiersma et al., 1989, *Scan J. Immunol.* 29:439–448; Sinclair et al., 1987, *Immunol. Today,* 8:7679). However it would appear that polyclonal antisera can down-regulate the IgG response. The use of monoclonal antibodies to down-regulate the IgE response is considerably more complex, in part because of the difficulty in selecting the specificity of the monoclonal antibody.

3. BRIEF DESCRIPTION OF THE FIGURES

FIG. 1 shows anti-RTA response in BALB/c mice treated with a single injection of 50 µg of immunotoxin 791T/36-RTA, measured by ELISA FIGS. 2A–2C shows binding of three anti-RTA Mabs to either native RTA, heat treated RTA (56° C. for 30 minutes) (H-RTA) recombinant RTA which is not glycosylated (rRA) or deglycosylated RTA produced by periodate treatment of the polypeptide to oxidize the terminal mannose residues (dGA).

FIGS. 3A–3B represents binding of two other anti-RTA Mabs to the same antigen preparations, with high reactivity to H-RTA and relatively poor reactivity to the other species.

FIG. 4 shows the result on anti-RTA antibody titers of treating BALB/c mice with a single dose of 100 µg delivered intravenously 24 hours after initial sensitization with 50 µg of immunotoxin. Anti-RTA titers were measured by an ELISA assay, and results are expressed as percent reduction compared to the controls, mice sensitized with immunotoxin and injected with comparable amounts of an irrelevant Mab, 365, which is directed against carcinoembrionic antigen.

Figure 10:
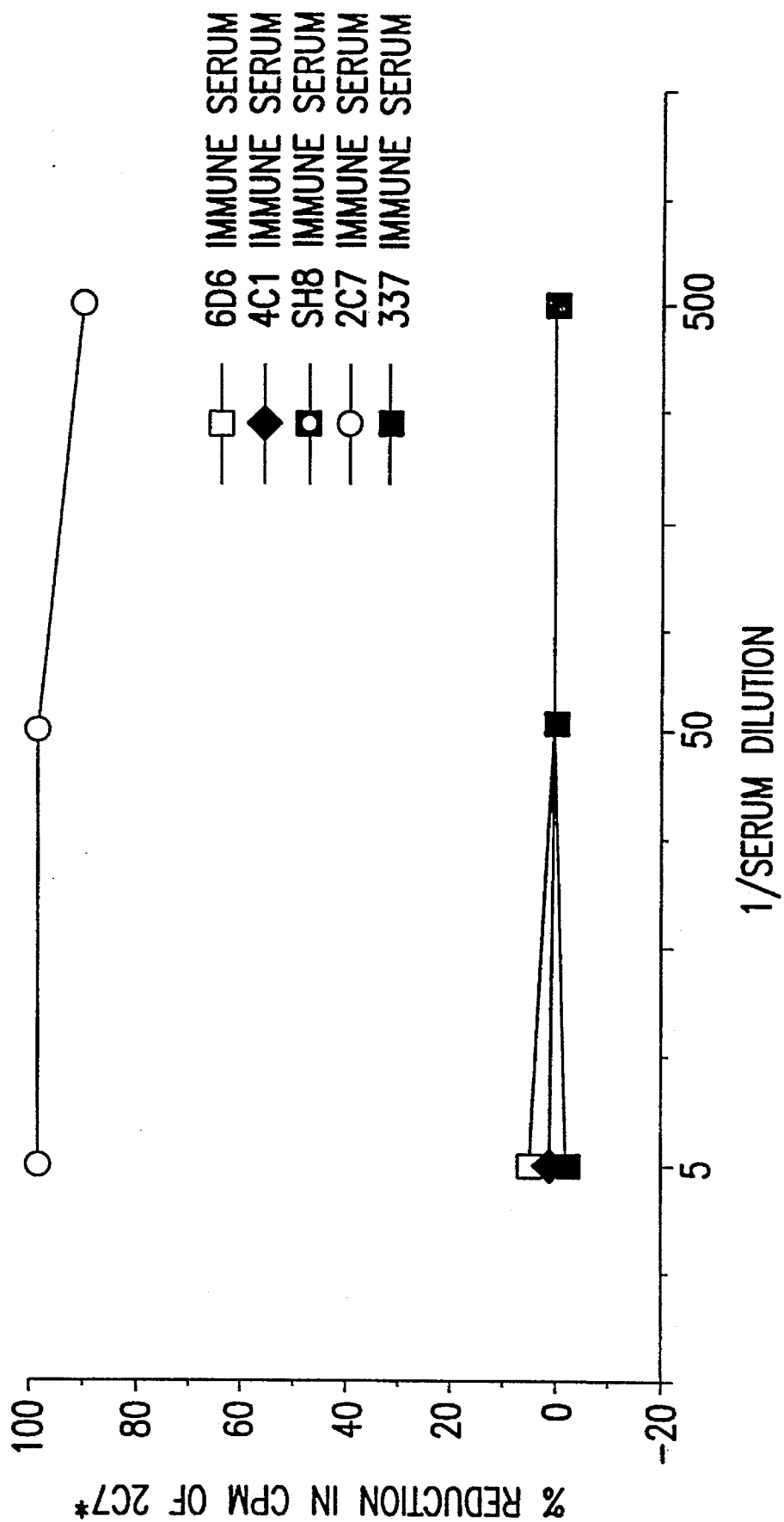

FIG. 10 is a graph showing in vitro inhibition of binding of anti-Der p I monoclonal antibody 2C7 to Der p I by murine anti-2C7 polyclonal anti-idiotypic antiserum; polyclonal antisera to other anti-Der p I monoclonal antibodies (4C1, 5H6), or to anti-Der p II monoclonal antibody (6D6), or to anti-carcinoembryonic antigen monoclonal antibody (337, included as a nonspecific control) were ineffective.

Figure 11:
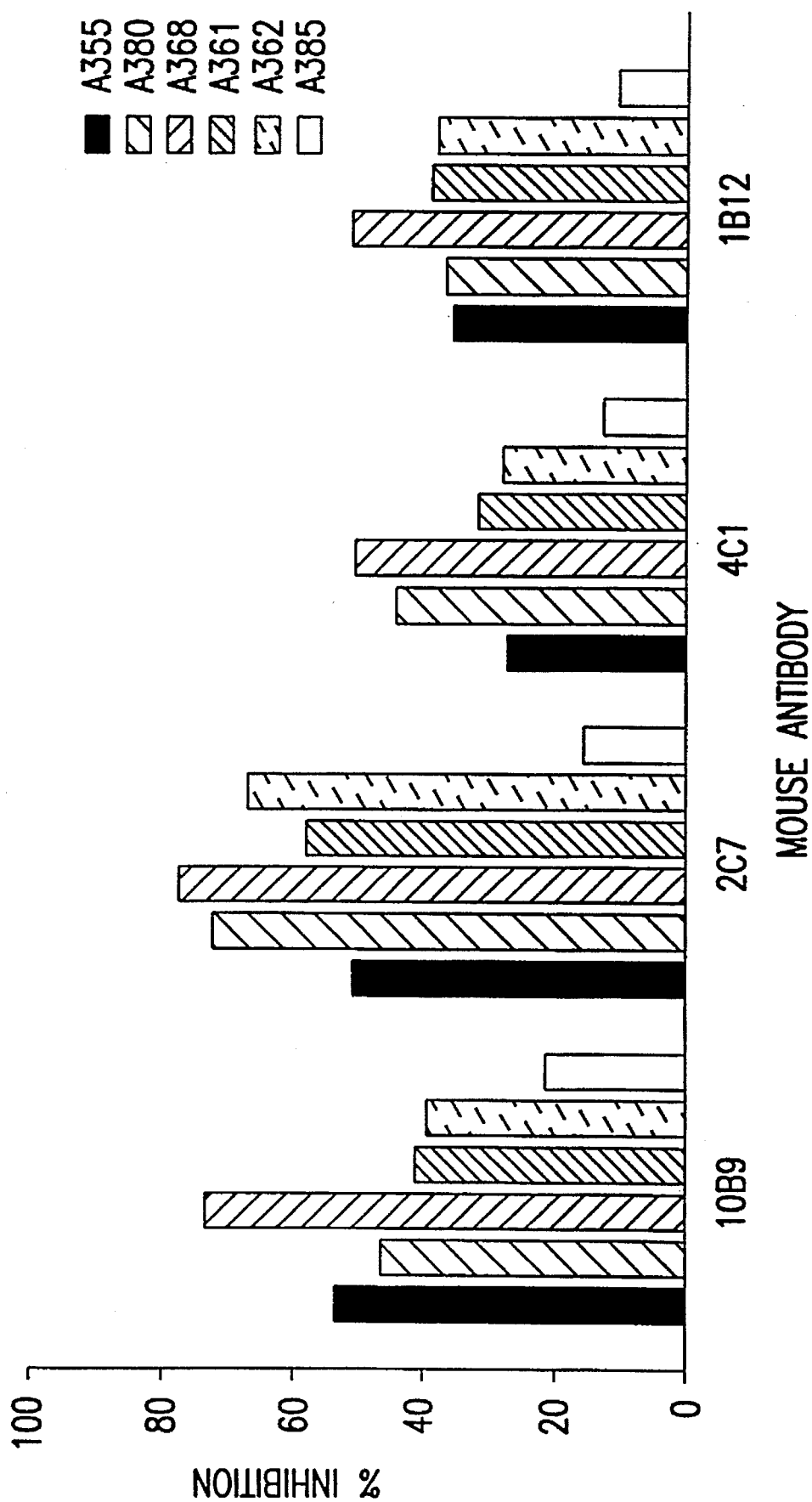

FIG. 11 is a graph showing inhibition of binding of human serum IgE to Der p I by murine anti-Der p I monoclonal antibodies 10B9, 2C7, 4C1, and 1B12; A355, A380, A368, A361, A362, and A385 represent different human IgE antisera from subjects with atopic dermatitis.

Figure 12:
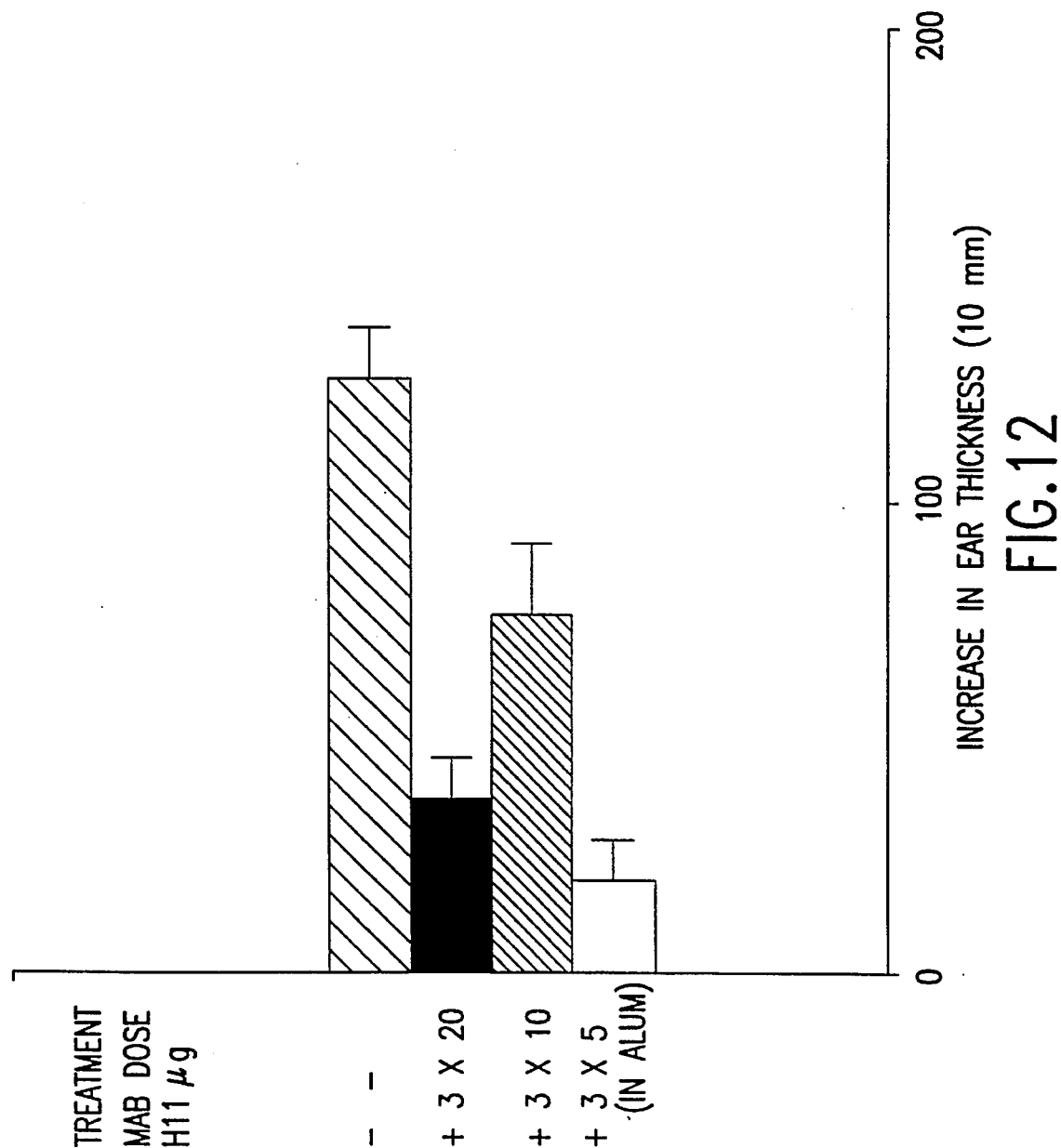

FIG. 12 represents the suppression in ear thickness of mice immunized with Der p I, then treated with three different doses of anti-Der pI MAb H11, at doses of 3×5 µg, 3×10 µg, or 3×20 µg, in alum, at days 4, 7, and 14 after sensitization. Animals are then challenged by ear injection with 10 µg DMA or with saline, on day 28. The bottom axis represents % increase in ear thickness.

Figures 13A, 13B, 13C:
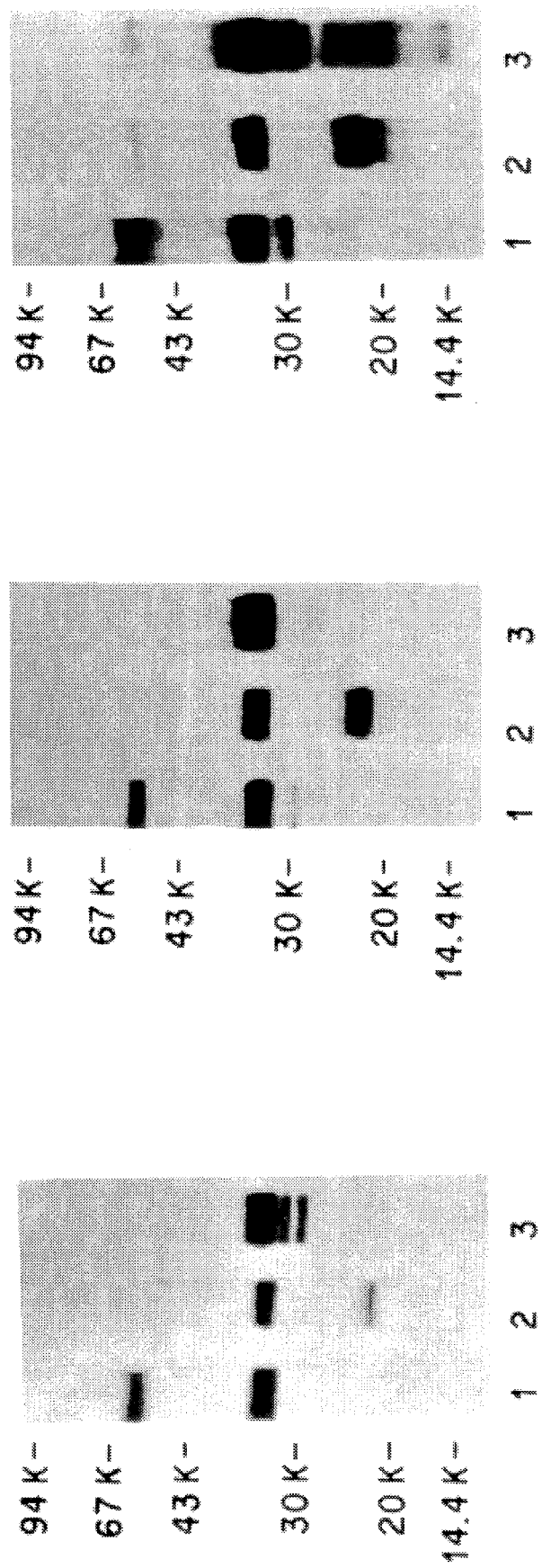

FIGS. 13A–13C represents an immunoblot profile of three monoclonal antibodies, all directed against rye Group I. The first, shown in immunoblot A, is Mab 290-A-167; the second in immunoblot B, is Mab 348-A-6; and the third, shown in immunoblot C, is Mab 539-A-6. Three antigen mixtures were used: rye group I from NIH (lane 1 in each blot), and crude rye grass extracts from Omega (lane 2) and Pharmacia (lane 3).

Figure 14:
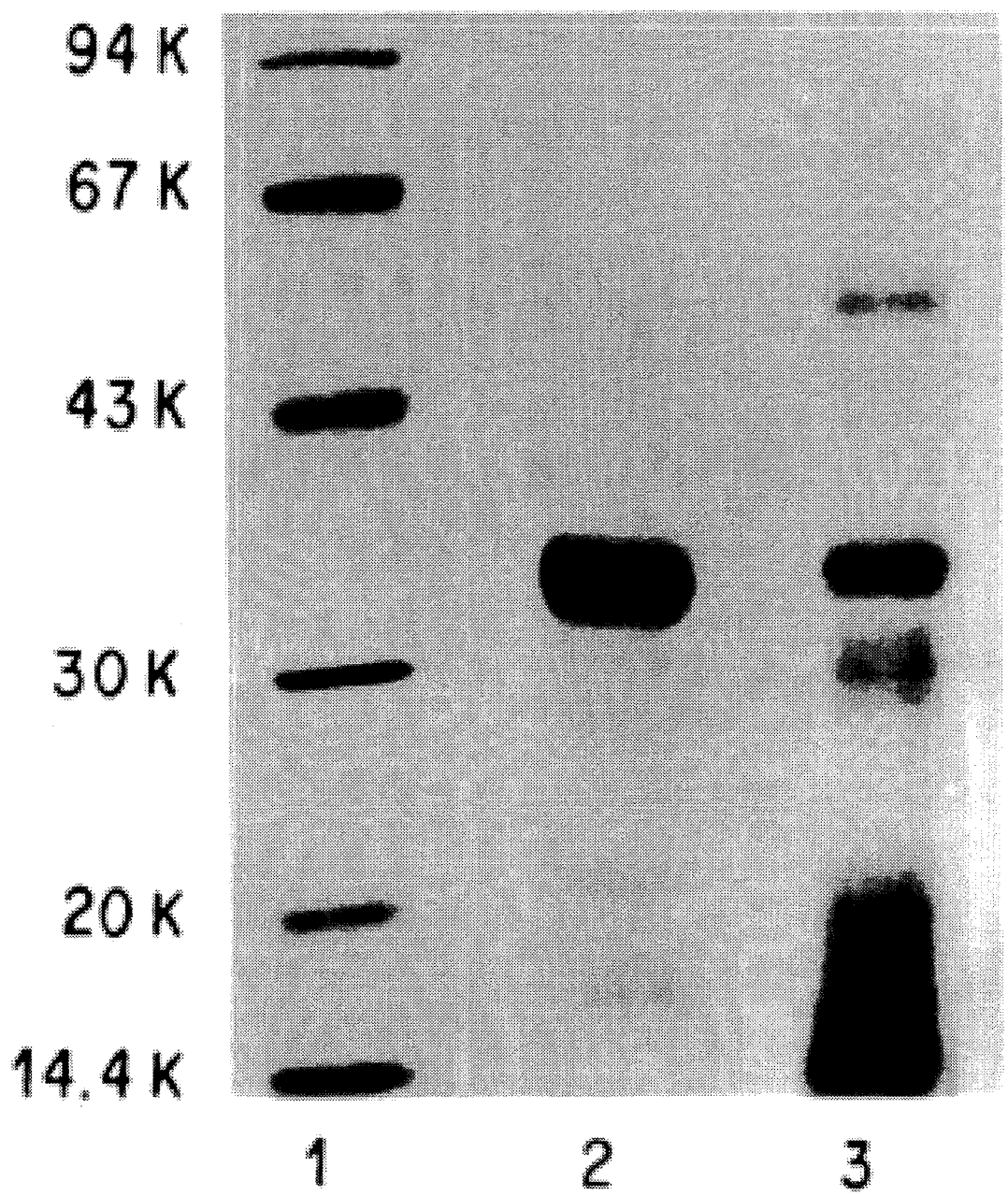

FIG. 14 shows silver nitrate-stained SDS slab gel (7.5–15% run under reducing conditions) demonstrating the molecular weights of the rye Group I antigens. Lane 1 is molecular weight markers, and lanes 2 and 3 are rye Group I antigen purified by affinity chromatography with either 5 µg/well (lane 2) or 10 µg/well (3) respectively.

Figure 15C:
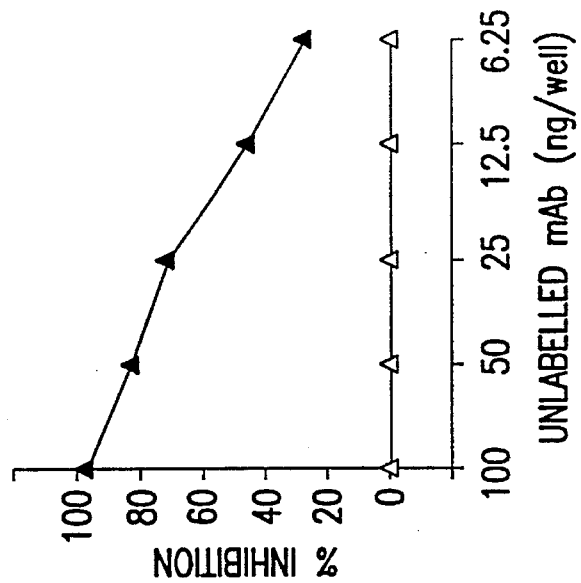
Figure 15B:
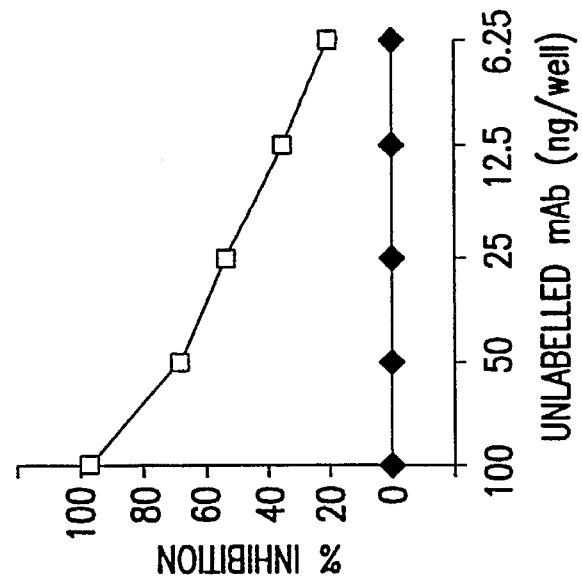
Figure 15A:
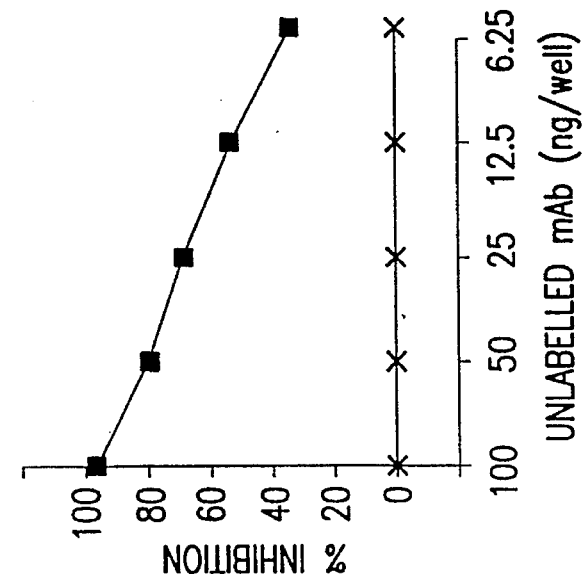

FIGS. 15A–15C shows inhibition by unlabeled Mabs (■ - - - ■, 290A-167; ☐ - - - ☐, 348A-6; and ▲ - - - ▲, 539A-6) of the binding of labeled 290A-167 (a), 348A-6 (b) and 539A-6 (c) MAbs to their homologous polystyrene-bound anti-ID Abs. 13A-12 (x - - - x); 3E12 (♦ - - - ♦), and 3E-3 (Δ - - - Δ) MAbs, were used as negative controls. Each point represents the mean value of the three experimental determinations.

FIGS. 16A–16C shows inhibition by anti-ID Abs (■ - - - ■, anti-ID of 290A-167; ☐ - - - ☐, anti-ID of 348A-6, and ▲ - - - ▲, anti-ID of 539A-6 MAbs) of the binding of labeled 290A-167 (a), 348A-6 (b), and 539A-6 (c) MAbs to polystyrene-bound rye I. Normal rabbit IgG was used as negative control (x - - - x). Each point represents the mean value of three experimental determinations.

Figure 17C:
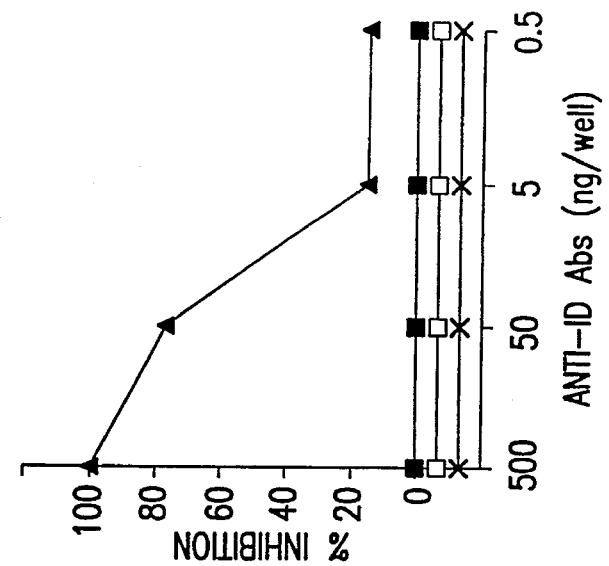
Figure 17B:
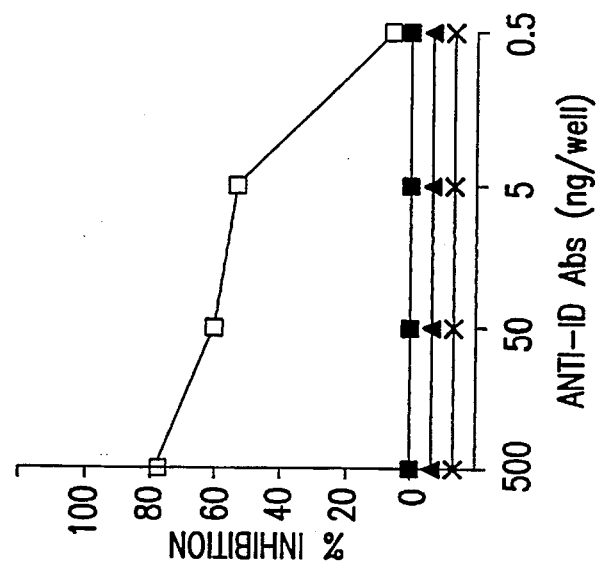
Figure 17A:
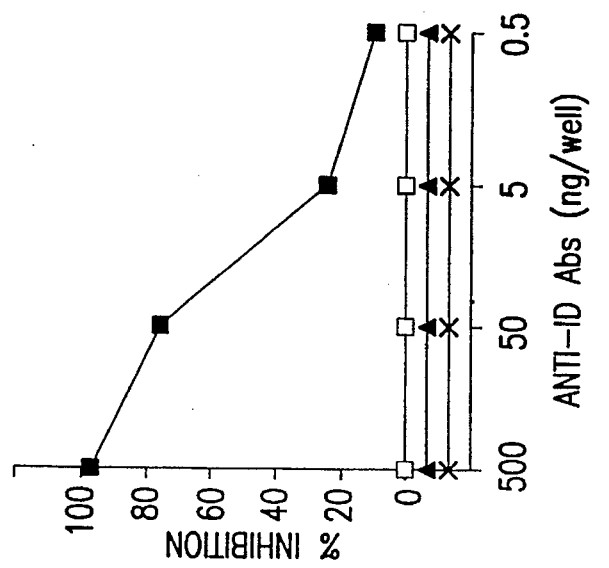

FIGS. 17A–17C shows inhibition by anti-ID Abs (■ - - - ■, anti-ID of 290A; ☐ - - - ☐, anti-ID of 348A, and ▲ - - - ▲, anti-ID of 539A-6) of the binding of labelled rye I to polystyrene-bound 290A-167 (a); 348A-6 (b), and 539A-6 (c) mAbs. Normal rabbit IgG was used as negative control (x - - - x). Each point represents the mean value of three experimental determinations.

Figure 18C:
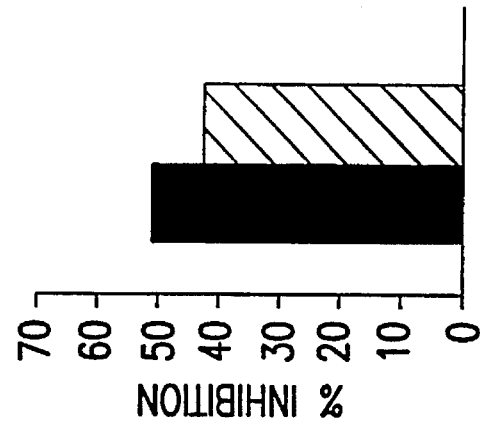
Figure 18B:
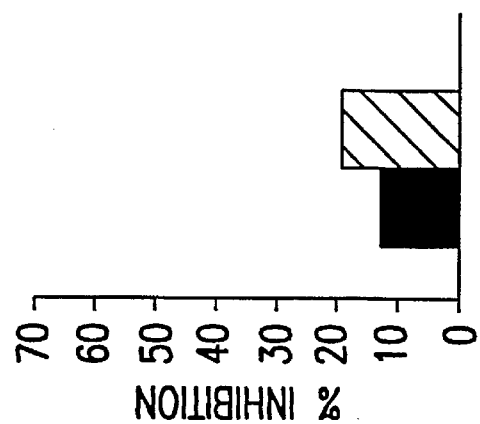
Figure 18A:
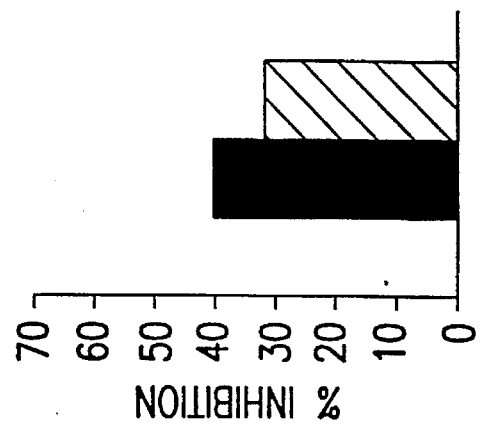

FIGS. 18A–18C shows inhibition by anti-rye I MAbs ($_{13}$) [290A-167 (a), 348A-6 (b) and 539A-6 (c)] or their homologous anti-idiotypic Abs (__) (of the binding of human IgE to polystyrene-bound rye I. The concentration of each Mab was 1 µg/ml and for anti-idiotypic antibody, the concentration was 250 µg/ml.

FIGS. 19A–19C shows inhibition of binding of labeled (290A-167 ▲ - - - ▲, 348A-6 ♦ - - - ♦, 539A-6 ▲ - - - ▲) to solid phase fixed rye I antigen by human auto anti-ID antibodies form three (A, B, C) sera depleted of anti-rye I antibodies. The inhibited bindings of Mabs were as follows: 290A-167=34,400 c.p.m., 348A-6=78,526 c.p.m. and 539A-6=67,006 c.p.m. [The binding of anti-Hbs Mab (3E3) as control to its antigen was 43,988 c.p.m. and was not inhibited by any autoanti-ID antibodies.]

Figure 20:
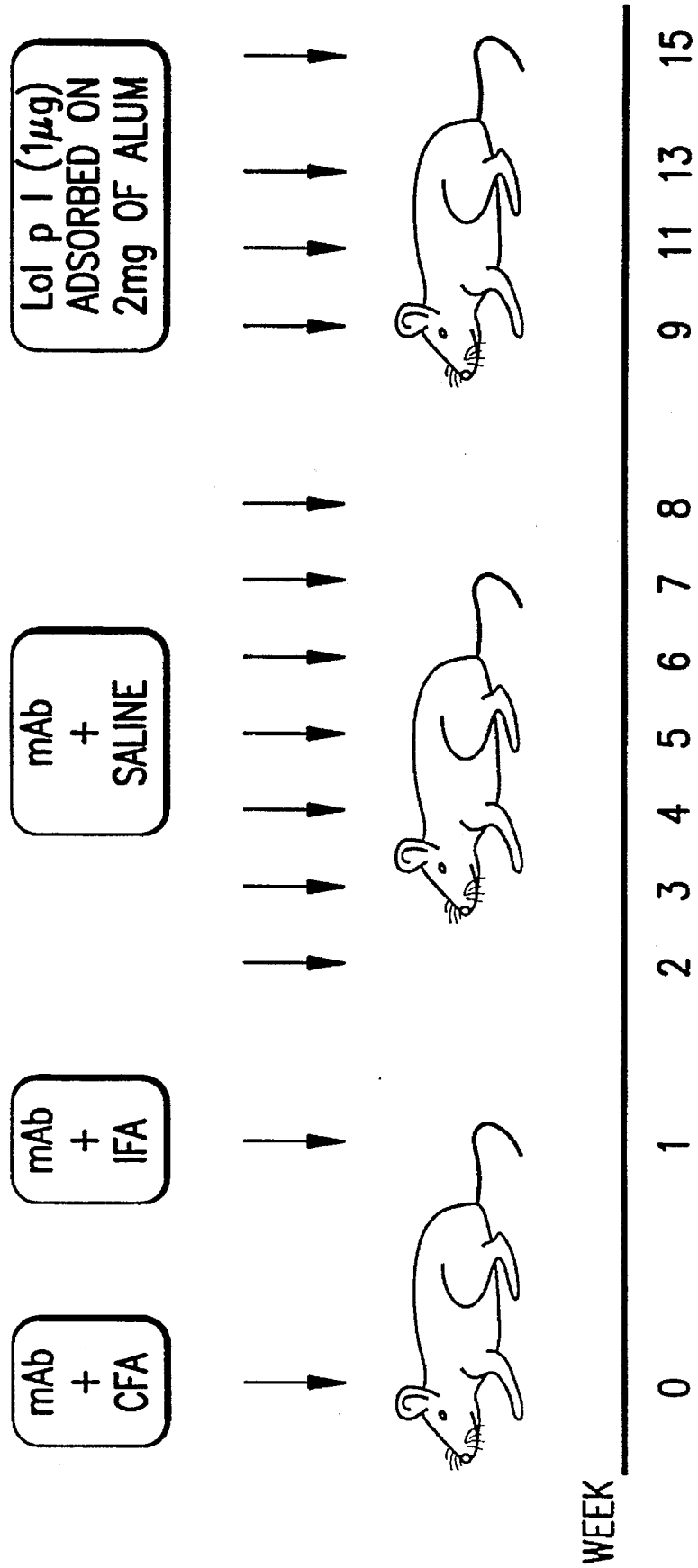

FIG. 20 shows (specific suppression of anti-allergen antibodies by administration of idiotypic antibody). Groups of mice were immunized by i.p. injection of various amounts (0.01–10 µg) of 290A-167 (Id) or 10 µg of unrelated Mab (5 mice/group). Blood samples were regularly drawn and tested for specific anti-Lol p I Abs in ELISA or PCA assays.

Figure 21:
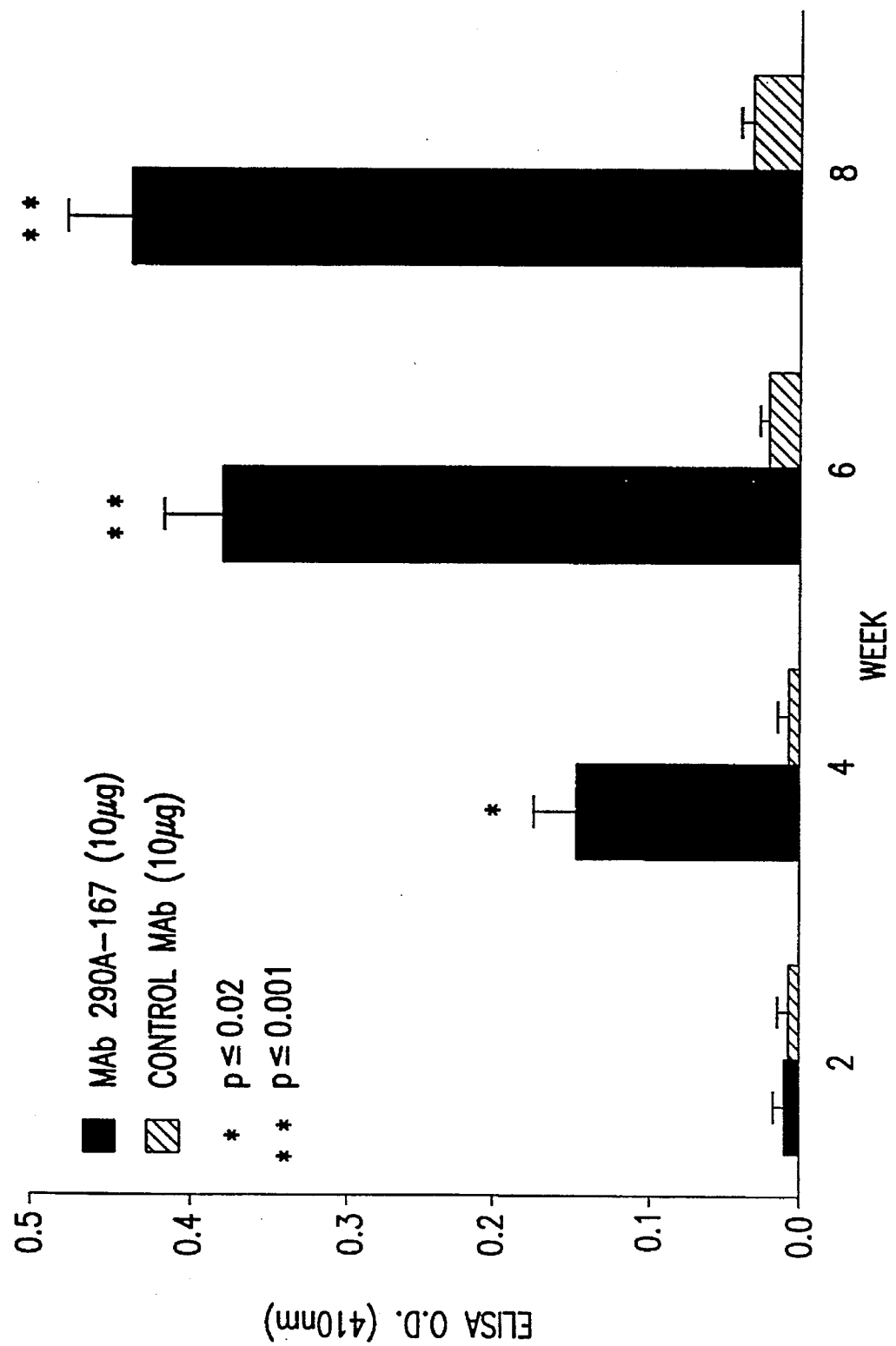

FIG. 21 shows change in specific antibody levels over time. Animals were injected with Mab 290, or an anti-transferrin Mab of the same subclass as Mab 290, which does not cross react with that antigen; and Lol p I antigen using the scheme shown in FIG. 11. Sera were drawn at 2 week intervals, and binding to Mab 290 was measured at a dilution of 1:100 by an ELISA assay as described.

Figure 22:
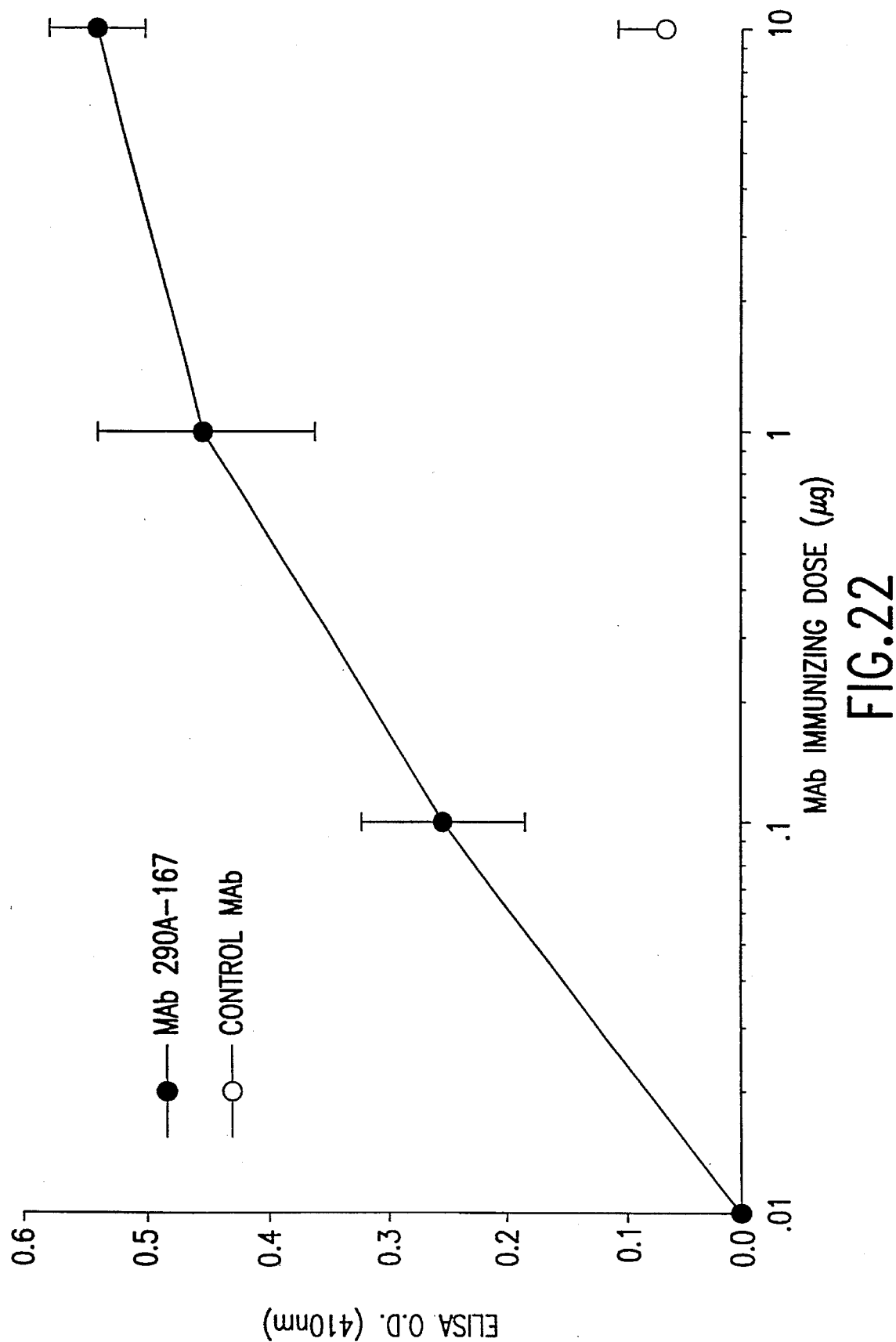

FIG. 22 shows anti-idiotypic antibody levels as a function of Mab 290 dose. Groups of five mice were injected with Lol p I antigen, and concentrations of Mab 290 or with 10 µg of the anti-transferrin Mab. ranging from 0.01 to 10 µg using the Scheme pictured in FIG. 10; The levels of anti-idiotypic antibodies reactive with Mab 290 were assayed at a dilution of 1:100 by an ELISA assay as described in the text. The right axis represents Mab immunizing Dose (µg).

Figure 23:
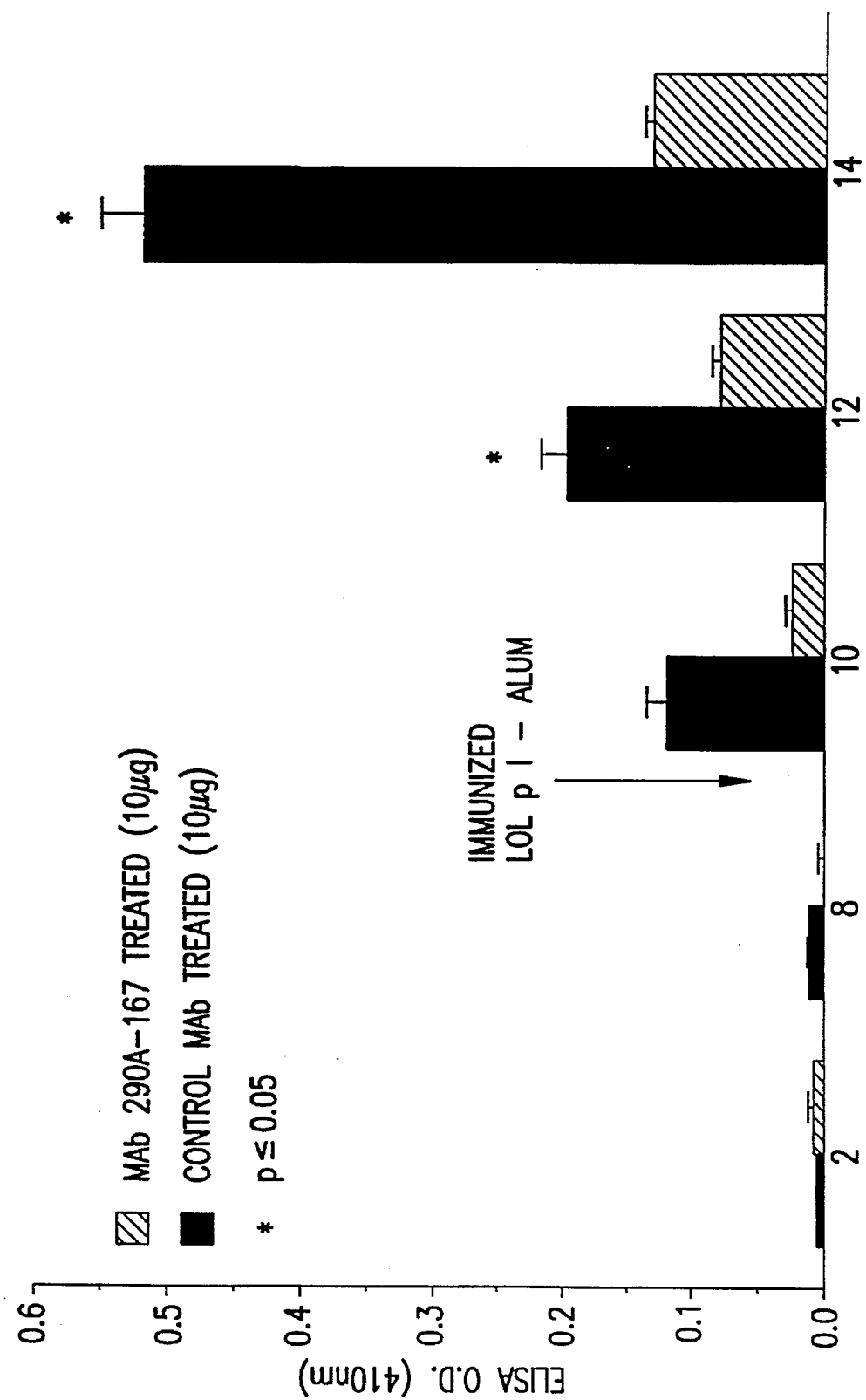
Figure 24:
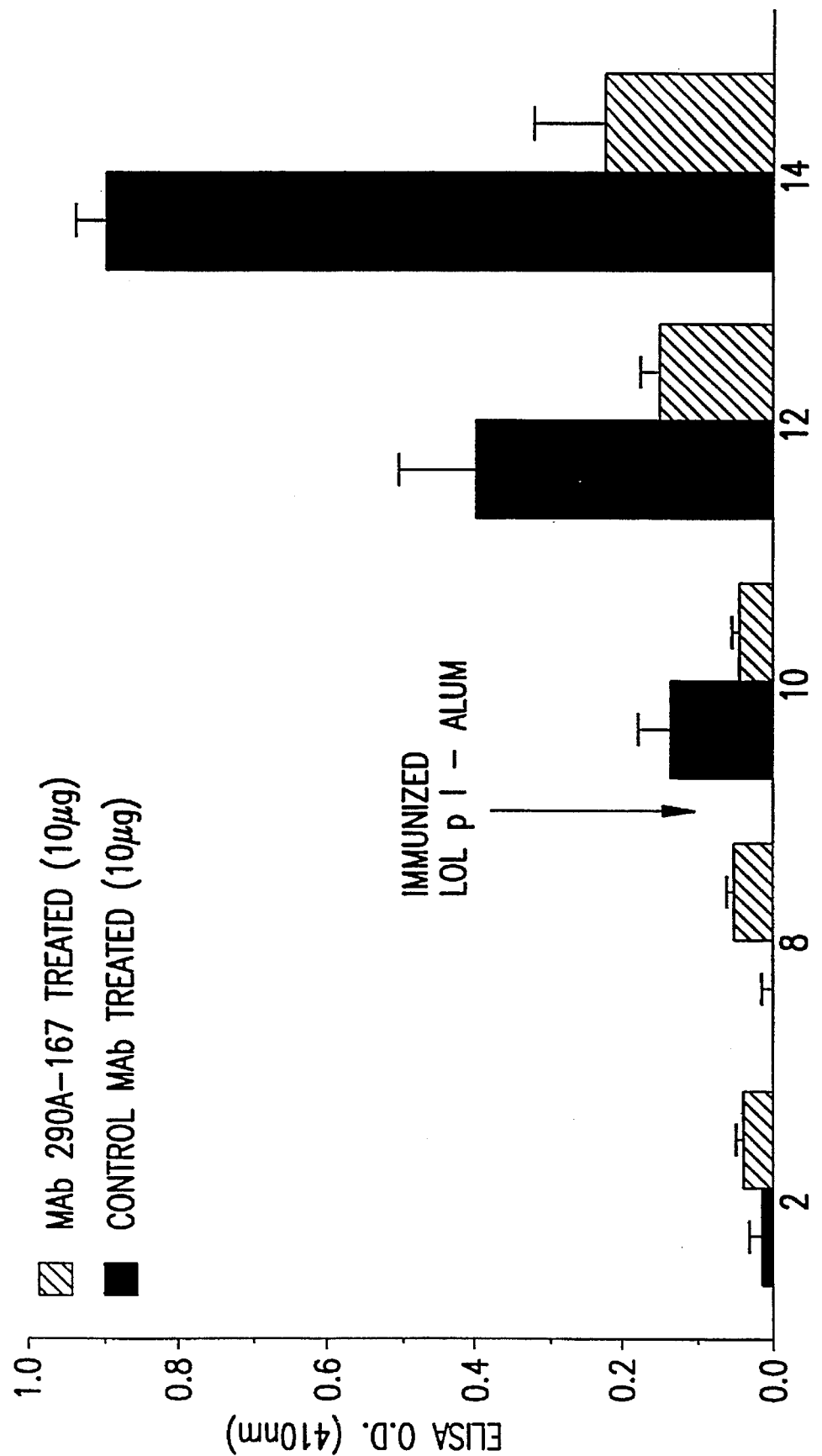
Figure 25A:
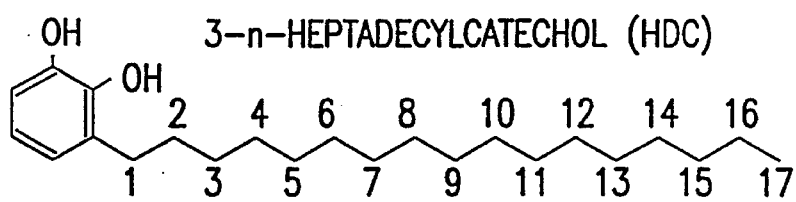
Figure 25B:
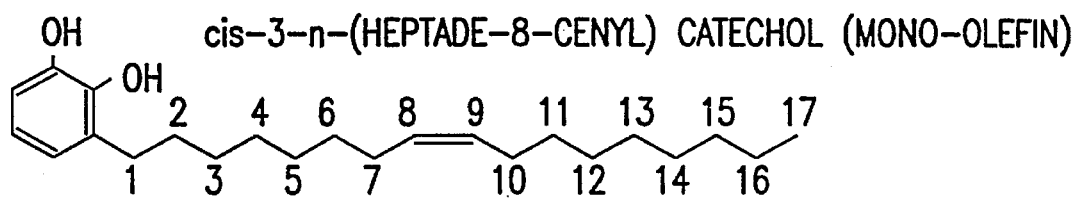
Figure 25C:
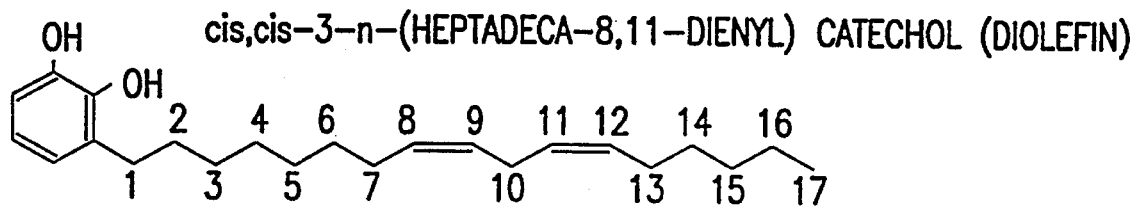
Figure 25D:
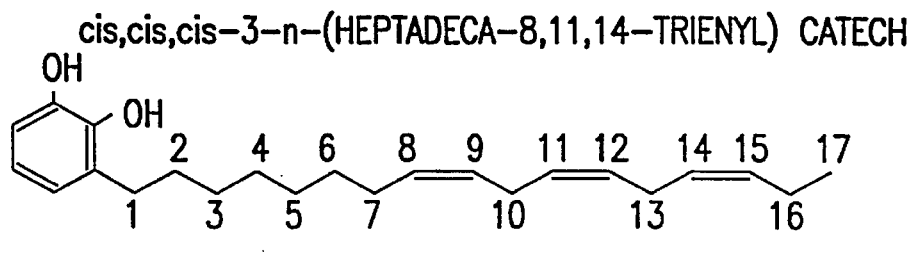

FIG. 23 and 24 depict specific inhibition of IgE and IgG antibodies by Mab 290. Groups of 5 mice were injected with 10 µg of Mab 290 (termed ID in the figure legend) or unrelated Mab (anti-transferrin) of the same subclass. After depletion of anti-idiotypic antibody activity, sera were either diluted 1/50 and assayed for anti Lol p I antibody of the IgE class, or diluted 1/100 and assayed for anti Lol p I antibody of the IgG1 class. The mice had last been immunized with Lol p I at week 9.

FIGS. 25A–25D depicts the structure of urushiol, the series of alkylcatechols in poison oak/ivy, with a C15 of C17 side chain.

Figure 26:
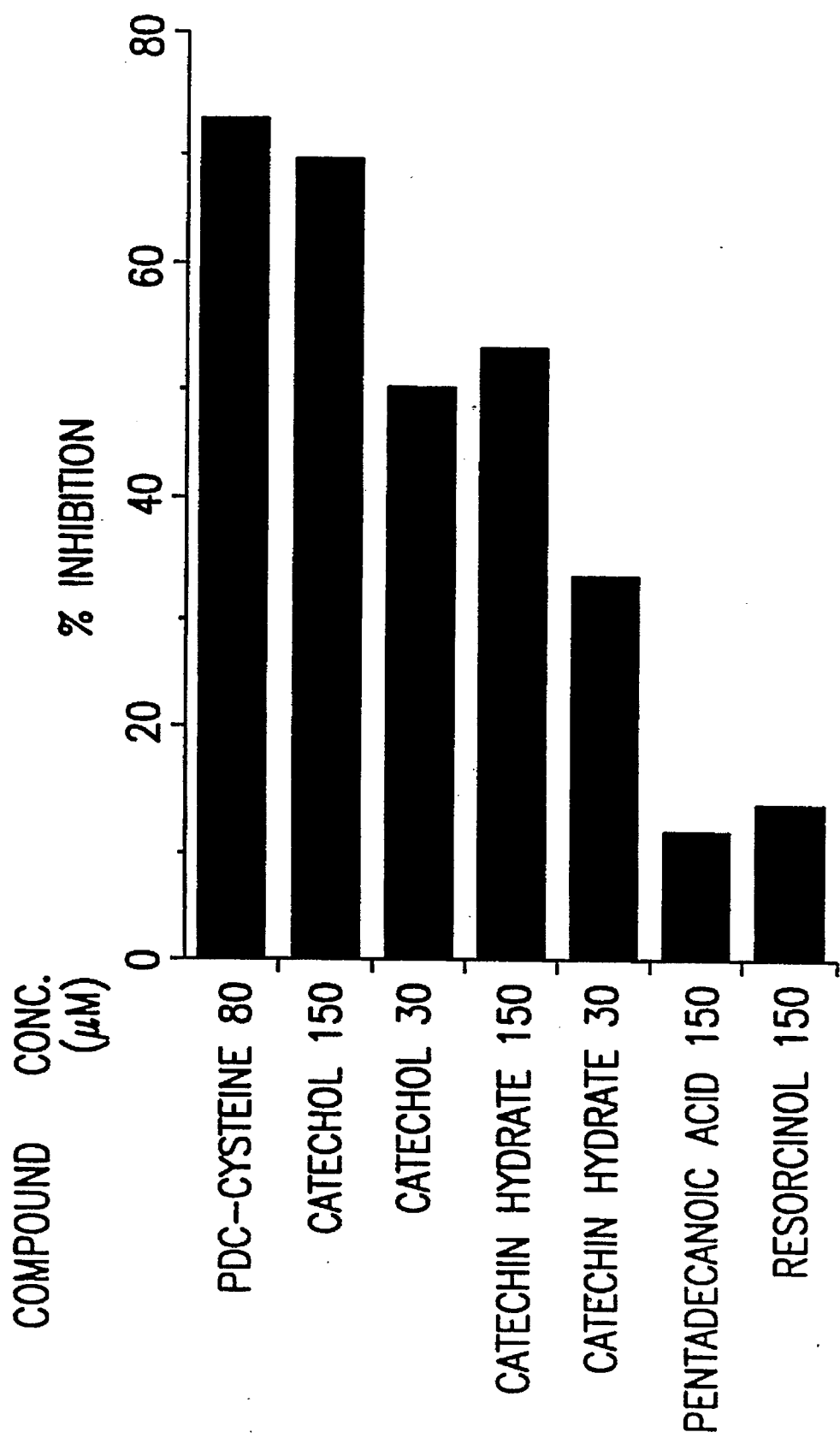

FIG. 26 summarizes studies in which binding of radiolabelled MAb 991 to pentadecylcatechol (PDC) was measured in the presence of a variety of related compounds. Maximal inhibition of binding was noted with PDC and the catechols; minimal with pentadecanoic acid, an analog of the side chain, or with resorcinol, and analog of the catechol ring but with hydroxyl groups in different positions.

Figure 27:
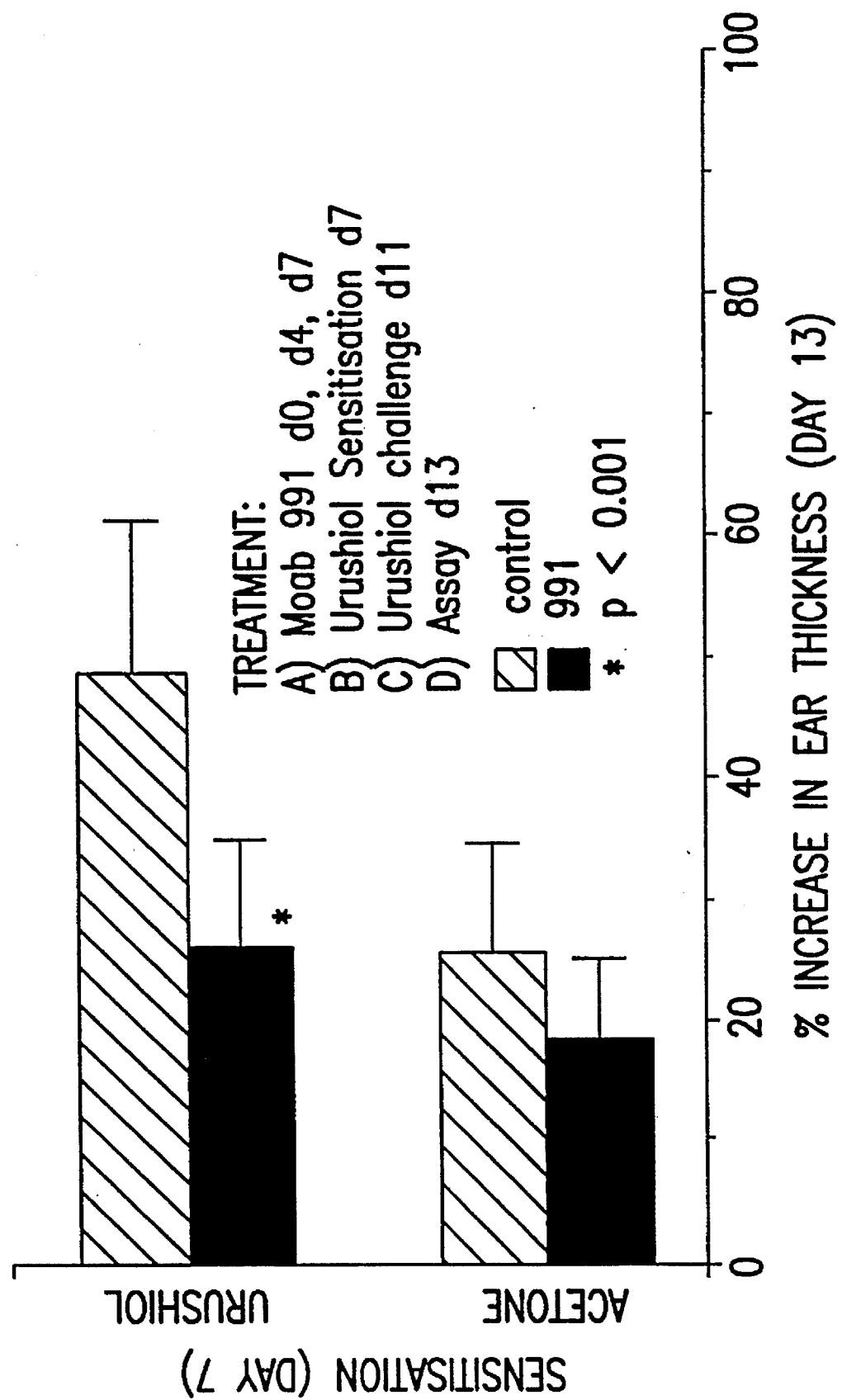

FIG. 27 depicts results of experiments in which BALB/C mice were pre-treated with one or more doses of MAb 991, then sensitized to PDC, and challenged (by ear painting) with the same compound.

Figure 28:
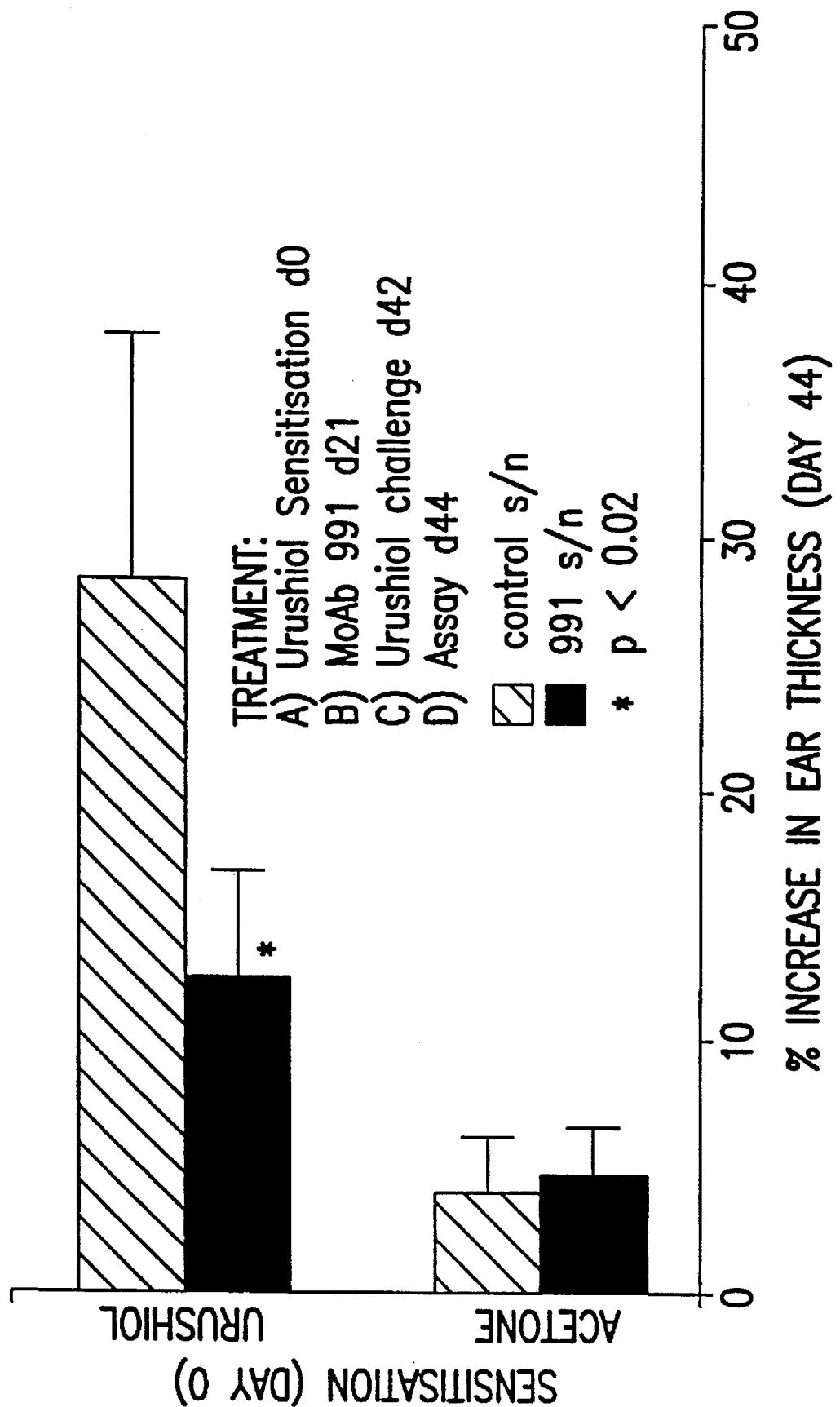

FIG. 28 depicts results of experiments in which mice are initially sensitized with PDC or urushiol, then injected with MAb 991, 21 days later, after which they are challenged on day 42 by ear painting.

Figure 29:
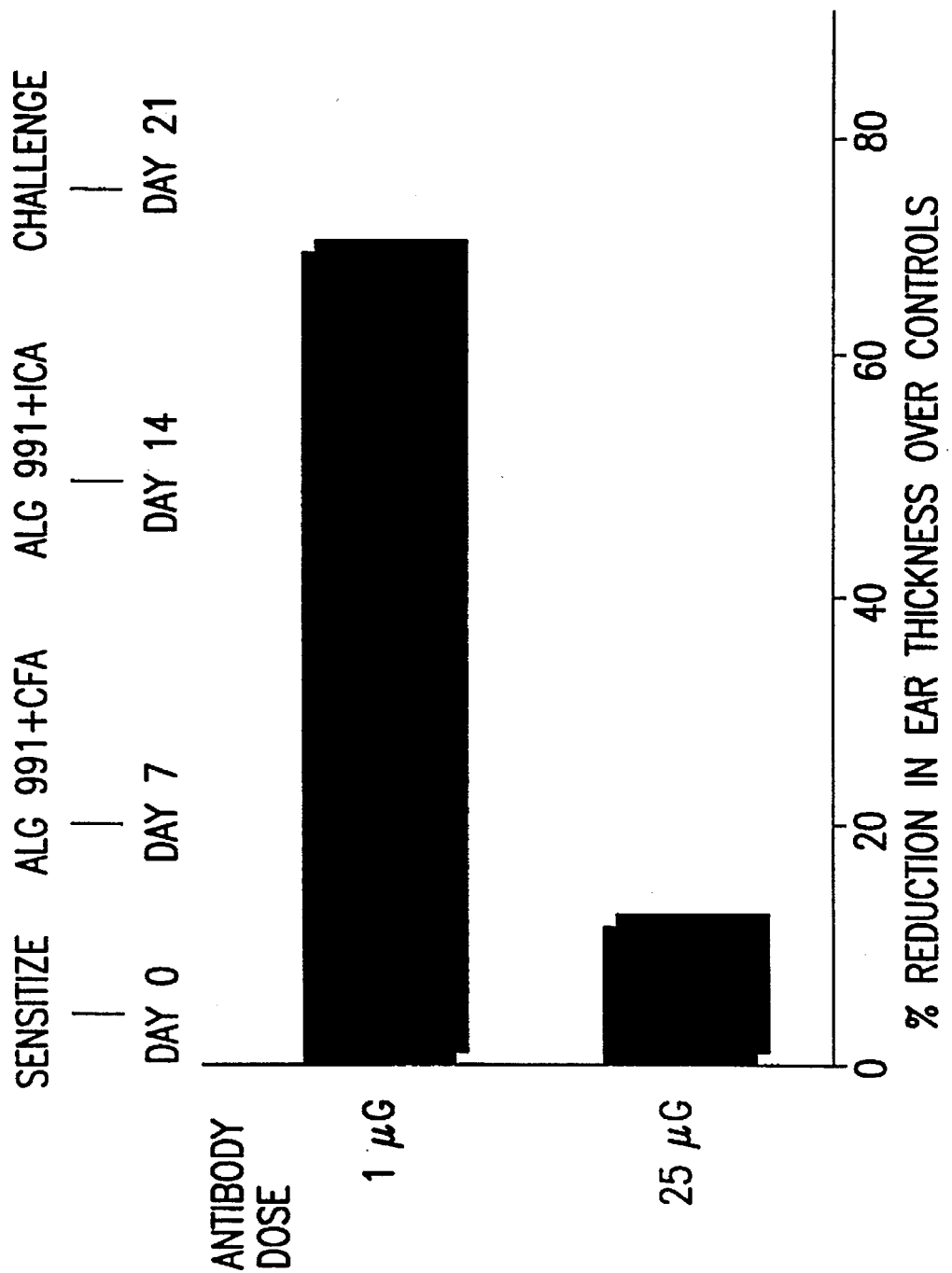

FIG. 29 depicts results of experiments in which sensitized BaLB/C mice are injected with a variety of different doses of MAb 991 in alum prior to challenge. In this case, the percent reduction in ear thickness over controls is plotted, with the background (nonspecific) swelling subtracted.

4. SUMMARY OF THE INVENTION

The present invention provides novel compositions and methods useful in the modulation or selective suppression of host immune responses to an immunogen of interest, particularly to immunogens which are exogenous antigens or allergens. Subject compositions include antibody, antibody derived, and antibody-like molecules of primary antigen reactivity with respect to the immunogen of interest. Antibodies or antibody-like or antibody-derived molecules include antibody fragments such as Fab, and complementarity determining region peptides (CDRs) which may be grafted into a framework region of any species, particularly human. They also include human antibodies, derived from sensitized human lymphocytes produced by cell fusion with heterohybridomas, or by DNA cloning and expression. Other compositions include T cell receptor (TCR) molecules, obtained either from T cell clones or hybridomas or as purified TCR preparations. Immunoreactive peptides corresponding to some or all of the complementarity determining regions or hypervariable regions of the TCR are also employed.

In preferred embodiments, antibody and antibody-derived molecules and TCRs are directed against dominant epitopes of the allergen of interest. Allergens include haptens, such as urushiol and certain pharmaceuticals, as well as allergenic proteins such as those in dust mite allergens, mold spores, and pollen.

Allergens to be down regulated may be from environmental sources, from food, from cosmetics, or from drugs and therapeutics. Immune responses to be down regulated include, but are not limited to, T cell reactions such as those causing poison oak and ivy dermatitis, as well as those initiating IgE mediated diseases such as asthma, allergic rhinitis and atopic dermatitis. An especially important class of allergens are those which are commonly airborne. Airborne allergens are a significant source of asthma and allergic rhinitis since subjects frequently are exposed to airborne allergens via inhalation into the lungs, bronchioles, and nasal passages, or by airborne contact with conjunctiva. IgE-mediated allergic responses such as asthma and allergic rhinitis and atopic dermatitis are regulated by the proposed methods, as well as allergic reactions mediated by IgG responses. IgG-mediated allergic reactions are especially important mediating in sensitivity to drugs and to injected allergens as exemplified by ricin A chain.

Compositions of the present invention are believed to suppress host immune response to the immunogen of interest, at least in part by stimulation of anti-idiotypic antibodies and by interactions with cells involved in antigen processing and stimulation of the immune network.

The present invention also provides methods for selective suppression of host immune response to an immunogen of interest by administering a compound of the invention. In a preferred embodiment, subject compositions may be administered to the host after the host has been sensitized to the immunogen, thereby downregulating the host sensitivity. Composition also may be administered to the host prior to sensitization.

5. DETAILED DESCRIPTION OF THE INVENTION

As used herein, an Ab1 or idiotypic molecule is an antibody, TCR, or antibody- or TCR-derived molecule which binds to or reacts with a primary immunogen or allergen. An Ab2 or anti-idiotypic molecule is an antibody, TCR, or antibody- or TCR- derived molecule which binds to or reacts with an Ab1 or idiotypic molecule against the primary immunogen. Thus the Ab1 or idiotypic molecule itself functions as a secondary antigen in that it can produce an anti-idiotypic response. Of particular relevance are Ab2 molecules which bind to the allergen binding site of the Ab1.

As used herein, the term "antibody-derived" molecule refers to an antibody, an antibody fragment, a hybridized antibody or antibody fragment, or a chimeric molecule comprising an antibody binding domain and a heterologous polypeptide. Antibody-derived molecules of the invention contain at least a binding domain of an Ab1 against the allergen of interest. The binding domain includes the complementarity-determining regions (CDRs) of the Ab1, joined to a framework region (FR). The FR may be a sequence from an animal or a human; replacement of animal FRs with human FRs produces a humanized binding domain.

The constant domains of an antibody from an animal may be replaced by corresponding domains from a human to produce humanized antibodies. Antibody-derived molecules of the invention comprise both humanized binding domains and humanized antibodies.

A TCR may be employed analogously to an antibody-derived Ab1. A TCR which contains a binding site for an epitope of an allergen of interest is capable of functioning in a manner similar to an antibody-derived Ab1. A "TCR-derived" molecule refers to a TCR, a TCR fragment, a hybridized TCR or TCR fragment or a chimeric molecule. Particular embodiments of TCR derived molecules incorporate the binding domain of a TCR, but may have other domains of the TCR deleted, or may be formed into a chimeric molecule with soluble domains from other proteins, such as serum albumin. For convenience, references herein to "Ab1s" includes TCR-derived molecules which bind to an epitope of the allergen of interest, unless the context precludes this meaning.

A preferred embodiment of the invention comprises antibody—or TCR-derived molecules which have been isolated and purified. As used herein, the term "isolated" means a composition which is free of substantial or immunologically active amounts of serum components other than antibody—or TCR-derived molecules. In particular, isolated antibody-derived molecules are substantially depleted in major serum proteins and cytokines or lymphokines. "Purified" antibody or TCR-derived molecules are depleted of molecules which do not bind to the allergen of interest; in particular, purified Ab1s are depleted of Ab2s and of Ab1s directed to other antigens.

However, compositions of the present invention may comprise Ab1s to which non-immunologically active molecules have been added, e.g., serum albumin from the species to which the composition is to be administered.

A particular preferred embodiment comprises Ab1 antibody—or TCR-derived molecules which are substantially free of the allergen to which the Ab1 molecule binds. "Substantially free" means that the ratio of the number of antibody binding epitopes is at least 10:1, preferably 100:1, more preferably 1000:1.

One category of exogenous antigens of interest is referred to as environmental allergens. As used herein, the term "environmental allergen" refers to an allergen to which an animal, including a human, is exposed by external contact, and includes dermal or conjunctival contact and inhalation of airborne allergens. Environmental allergens include both immunogenic macromolecules and haptens.

Particular environmental allergens of interest include pollens. Pollen is wind-dispersed by many types of higher plants, including gymnosperms (e.g., pines and cypresses), dicotyledonous angiosperms (including broadleaf trees such as elms and many common broadleaf weeds such as ragweed and plantain) and monocotyledonous angiosperms (e.g., the grasses). The methods presented here are applicable to any pollen allergen. Other allergens include dust mite antigens consisting of proteins from the body and feces of the dust mite, found in house dust, mattresses and carpet, but capable of becoming air-borne. They also include molds such as *alternaria*. The methods presented here are applicable to any of these allergens.

A second category of exogenous allergens of interest is those derived from foods and food products. Numerous food components, particularly proteins, are known to cause food allergies. Examples are proteins of wheat and related cereal grains, and of legumes such as peanuts. The allergenic proteins of wheat and peanuts have been isolated. Ab1s against allergenic wheat and peanut proteins are particular embodiments of one aspect of the invention, e.g., compositions comprising Ab1s against food allergens. Administration of compounds comprising Ab1-derived molecules against food allergens are useful for suppression of food allergies.

A notable example is provided by wheat gluten and related proteins. These are potent allergens in some individuals, and provoke IgG mediated reactions to wheat products in the diet. Administration of compounds comprising Ab1-derived molecules against food allergens are useful for suppression of food allergies. Compounds and methods of the present invention provide for downregulation of IgG reactions, as seen with the ricin A chain allergen which can be useful as a component of cytotoxic drugs. Another example of an immunogenic protein drug is provided by insulin. Diabetics receiving either animal or recombinant human insulin often develop anti-insulin antibodies.

Other food allergens for which particular proteins have been implicated are summarized in Sampson et al., JAMA, 1992, 268:2840–2844.

A third category of exogenous allergens of interest is drug and therapeutic allergens. Prominent examples of drug allergens are the various penicillins and related β-lactam antibiotics. Allergic reaction to penicillins can be life-threatening. Administration of a composition comprising an Ab1-derived molecule against a β-lactam antibiotic is useful for suppression of antibiotic allergy.

A fourth category of interest are those haptens and low molecular weight chemicals such as urushiol (poison ivy/ oak) or industrial and environmental chemicals causing either contact dermatitis or pneumonitis.

The responses to be down-regulated can be those mediated by T cells, as exemplified by poison oak dermatitis, or IgE, exemplified by Dust Mite Antigen, or Rye Grass, or by IgG, exemplified by ricin A chain or Rye Grass.

Ab1s useful in downregulation of an allergic response may be of any antibody class and subclass, e.g., IgM, IgE, $IgG_1$, $IgG_2$, $IgG_4$, etc., and may include TCRs. Class identity is of secondary importance compared to the characteristics of the binding domain. Ab1s are believed to act in part by stimulating the formation of AB2s directed against the binding domain of the Ab1. Although the specific binding domain of the Ab1 therefore is critical, other portions of the Ab1 molecule may be modified appreciably, including those portions of the antibody which determine class.

For similar reasons, fragments of the Ab1 are active, provided that the desired allergen epitope binding domain is present. Any of the common antibody fragments which retain binding specificity may be used. Also, cloned "fragments," or partial antibody sequences obtained by expression of abbreviated genes encoding the binding domain, are within the scope of the invention.

Furthermore, chimeric molecules in which the Ab1 binding domain is joined to other proteins or protein domains also are active immunoregulators. The chimeric protein "partner" to which the allergen binding domain is joined may be selected from a great variety of sequences. In some cases the binding domain from an antibody of one class may be joined to the constant regions of another class to produce a class-switched antibody. When the constant region is from a different species from that of the binding domain, the resulting chimeric antibody is partially species switched. This procedure may be used to create partially humanized antibodies which have lessened antigenicity when injected into humans.

In particular instances, a chimeric partner may be chosen because it imparts desirable solubility or localization characteristics. For example, an allergen binding domain may be joined to a collagen domain of the target species. The resulting chimera remains localized at the injection site due to binding of the collagen domain to extracellular matrix. In other instances a chimeric partner is chosen because it is itself immunologically active and acts as an adjuvant. Examples include antigenic domains from proteins of common bacterial pathogens.

Since immunoregulatory molecules of the invention do not require constant domains for activity, the Fc portion of the IgG constant domain is not necessary for immunosuppression. This result is counter to the suggestion in the work by Heyman et al., that the Fc domain is critical for immunosuppression.

5.1 Production of monoclonal antibodies

Murine monoclonal antibodies to the antigen of interest are prepared by methods well known to those skilled in the art (Goding, supra). BALB/c mice are immunized with specific antigen preparations using a variety of protocols including use of immunological adjuvants such as complete and incomplete adjuvant. Spleen cells are prepared from mice shown to be producing antibodies of the proper specificity, and fused with cells from murine myeloma cell lines such as Ps-NS1, Sp 2/0, X63-Ag8.654, NSO/1 or the like by established procedures (Kohler and Milstein, 1975, *Nature* 256:495–497; U.S. Pat. No 4,376,110). Clones are selected by two rounds of limiting dilution. Hybridoma cells are then either maintained in culture or propogated in the peritoneal cavity of BALB/c female mice after prior injection of pristane (0.5 ml). Ascitic fluid is harvested from mice 10 to 15 days after hybridoma cell injection and antibodies purified by passing the fluid through a protein A-Sepharose 4B column.

5.2 Production of humanized monoclonal antibodies

The most advanced technology for humanizing monoclonal antibodies has been termed CDR-grafting or reshaping (Riechmann et al., 1988, *Nature* 332:323–327). In this scheme, the complementarity determining regions (CDRs) of a murine antibody are transplanted into the corresponding regions in a human antibody. There are three CDRs in the heavy chains and three in the light chains, and they are the regions of the mouse antibody which binds to a specific antigen. The CDRs are identified by ascertaining the amino acid sequence of the variable regions of the mouse monoclonal antibody to the sequences of all known mouse variable regions, and the sequences of all known human variable regions. These are obtained by reference to Kabat et al. (Sequences of Proteins of Immunological Interest, 4th ed. U.S. Department of Health and Human Services, U.S. Government Printing Office, Washington, D.C., 1987). This allows the division of the variable regions of the murine monoclonal antibody into the framework regions (FRs) and the CDRs. Since the CDRs are unique for each antibody, and the framework is relatively homologous for all antibodies of a given isotype, this comparison reveals the numbering of the amino acids comprising the CDR. In order to graft these CDRs onto a human framework, two basic methods can be used. The chimeric light and heavy chains can be constructed from the genomic DNA clones of the mouse hybridoma, and then these variable regions can be linked to the human constant regions in expression vectors which contain the designated human constant regions. Often the 5' and 3' ends of the cloned CDNAs are modified by using the polymerase chain reaction (PCR). (Erlich et al., 1988, *Nature* 331:461–462) These vectors are then introduced into mammalian cells such as the COS cell line, and the supernatant fluids are analyzed to confirm retention of antibody binding. After this, PCR technology is used to insert the mouse CDR's into available human framework regions, or the entire variable region may be sequenced based on the sequence of the mouse CDRs and known human framework regions. A range of human framework regions exist, and have been inserted into expression vectors. The available human framework region which most closely mimics the amino acid sequence of the murine antibody is selected, since it would be predicted that the CDRs would find a better "fit" into such frameworks. These reshaped human variable regions are cloned into the expression vectors containing the designated human constant regions, and the vectors are introduced into cos cells, either by electroporation in which DNA is added to cells such as cos cells, and the mixture pulsed with voltage (such as 1,900 volts, 10 minutes), incubated and washed. The supernatant is again tested for presence of antibody which retains the binding of the initial antibodies. Often, during the design process a few positions in the human framework regions will have been highlighted as critical positions. It may not always be clear whether it is best to retain the amino acids found at those positions, or whether they should be changed to those which were present in the initial murine antibody. Therefore, if binding is suboptimal, these changes can be made at a later date.

For optimal expression, (since cos cells, while easy to work with, are often not high antibody producers) the vectors are introduced into a different mammalian cell line such as CHO cells.

In other variations of this technique, the CDRs may be cloned directly, and inserted into vectors containing both the variable region framework, and the constant region framework region of the desired human antibody. These techniques, have several variables, among them the primers and vectors used, the cells used as expression systems, the human frameworks which most closely mimic the murine antibody framework, the ways by which this latter determination is made (either by simple comparison of the amino acid sequence, or by computer modeling of the predicted three dimensional structure of the murine antibody and matching it to the selected human framework which may in turn have amino acid changes) and the selection of the optimal final cell line to carry the DNA for the humanized antibodies. These techniques have been detailed extensively in many publications, among them: (Winters and Milstein, 1991, *Nature* 349:293–299; Riechmann et al., 1988, *Nature* 332:323–327; Hird et al., 1991, *Br. J. Cancer* 64:911–914; Gassow and Seemann, 1991, *Methods in Enzymology*, pp 99–121; Jones et al., 1986, *Nature* 321:522–525; Verhoeyen et al., 1988, *Science* 239:1534–1536; Riechmann et al., 1988, *Nature* 332:323–327; Kamman et al., 1989, *Nucl. Acids Res* 17:5404; Maeda et al., 1991, *Hum. Antibod. Hybridomas* 2:124–133.

5.3 Chimerization-humanization of murine monoclonal antibodies

Monoclonal antibodies of murine origin are humanized by various methods so as to reduce the immunogenicity of the proteins with respect to the murine immunoglobulin component. One way involves production of chimeric antibody by linking cDNA molecule encoding the V region of the murine Mab to DNA encoding the human constant region. This can be effected using several approaches described in issued patents. The chimerization procedure involves:

(1) Isolation of messenger RNA (mRNA) from mouse hybridoma cells, then cloning and cDNA production.

(2) Preparation of a full length cDNA library from purified mRNA from which appropriate variable (V) region gene fragments, of the light (L) and heavy (H) chain genes can be identified, sequenced and made compatible with a constant (C) region gene segment.

(3) Preparation of C region gene segment modules by cDNA preparation and cloning.

(4) Construction of complete H or L chain coding sequences by linkage of the cloned specific immunoglobulin V region gene segments to cloned human C region segment modules.

(5) Expression and production of chimeric L and H chains in prokaryotic and eukaryotic cells.

Detailed procedures are provided in Cabilly et al., U.S. Pat. No. 4,816,567 (28 Mar. 1989); Taniguchi et al., Eur. Patent EP 171496 (19 Feb. 1986); and Kudo et al., EP 184187 (11 Jun. 1986); and publications including Cabilly et al., 1984, *Proc. Natl. Acad. Sci., USA* 81:3273–3277; Morrison et al., 1984, *Proc. Natl. Acad. Sci. USA* 81:6851–6855; Neuberger et al., 1985, *Nature Lond.,* 314:268–270; Tan et al., 1985, *J. Immunol.,* 135:3564–3567; Sun et al., 1987, *Proc. Natl. Acad. Sci., USA* 84:214–218; Lui et al., 1987, *J. Immunol.,* 139:3521–3526; and Horowitz, 1988, *Proc. Natl. Acad. Sci. USA,* 95:8676–8682).

5.4 Selection of Ab1s

Several criteria may be used to select a preferred monoclonal antibody against an allergen to be downregulated. These include:

5.4.1 Demonstration that the selected monoclonal antibody recognizes a human IgE immunodominant protein in the allergen mixture in those cases in which the allergen is a mixture rather than a single component Many native allergens are composed of mixtures of proteins, which may number more than 20. Functionally, the majority of the human immune response which is clinically significant (IgE in the case of most aeroallergens) is directed against 1–4 of these proteins. An example is short ragweed, in which over 50% of the IgE response is directed against Amb v I (known in the earlier literature as AgE). Another example is the Lol p 1 protein in Rye grass, in which up to 80% of the IgE reacts against this protein. A third is Der p I protein and Der p II protein in dust mite allergens, in which these two proteins account for well over 50% of the IgE response.

To identify such proteins, immunoblotting may be used. In this procedure the crude antigen extract is subjected to SDS-PAGE to separate the proteins by molecular weight. Then, sera from patients clinically reactive to the given allergen mixture are overlaid onto the separated proteins, which have been electrotransferred onto nitrocellulose paper. After incubation, the strips are developed by addition of reagents such as peroxidase-labeled anti-human-IgE sera. This identifies the protein(s), and their relative contribution can be demonstrated by isolation of the proteins, and absorption of the IgE from patient's sera. Identification of an IgG immunodominant epitope may be performed using anti-human-IgG serum, see Section 8.

5.4.2 Demonstration that the selected monoclonal antibody recognizes a human IgE immunodominant epitope on the protein A range of murine or human monoclonal IgG or IgM antibodies are made by standard methods defined elsewhere in this document and well known to those skilled in the art. This panel of antibodies is used to identify the immunodominant epitope on the molecule by checking the ability of each antibody to substantially inhibit the binding of the human IgE or IgG containing sera to the protein. Substantial inhibition is at least 20%, preferably by 40%, more preferably by 50%, 60%, 75%, or even 90%. Alternatively, the ability of the human IgE or IgG containing sera to inhibit the binding of each monoclonal may be tested. In the latter case, the monoclonal antibody may be radiolabeled with $^{125}I$, mixed with the human serum, and added to polystyrene removawell strips coated with the protein. Determination of radioactivity remaining after incubation and washing of the wells will quantitate the amount of blocking, and identify immunodominant epitopes. Usually such a protein contains 2–6 immunodominant epitopes, and the monoclonal antibodies reacting with these epitopes are selected for further study.

5.4.3 Demonstration that the selected monoclonal antibody stimulates an anti-idiotype specificity similar to that induced in humans, including those receiving allergen specific immunotherapy In the case of allergens, humans subjected to hyposensitization and enjoying clinical improvement of their symptoms are available. The identification of the specificity of the auto-anti-idiotypic antibodies in the sera of these patients also aids in identification of Abs likely to be effective in down-regulation of the IgE response, since it is anticipated they will be directed against the naturally occurring Ab1 which in turn identifies the appropriate epitope for down regulation. Therefore, one approach to identify the specificity of the candidate monoclonal Ab1s is to measure their ability to inhibit binding of $^{125}I$ labeled "candidate" monoclonal antibody to the protein. In one such procedure naturally occurring polyclonal human Ab1s are removed from the sera from hyposensitized humans by absorption with the antigen, so they will not interfere with the assay. They are also absorbed with normal murine IgG coupled to Sepharose CL4B, if a murine monoclonal antibody is to be tested. The sera, now containing only AB2 antibodies against the protein in question, are then tested for the inhibition of binding of murine monoclonal anti-rye Lol p I monoclonal antibody to the antigen. The antigen is coated onto polystyrene removawell strips, and the candidate monoclonal antibody, now radiolabeled, is mixed with the absorbed human sera, or incubated alone (as the positive control). Wells are washed and measured. Reduction of radioactivity confirms the percent of inhibition, and identifies the monoclonal antibody which recognizes the specificity of the auto-anti-idiotypic antibody present in highest amount.

In general, an antibody binds at least 20%, more preferably 40%, 50%, 60%, 75% or greater of the auto anti-idiotypic antibody induced in a hyposensitization subject.

5.4.4 Demonstration that treatment of animals with the Mab significantly down-regulates the immune response against the allergen If an animal model exists, the ability of the selected monoclonal antibody(s) which may be used as a cocktail, to down-regulate the immune response may be tested. In this case, the animal may be sensitized either by injection of the allergen in adjuvant, without adjuvant, or in the aerosolized form. The candidate monoclonal antibodie(s) are then injected before or at various periods after sensitization, and their ability to down-regulate either the primary response or the response to antigen challenge is measured. In most cases tested, the response is down-regulated by at least 50%.

These criteria are used to identify the optimal antibody for down-regulation of the IgE response.

The immune response to a wide variety of antigens or antigen mixtures can be down-regulated by the appropriate Ab1. In the most complex case, native allergens which are composed of a variety of proteins, the following line of investigation will aid in selecting the appropriate Ab1:

1. Identification of the immunodominant protein(s) in the mixture.

Although many native allergens are composed of mixtures of proteins which may be greater than 20; functionally the majority of the human immune response which is clinically significant (IgE in the case of most aeroallergens) is directed against 1–4 of these proteins. An example is short ragweed, in which over 50% of the IgE response is directed against Amb v I (known in the earlier literature as AgE). Another example is the Lol p 1 protein in Rye grass, in which up to 80% of the IgE reacts against this protein. A third is Der p I protein and Der p II protein in dust mite allergens, in which these two proteins account for well over 50% of the IgE response.

To identify such proteins, immunoblotting may be used. In this procedure the crude antigen extract is subjected to SDS-PAGE to separate the proteins by molecular weight. Then, sera from patients clinically reactive to the given allergen mixture are overlayed onto the separated proteins, which have been electrotransferred onto nitrocellulose paper. After incubation, the strips are developed by addition of reagents such as peroxidase-labelled human anti-IgE sera. This identifies the protein(s), and their relative contribution can be demonstrated by isolation of the proteins, and absorption of the IgE from patient's sera.

2. The immunodominant epitope(s) are then identified on the relevant protein:

A range of murine or human monoclonal IgG or IgM antibodies are made by standard methods defined elsewhere in this document and well known to those skilled in the art. This panel of antibodies is used to identify the immunodominant epitope on the molecule by checking the ability of each antibody to substantially inhibit the binding of the human IgE containing sera to the protein. Alternatively, the ability of the human IgE containing sera to inhibit the binding of each monoclonal may be tested. In the latter case, the monoclonal antibody may be radiolabeled with $^{125}I$, mixed with the human serum, and added to polystyrene removawell strips coated with the protein. Determination of radioactivity remaining after incubation and washing of the wells will quantitate the amount of blocking, and identify immunodominant epitopes. Usually such a protein contains 2–6 immunodominant epitopes, and the monoclonal antibodies reacting with these epitopes are selected for further study.

3. In the case of allergens, humans subjected to hyposensitization and enjoying clinical improvement of their symptoms are available. The identification of the specificity of the auto-anti-idiotypic antibodies in the sera of these patients also aids in identification of Ab's likely to be effective in down-regulation of the IgE response, since it is anticipated they will be directed against the naturally occurring Ab1 which in turn identifies the appropriate epitope for down regulation. Therefore, one approach to identify the specificity of the candidate monoclonal Ab1's is to measure their ability to inhibit binding of $^{125}$I labeled "candidate" monoclonal antibody to the protein. In one such procedure naturally occurring polyclonal human Ab1's are removed from the sera from hyposensitized humans by absorption with the antigen, so they will not interfere with the assay. They are also absorbed with normal murine IgG coupled to Sepharose CL4b, if a murine monoclonal antibody is to be tested. The sera, now containing only AB2 antibodies against the protein in question are now tested for the inhibition of binding of murine monoclonal anti-rye Lol p I monoclonal antibody to the antigen. The antigen is coated onto polystyrene removawell strips, and the candidate monoclonal antibody, now radiolabeled, is mixed with the absorbed human sera, or incubated alone (as the positive control), and wells are washed and the reduction of radioactivity confirms the percent of inhibition, and identified the monoclonal antibody which recognizes the specificity of the auto-anti-idiotypic antibody present in highest amount.

4. If an animal model exists, the ability of the selected monoclonal antibody(s) which may be used as a cocktail, to down-regulate the immune response may be tested. In this case, the animal may be sensitized either by injection of the allergen in adjuvant, without adjuvant, or in the aerosolized form. The candidate monoclonal antibodie(s) are then injected before or at various periods after sensitization, and their ability to down-regulate either the primary response or the response to antigen challenge is measured. In most cases tested, the response is down-regulated by at least 50%.

Obviously, if the clinically important allergen has only one protein, such as ovalbumin in chicken egg white or parvalbumin in cod fish, both of which induce an IgE reaction, or casein in cow's milk which induces an IgG reaction, or if the clinically significant allergen has only one epitope such as urushiol which induces a T cell response, this selection procedure may be shortened.

6. Example: Ab1s to dust mite allergens 6.1 Dust mite allergens

Dust mite allergy is responsible for a range of allergic diseases, principally asthma, allergic rhinitis and probably atopic dermatitis. Although these diseases can also be produced by a variety of other allergens, such as pollens, dust mite ranks as one of the top three offenders. The allergy is caused by exposure to mites of the genus Dermatophagoides, particularly *Dermatophagoides pteronyssinus* (Der p) and *Dermatophagoides farinae* (Der f). These mites are found worldwide, in house dust, mattresses, rugs, etc. so they produce symptoms year round. A range of at least 24 different proteins has been identified although Der I (molecular weight 24,000) and Der II (molecular weight 15,000) are generally recognized as the major mite allergens. These proteins have been sequenced and cloned, and it is now possible to determine which epitopes are responsible for reaction with T cells and IgE antibodies. There is considerable homology between the Der I antigens, and the Der II antigens, so that both species of dust mite produce similar symptoms, even though geographically one may dominate over the other. Individuals sensitized to dust mite allergens such as *D. pteronyssinus* produce IgG, IgA, and IgE antibodies. These persist in atopic individuals and correlate with allergic symptoms. Although multiple subclasses of antibody may be produced, it is the IgE levels that are associated with allergic diseases. Hyposensitization, one of the main methods of therapy against these diseases, results in an increase in IgG levels and a decrease in IgE levels; this is correlated with a decrease in symptoms.

6.2 Dust mite preparations

Whole dust mite preparation from *Dermatophagoides pteronyssinus* or *Dermatophagoides farinae* (DMA) including mite bodies, faeces and culture medium (10 gm) is added to phosphate buffered saline pH 7.3, (100n-d) and stirred overnight at 4° C. The resultant mixture is centrifuged at 100,000 g for 1 hour. Supernatant is removed and precipitated with 50% saturated ammonium sulfate. The sediment is removed by centrifugation at 4,000 rpm for 15 minutes, and resuspended in phosphate buffered saline pH 7.3 (PBS). This preparation is dialyzed against PBS (4 changes of 4 liters over 48 hours), and the product stored at −20° C. (DMA). Its composition is characterized by SDS PAGE analysis. The concentrations of Der p I protein is determined by immunoassay, compared to standards provided by Dr. Martin Chapman, University of Virginia, Charlottesville, USA (Luczinska et al., 1989, *J. Immunol. Methods* 118:227–2359).

6.2.1 Purified Group I Mite Allergens

Der p I and Der f I preparations are isolated from DMA extracts of the appropriate mites by affinity chromatography on insolubilized anti-Der II monoclonal antibody (for example, 1114/2F10—Table 1: 7AI, Lombarders et al, 1990, *J. Immunol.* 144:1353–1360, 1990. In an example, murine monoclonal antibody 1114/2F10 (50 mg) is coupled to cyanogen bromide activated Sepharose 4B. Dust mite extract is applied to the column containing 1114/2F10 Mab-Sepharose 4B and non-bound material eluted by extensive washing with PBS. The bound product is then eluted with 0,005 M glycine in 50% ethylene glycol pH 10. The eluted product is precipitated with 50% ammonium sulphate, re-dissolved in PBS and dialysed against several changes of 2L PBS. The final product is stored at −70° C.

6.2.2 Purification of Group II Mite Allergens

Der p II and Der f II preparations are isolated from DMA extracts of the appropriate mites by affinity chromatography on insolubilized anti-Der II monoclonal antibody (for example, 1114/2F10—Table 1: 7AI; Lombardero et al., 1990, *J. Immunol.* 144:1353–1360). In an example, murine monoclonal antibody 1114/2F10 (50 mg) is coupled to cyanogen bromide activated Sepharose 4B. Dust mite extract is applied to the column containing 1114/2F10 LUB-Sepharose 4B and non-bound material eluted by extensive washing with PBS. The bound product is then eluted with 0.005M glycine in 50% ethylene glycol pH 10. The eluted product is precipitated with 50% ammonium sulphate, re-dissolved in PBS and dialysed against several changes of 2L PBS. The final product-is stored at −70° C.

6.3 Production of murine anti Der p and anti Der f monoclonal antibodies 6.3.1 Immunization protocol BALB/c mice are immunized according to the following schedule: 25 g DMA in Freund's complete adjuvant (FCA), delivered intraperitoneally, as the initial immunization (Day 0) then, at various intervals, between days 9 and 56, they are again injected with 25 g DMA in incomplete Freund's adjuvant (IFA), intraperitoneally, two to four times. Usually 3 days prior to sacrifice 25 g is injected DMA in PBS, intravenously. Mice are killed on days 45 to 60, and single cell suspensions of the spleen are prepared and fused with mouse myeloma NSO cells by established procedures known to those skilled in the art (Embleton et al., BR., *J. Cancer*, 43:582–587, 1981; Kohler and Milstein, *Nature*, 256:495–497, 1975; U.S. Pat. No. 4,376,110).

6.3.2 Hybridoma selection protocol

Hybridomas are selected by screening of culture supernatants for antibody reacting with a PBS extract of dust mite preparations (DMA) by an ELISA test (ELISA and Other Solid Phase Immunoassays Eds., D. M. Kemeny and S. J. Challacombe 91988) (Wiley). Briefly polyvinyl microtiter plates (Falcon MICROTEST III or the like) are coated with the equivalent of 0.5 g/well Der p I by overnight incubation of a dust mite preparation (DMA). To reduce non-specific antibody binding due to uncoated reactive sites in wells, the microtiter plates are blocked with casein in tris-buffer pH 7.3. Tissue culture supernatant is added to the microtiter plate wells for 45 minutes, then excess removed by washing in PBS. Peroxidase conjugated rabbit antibody to mouse immunoglobulin is added and bound antibody detected by color formation following addition of substrate 2,2'-azino-di-(3 ethylbenzthiazoline sulfonic acid) (ABTS). Hybridomas selected in the primary screen are cloned two times and hybridoma lines established. Monoclonal antibodies (Mabs) from cloned hybridomas are purified by various procedures and further characterized. Immunoblotting with Mab purified from hybridoma supernatents is carried out in which Der p extract is subjected to SDS-PAGE followed by transfer to nitrocellulose and subsequent staining with Mab (Thompson et al., 1988, J. Immunol. 64:311–314. By comparison with standard (eg, Der p I) this allows components of the Der p extract reacting with the Mab to be identified. The characteristics of selected Mabs in comparison with other anti-dust mite antibodies is further established using a blocking assay. In this procedure the Mab under investigation is added to microtiter plates coated with dust mite extract (DMA) so blocking antigen sites. Inhibition of the binding of defined antibodies such as anti Der p I antibody 5H8 (Chapman et al., J. Immunol, 139: 1479–1484, 1987) indicates that the Mab under test recognizes the same or closely related epitopes on DMA to the standard antibody. To measure inhibition of Mab binding, biotinylated Mab is added to the blocked microtiter plates and bound antibody is detected by addition of streptavidin-proxidase conjugates, followed after washing by the substrate (ABTS).

The ability of murine Mabs to inhibit binding of antibodies in serum of patients sensitized to dust mite allergens is similarly detected by a blocking assay. In these tests, the Mab under investigation is added to microtiter plates coated with dust mite extract. Inhibition of the binding of patients serum is then detected by first adding patients serum to microtiter plates, washing and detection of bound human Ig with goat-antihuman Ig peroxidase conjugate followed by substrate (ABTS).

6.3.3 Anti-idiotypic antibody response to murine anti-Der p and anti-Der f monoclonal antibodies Murine anti-idiotypic antibodies to monoclonal antibodies are produced by immunizing inbred BALB/C mice with monoclonal antibodies coupled to keyhole limpet hemocyanin together with Freund's complete, then incomplete, adjuvant. In an example, BALB/C mice are immunized first with Mab-KLH (50 µg) incomplete Freund's adjuvant and then twice at two week intervals with Mab-KLH (50 µg) in incomplete adjuvant. Antisera are then obtained 7 to 14 days later as a source of antibodies used to define the idiotypes of anti-Der p I monoclonal antibodies 2C7 (Table 2) and 4C1 (Chapman et al., 1987, J. Immunol. 139:1479–1484). Binding of Mab 2C7 to Der p I is detected by radio-immunoassay using $^{125}$I labelled Mab 2C7. Inhibition of this binding by a range of anti-idiotypic antibodies is detected by mixing $^{125}$I labelled Mab 2C7 with antiserum before addition to microliter plates coated with Der p allergen. Binding of 2C7 is inhibited only by anti-idiotypic antibody to 2C7. Binding of 4C1 to Der p I is only inhibited by anti-idiotypic antibody to 4C1. These findings show that although Mabs 2C7 and 4C1 recognize closely related epitopes on Der p I they possess separate and distinct idiotypes.

6.4 Murine anti-der p hybridoma cell lines

6.4.1 Mab 1102/H11

The Mab is obtained from culture supernatants of hybridoma 1102/H11 cells maintained in RPMI 1640 medium supplemented with 10% fetal calf serum. Mab 1102/H11 is purified by affinity chromatography on Sepharose protein G (Pharmacia) and isotype analysis established the antibody to be immunoglobulin IgG1.

The reactivity of 1102/H 11 with dust mite-associated antigen has been established by ELISA assay of its binding to a DMA preparation. Further characterization by immunoblotting against Der p proteins after SDS PAGE and transfer to nitrocellulose indicated Mab 1102/H11 reacts with a 24 kDa component equivalent to that detected murine Mab 5H8 (clone 5H8 C12 D9) which binds to an epitope on Der p I (Chapman et al., J. Immunol., 139:1479–1484, 1987).

Figure 4:
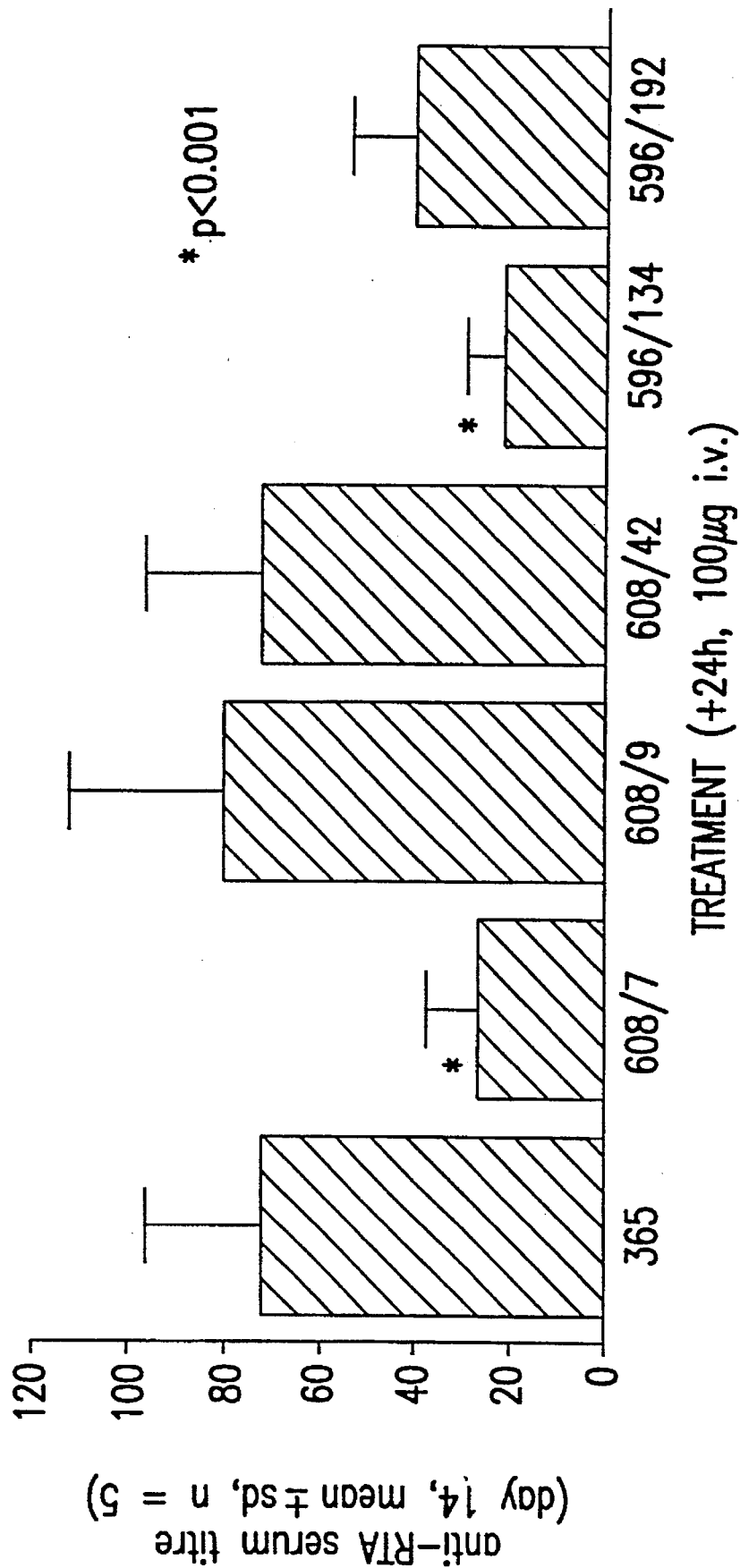

The blocking assay was used to further investigate the relationships between dust mite antigen epitopes reacting with Mabs 1102/H11 and 4Cl. This is illustrated in FIG. 4 which shows that Mab 1102/H11 inhibited binding of biotinylated 4Cl to dust mite extract (DMA). These findings confirm that MA B 1102/H11 reacts with a der p epitope identical to, or closely related to the epitope recognized by Mab 4C1 (Chapman et al., J. Immunol., 139:1479–1484, 1987).

Table 3 lists human monoclonal antibodies produced by hybridomas formed by fusion of human lymphocytes from tonsils or peripheral blood with a human-mouse heteromyeloma.EL 41.

TABLE 3

Human Anti-dust Mite Monoclonal Antibodies
ELISA OD on Plates Coated with:

| Hybridoma | Lymphocyte Donor[1] | DMA[2] | Casein | Reactivity with: Der p I | Der p II[3] |
|---|---|---|---|---|---|
| DM27 1E11 |  | 0.196 | 0.049 | + | − |
| DM27 1A11 | Tonsil | 0.065 | 0.000 | − | + |
| DM27 1F10 |  | 0.094 | 0.000 | − | + |
| DM27 2G9 |  | 0.111 | 0.000 | + | − |
| DM28 1D11 |  | 0.160 | 0.019 | + | − |
| DM28 2A2 | PBL | 0.172 | 0.043 | − | + |
| DM28 2E9 |  | 0.391 | 0.176 | + | − |
| DM31 1H2 |  | 0.138 | 0.072 | − | + |
| DM31 1G7 | Tonsil | 0.179 | 0.096 | + | − |
| DM31 2B2 |  | 0.191 | 0.000 | + | − |
| DM31 2C10 |  | 0.202 | 0.000 | + | − |

6.4.2 Mab 1107/2B11

Antibody is obtained from culture supernatants of hybridoma 1107/2B I 1 which is maintained in RPMI 1640 medium supplemented with 10% fetal calf serum. Mab 1107/2BII is purified by affinity chromatography on Sepharose protein G (Pharmacia) and isotype characterized to establish the antibody to be added. Characterization of the dust mite antigen reactivity by immunoblotting after SDS PAGE and transfer to nitrocellulose indicated that it reacts with a protein with a molecular weight of 27 kDa.

6.4.3 Other murine anti-dust mite Mab

Similar procedures have been used to produce a range of murine Mab reacting with dust mite Der p and Der f antigens (Table 1).

TABLE 1

| Mab | Isotype | Allergen | Mw |
|---|---|---|---|
| 1102/H11 | IgG1 | Der pI | 24000 |
| 1107/2B11 | IgG1 | Der pI | 27000 |
| 1111/A2 | IgG1 | Der pI | 24000 |
| 1114/1F7 | IgG2a | Der pI | 24000 |
| 1114/2F10 | IgG2a | Der pII | 15000 |
| 1119/1C12 | IgM | ND | 27000 |

6.5 Selection of murine anti-Der p Mab for down-regulating immune responses to Der p I and Der p II allergens An additional series of anti-dust mite monoclonal antibodies have been selected which are capable of down-regulating the allergic response to dust mite. These monoclonal antibodies are directed against Der p I and Der p II, the two major allergens in dust mite (Table 2). Those monoclonal anti-Der p I and Der p II antibodies also cross-react with Der f I and Der f II, and so are useful for regulating allergic responses to allergies in either *Dermatophagoides pteronyssinus* or *Dermatophagoides farinae.*

The selected Mabs also recognize immunodominant regions of the allergens as determined by their capacity to block interaction of serum IgE antibodies to either Der p I or Der p II. Data obtained using Mab 2C7 directed against Der p I provide an example of antibody selection, characterization and assessment.

6.5.1 Anti Der p I Mab 2C7

Anti-Der p I Mab 2C7 was produced as described in section 6.3, and purified from hybridoma culture supernatants by Sepharose-protein A affinity chromatography. This Mab (isotype $IgG_{2b}$) reacts with Der p I and Der f I (Table 2) as demonstrated by ELISA assay (described in section 6.3.2).

In previous studies reported by Chapman and associates (Chapman et al., *J. Immunol.* 139:1479–1484, 1987), murine Mab 4C1 was shown to react with an immunodominant epitope on Der p I since it blocked up to 40% of the binding of serum IgE to Der p I. Also, Mab 4C1 is cross-reactive with epitopes on Der p I and Der f I. The close relationship of the Der p I epitope reacting with Mab 2C7 and 4C1 was demonstrated using cross-blocking assays. In this procedure ELISA microtiter plates coated with dust mite extracts are incubated with a range of concentrations of Mab 2C7. After washing, binding of Mab 4C1 is determined using biotin-labeled Mab 4C1. In this assay biotinylated Mab 4C1 is detected using streptavidin-conjugated horse radish peroxidase. Using this inhibition assay, it was shown that Mab 2C7 completely blocked the antigen sites on Der p I which react with Mab 4C1 (FIG. 9). These findings indicate that the epitopes on Der p I recognized by Mabs 2C7 and 4C1 are identical or closely related. In comparison, anti-Der p I Mab H11 (Table 1) was unable to block the binding of biotinylated Mab 4C1 to Der p I. Mab H11 therefore recognizes a Der p I epitope unrelated to that reacting with Mab 4C1.

6.5.2 Mab idiotype characterization

To further explore the relationship of Mab 2C7 and 4C1 binding epitopes, the idiotypes of these two Mabs were defined. Polyclonal anti-idiotypic

TABLE 2

Reactivity of Anti-Dust Mite Monoclonal Antibodies

| Monoclonal Antibody | Reactivity (ELISA OD 405 nm) with: | Der f I | Control[1] |
|---|---|---|---|
| | Der p I | | |
| 2C7 | 0.56 | 0.44 | 0.05 |
| 4C1* | 0.60 | 0.33 | 0.04 |
| H11 | 0.43 | 0.39 | 0.04 |
| 337** | 0.07 | 0.05 | 0.02 |
| | Der p II | | |
| 2H5 | 0.70 | 0.09 | |
| 6D6* | 0.60 | 0.07 | |
| 337** | 0.09 | 0.04 | |

[1]ELISA plate wells uncoated

*Mab provided by Dr. M. Chapman, Division of Allergy and Clinical Immunology, University of Virginia, Charlottesville, Virginia, USA

**Control Mab anti-carcinoembryonic antigen provided by Prof. R. W. Baldwin, Cancer Research Campaign Laboratories, University of Nottingham, Nottingham, UK antibodies were produced to a range of murine anti-Der p I monoclonal antibodies (4C1, 2C7, 5H8), anti-Der p II Mab (6D6) and control Mab 337 (anti-carcinoembryonic antigen, CEA). These polyclonal anti-idiotypic antisera were produced by immunizing BALB/c mice with Mabs conjugated to keyhole limpet hemocyanin (KLH) in complete and then incomplete Freund's adjuvant.

Anti-idiotypic anti-sera were assayed for the capacity to inhibit binding of anti Der p I Mabs (2C7, 4C1, and 10B9) to Der p I. In this assay various dilutions of polyclonal anti-idiotypic anti-sera were mixed and incubated with $^{125}$I-labeled murine monoclonal antibody so as to allow reaction with the Mab. The mixture was then added to ELISA microtiter plates coated with Der p I and reaction determined by radioimmunoassay. As shown in FIG. 10, anti-Mab 2C7 serum completely inhibited binding of 2C7 to Der p I. In contrast anti-4C1 serum did not produce any inhibition of 2C7 binding to Der p I. These findings indicate that Mabs 2C7 and 4C1 recognize closely related but non-identical Der p I epitopes.

6.5.3 Relationship between Der p I epitopes inducing human IgE antibodies and those reacting with murine Anti-Der p I Mabs In selecting murine Mabs for down-regulating human IgE reactivity to Der p I (and Der p II) a useful criterion is that both antibody species react with the same allergen epitope. Also the dust mite allergen epitope preferably should be an immunodominant component accounting for a major component i.e., 25% or greater, preferably at least 40%, 50%, or 60% of the human IgE response. For greater general clinical utility as a therapeutic, a preferred monoclonal antibody should exhibit greater than 40% inhibition of IgE binding to the allergen in a majority of human subjects. This has been demonstrated with a range of anti-Der p I Mab by experiments showing that they block up to 80% of the binding of serum IgE antibody to Der p I (FIG. 11).

In these tests, serum from 6 atopic dermatitis subjects with high levels of serum IgE antibodies to Der p I were examined. Serum samples, diluted to a level giving sub-saturating amounts of IgE antibody binding to Der p I coated ELISA microtiter plates, were mixed with murine Mab (100 μg). This mixture was added to Der p I-coated microtiter plates. After incubation overnight at 4° C. bound human IgE was detected by ELISA using goat anti-human IgE-horse radish peroxidase conjugate. As shown in FIG. 11, Mab 2C7 was the most effective of the four anti-Der p I Mabs in inhibiting binding of human serum IgE to Der p I. With this Mab, at least 50% of serum IgE binding was obtained with 5 of 6 patient serum samples tested. The maximum inhibition obtained was 80%, with serum from patient A368. In comparison, greater than 40% inhibition of serum IgE binding was only obtained with 1/6 serum samples using murine Mab 4C1 (Chapman et. al. *J. Immunol.* 139:1479–1484, 1987).

6.5.4 Identification of idiotypes of Mab 2C7 and Human anti-Der p I IgE Antibody In selecting monoclonal antibodies to dust mite allergens for therapy, a significant criterion is that the idiotype of the selected Mab is identical, or closely related, to the idiotype of human IgE antibodies. To establish this with Mab 2C7, IgE antibodies from serum of atopic dermatitis patients were captured on ELISA microtiter plates coated with goat anti-human IgE antiserum as described in the protocol infra. The reactivity of bound human IgE was then determined with a range of polyclonal anti-idiotypic antibodies produced against murine anti-Der p I Mabs. As summarized in Table 4, polyclonal mouse anti-idiotypic antibodies to Mab 2C7 reacted with all six IgE preparations from serum of atopic dermatitis patients with high anti-Der p I antibody levels. In comparison, none of the IgE samples bound to anti-idiotypic antisera raised against Mab 4C1. These observations indicate that the idiotype of Mab 2C7 is closely related to that of human IgE. This supports the algorithm for choice of a therapeutic antibody, which indicates that stimulation of anti-idiotypic immune responses to Mab 2C7 is appropriate for immunoregulation of Der p I allergy

TABLE 4

Binding of Anti-Idiotypic Antibodies
Produced Against Mouse Anti-Der p I
Monoclonal Antibodies to Serum IgE
from Atopic Dermatitis Patients*
Binding (ELISA, OD 405 nm) of anti-idiotypic antibody to:

| Serum IgE from Patient | Mab 4C1 | Mab 2C7 | Normal Mouse Serum |
| --- | --- | --- | --- |
| 1 | 0 | 1.03 | 0 |
| 2 | 0.1 | 1.03 | 0 |
| 3 | 0.04 | 1.0 | 0 |
| 4 | 0.02 | 1.0 | 0 |
| 5 | 0.03 | 1.08 | 0 |
| 6 | 0.05 | 0.87 | −0.1 |
| 7 | 0.04 | 0.72 | 0 |

*Microtiter plates are coated with goat anti-human IgE, and patient sera are added to allow capture of anti-Der p IgE. Binding of polyclonal mouse antibody produced against murine Mab determined by ELISA (OD 405 nm)

6.6 Chimerization-humanization of murine monoclonal antibodies

Monoclonal antibodies of murine origin are humanized by various methods so as to reduce the immunogenicity of the proteins with respect to the murine immunoglobulin component. One way involves production of chimeric antibody by linking cDNA molecule encoding the V region of the murine Mab to DNA encoding the human constant region. This can be effected using several approaches described in patents [Cabilly et al., U.S. Pat. No. 4,816,567 (28 Mar., 1989); Taniguchi et al., Eur. Patent EP 171496 (19 Feb. 1986) and Kudo et al., Eur. Patent EP 184187 (11 Jun., 1986)] and publications including Cabilly et al. *Proc. Natl. Acad. USA*, 81:3273–3277, 1984; Morrison et al., *Proc. Natl. Acad. Sci., USA*, 81:6851–& 55, 1984; Neuberger et al., *Nature*, Lond., 314:268–270, 1985; Tan et al., *J. Immunol.*, 135:3564–3567, 1985; Sun et al., *Proc. Natl. Acad. Sci., USA*, 84:214–218, 1987; Lui et al., *J. Immunol.*, 139:3521–3526, 1987 and Horowitz, A. H. *Proc. Natl. Acad. Sci., USA*, 95:8676–8682, 1988. The chimerization procedure involves:

(1) Isolation of messenger RNA (mRNA) from mouse hybridoma cells, then cloning and cDNA production.

(2) Preparation of a full length cDNA library from purified mRNA from which appropriate variable (V) region gene fragments,; of the light (L) and heavy (H) chain genes can be identified, sequenced and made compatible with a constant (C) region gene segment.

(3) Preparation of C region gene segment modules by CDNA preparation and cloning.

(4) Construction of complete H or L chain coding sequences by linkage of the cloned specific immunoglobulin V region gene segments to cloned human C region segment modules.

(5) Expression and production of chimeric L and H chains in prokaryotic and eukaryotic cells.

6.7 CDR grafting

Humanized monoclonal antibodies containing only murine variable regions and constructed by CDR grafting/reshaping using various techniques (Winters and Milstein, *Nature*, 349:293–299, 1991; Riechmann et al., *Nature*, 332:323–327, 1988-, Hird et al., *Br. J. Cancer*, 64:911914, 1991; Gussow and Seemann, *Methods in Enzymology*, 99–121, 1991). The complementary determining regions (CDRS) of a murine Mab are transplanted onto the corresponding regions in a human antibody. The CDRs (three in antibody heavy chains and three in light chains) are the regions of the murine Mab which bind to the antigen epitope. Transplantation of the CDRs is achieved by manipulation whereby CDR DNA sequences are determined by cloning of murine heavy and light chain variable (V) region gene segments and transfer to corresponding human V regions by site-directed mutagenesis. Human constant region gene segments of the desired isotype are added and the humanized heavy and light chain genes are co-expressed in mammalian cells to produce humanized antibodies.

A general procedure has been developed to graft CDRs from rodent monoclonal antibodies onto human FRs to make fully humanized antibodies or antibody fragments using PCR methodology (A. P. Lewis and J. S. Crowe, *Gene*, 1991, 297–302). PCR primers which bind to the FR regions bracketing the CDRs have been developed; these permit amplification of the CDR from hybridoma cells secreting the Mab of interest. The PCR product is cloned and sequenced, and joined to the framework and constant regions of choice.

7. Example: production of human anti-Der p monoclonal antibodies

Human monoclonal antibodies reacting with Der p antigens are produced by various procedures. These include immortalization of antibody-producing cells from human donors sensitive to DMA by construction of human hybridomas or human-mouse heterohybridomas using techniques well known to those versed in the art (Austin et al., *Immunology*, 67:525–530, 1989) or by Epstein Barr virus transformation (Roder et al., *Meth. in Enzymology*, 121:140–167, 1986). Human antibodies are also obtained by repertoire cloning (Marks et al., *J. Mol. Biol.*, 222:581–597, 1991; Persson et al., *Proc. Natl. Acad. Sci.*, 88:2432–2436, 1991; Huse et al., Science, 246:1275–1281, 1989; Kang et al., *Proc. Natl. Acad. Sci, USA*, 80:4363–4366; Duchosal et al., *Nature*, 355:258–262, 1992).

7.1 Hybridoma Production

Lymphocytes are obtained from various tissues including peripheral blood, tonsils and spleen from human subjects sensitized to dust mite. Cell preparations are obtained by FICOLL/HYPAQUE density centrifugation and fused immediately after separation or following in vitro stimulation. Various in vitro stimulation methods are used including treatment of lymphocytes cultured in medium RPMI 1640 with dust mite extracts. In some cases in vitro culture conditions include immunological adjuvants such as adjuvant peptide (N-acetylmuramyl-L-alanyl-D-isoglutamine, Sigma).

7.1.1 Fusion Protocol

Mouse/human heteromyeloma EL41 cells (deposited on May 16, 1990 with the European Collection of Animal Cell Cultures and having Accession No. 90051602) as described by Austin et al., *Immunology*, 1989, 67:525–530, are fused with human lymphocytes reactive with dust mite antigen using polyethylene glycol according to the method of Galfre et al., *Nature*, 1977, 266:550. For example, lymphocytes are placed in 30 ml plastic universal bottles and washed twice with growth medium such as RPMI 1640 and the number of lymphocytes determined by haemocytometer counting. EL41 cells are harvested, washed and counted in a similar fashion. The two cell populations are then mixed at a lymphocyte:fusion partner ratio of 2:1 and washed for a third time. Following centrifugation the medium is discarded and 0.8 ml of 50% PEG pipetted over a 1 minute period onto the cell pellet with gentle agitation. The mixture is left for one minute then 1.0 ml of medium added over a further 1 minute period followed by the addition of 20 ml of medium added slowly over a 5 minute period. The cells are then centrifuged at 1200 rpm for 5 minutes, the medium discarded, and the cells resuspended by gentle pipetting in a 2 n-d pipette. Twenty ml of selection medium (RPMI 1640+10% FCS+$10^{-4}$M hypoxanthine, $10^{-5}$M methotrexate and $1.6\times10^{-6}$M thymidine) is finally added to the cell suspension and the cells aliquoted into two 96 well tissue culture microtiter plates containing mt peritoneal exudate cells ($2.5\times10^3$/well) as a feeder layer. An additional 1001 of media is also added to each well. The selection medium is changed every 72 hours, until resulting hybridomas have reached 50% confluence then every 48 hours. The growth of the hybridomas is regularly checked and when the colonies have covered 50% of the well the supernatant is analyzed for Ig reactive with dust mite antigen. Hybridomas producing Ig of interest are immediately cloned. Established hybridomas are frozen down in aliquots of $2-5\times10^6$ cells in 1 ml of 95% FCS and 5% Dimethyl sulfoxide (DMSO) and stored in liquid nitrogen.

7.1.2 Lymphocyte Preparation

Peripheral blood lymphocytes are prepared by diluting heparinized blood 1:2 v/v with balanced salt solution and centrifugation over lymphocyte separation medium (Flow Laboratories, Irvine, Scotland).

Lymphocytes are prepared from tonsil or spleen by teasing chopped tissue through a 120 gauge grid into balanced salt solution. After washing, the lymphocytes are counted, viability being assessed by Trypan blue dye exclusion.

7.1.3 In vitro stimulation i. Adjuvant peptide (N-acetylmuramyl-L-alanyl-D-isoglutamine, Boss, *Brain Res.*, 1984, 291:193) and dust mite preparation.

Lymphocytes ($2\times10^6$/ml) are cultured up to 5 days with adjuvant peptide (10 g/ml) and dust mite antigen (5 g/ml) in medium RPMI 1640 containing 10% fetal calf serum. The lymphocytes are then fused immediately with the fusion partner heteromyeloma EL41 (Austin et al., *Immunology*, 1989, 67:525–530).

ii. Pretreatment with L-Leucyl-L-leucine-methyl ester.

Treatment of lymphocyte preparations with L-Leucyl-L-leucine-methyl ester eliminates large granular lymphocytes, macrophages, C7L precursors and effectors, some CD8+ suppressor T cells and NK cells. It is used to enhance the in vitro immunization procedure for the production of human monoclonal antibodies (Borrebaeck et al., 1988, *Proc. Natl. Acad. Sci. USA.*, 85:3995). Briefly, lymphocytes are cultured for 15 mins at room temperature in medium RPMI 1640 containing 250M L-Leucyl-L-leucine-methyl ester. The cells are then washed and cultured for 2–8 days in medium RPMI 1640 supplemented with 10% human AB serum, 50M 2-mercaptoethanol, 5IU recombinant interleukin 2 (rIL2), 25% v/v supernatant from irradiated human T cells stimulated with pokeweed mitogen (PWM) (24 hr culture) and dust mite antigen 5–100 ng/ml. Recombinant IL4 (50U) and rIL6 (100U) is also added to some cultures as an extra lymphokine boost.

Following stimulation lymphocytes are fused with the heteromyeloma EL41.

iii. In vitro primed splenocytes (Boerner et al., 1991, *J. Immunol.* 147:86–95)

Splenocytes from two donors are mixed at equal concentrations and cultured $3\times10^6$/ml in RPMI 1640 medium containing 10% FCS and dust mite antigen 1-log/mi for 2–5 days. The lymphocytes are then fused with the fusion partner heteromyeloma EL4I.

7.2 Hybridoma Selection

Hybridomas are selected by screening of culture supernatants for antibody reacting with dust mite antigen (DMA) preparations (see section 6.3.2) using ELISA. Briefly polyvinyl microtiter plates (Falcon MICROTEST III or the like) are coated with dust mite preparation containing the equivalent of 0.5 g/well Der p 1. To reduce non-specific antibody binding to uncoated surface sites in wells, microtiter plates are blocked with casein in tris-saline buffer pH 7.3. Hybridoma supernatant is added to the wells for 45 minutes, then excess removed by washing in PBS. Peroxidase conjugated rabbit antibody to human immunoglobulin is added and bound antibody detected by color formation following addition of substrate (ABTS). Hybridomas selected in the primary screen are cloned two times and hybridoma lines established using culture procedures for stable growth. Hybridoma cell preparations of the initial fusion product and cloned lines are preserved by freezing and storing in liquid nitrogen.

Monoclonal antibodies are purified by various procedures and are characterized. Immunoblotting is carried out in which Der p and Der f extracts are subjected to SDS PAGE followed by transfer to nitrocellulose and subsequent staining with Mab (Thompson et al., *Immunol.*, 64:311–314, 1988; Chapman et al., *J. Immunol.*, 139:1479–1484, 1987; Platts-Mills and Chapman, *J. Allergy Clin. Immunol.*, 80:755–775, 1987) so as to define the molecular weights of the dust mite allergens bound by each Mab.

The relationship of human Mab to antibodies produced in human subjects sensitized to dust mite allergens is detected using several immunoassays well known to those versed in the art (as an example Didierlaurent and Garcelon *J. Immunol. Meth.* 145:22–41, 1991). In one approach microtiter plates (Chapman et al., *J. Immunol.* 139:1479–1484, 1987) or cyanogen-bromide activated paper discs (Didierlaurent and Garcelon, *J. Immunol. Meth.* 145:33–41, 1991) are coated with dust mite extract. Serum from allergic donors is incubated in the microtiter wells or discs and after washing inhibition of the reactivity with the human Mab detected. For this purpose, Mab is conjugated to biotin by well established methods. The inhibition of binding of biotinylated Mab in microtiter wells or discs is then determined by incubation first with streptavidin-biotin-peroxidase conjugate (Amersham, UK) and then with o-phenylenediamine (OPD).

7.3 Epstein-Barr Virus Transformation

Epstein Barr virus (EBV) is a herpes virus which selectively infects human B lymphocytes expressing the CR2 complement receptor. Infection in vitro of B lymphocytes leads to permanent stimulation of cell growth, with the preservation of B cell characteristics such as immunoglobulin secretion (Roder et al., *Methods in Enzymology*, 121:140–174, 1986). For EBV transformation tissue culture supernatant obtained from the marmoset cell line B95-8 is used. This cell line when cultured in Standard RPMI 1640 medium with 10% FCS, releases large quantities of virus.

Tissue culture supernatant is taken from B95-8 cells grown to confluence, this is then used at a dilution of ½ to ¹⁄₁₀ in RPMI 1640 with 10% FCS to infect human lymphocytes ($2 \times 10^6$/ml). The cells are incubated for 2 hours at 37° C. then washed and cultured in RPMI 1640 with 10% FCS or cultured without washing for 24–48 hours after which time a 50% medium change is performed every 3–4 days. The cells are cultured in costar plates or U bottom microtitre plates ($10^4$/well). Irradiated mouse spleen cells or human peripheral blood mononuclear cells can be used as a feeder layer.

7.4 Repertoire Cloning

Antibodies reacting with Der p and Der f allergens were produced by procedures based upon antigen selection from a combinatorial library and cloned (Orlandi et al., *Proc. Nat. Acad. Sci.* 86.:3833–3837, 1989; Persson et al., *Proc. Nat. Acad. Sci. U.S.A.* 88:2432–2436, 1991; Kang et al., *Proc. Nat. Acad. Sci. U.S.A.* 88:4363–4366; Duchosal et al., *Nature* 355:258–262, 1992; Clackson et al., *Nature* 352:624–628, 1991; Marks et al., *J. Mol. Biol.* 222:581–597, 1991). The general approaches well known to those versed in the art include extraction of messenger RNA (mRNA) from human lymphocytes derived from various tissues including peripheral blood (PBL), tonsillar tissue (Ton-Ly) and spleen (Spl-Ly). The lymphocytes may be derived from human allergic subjects and in addition may be initially stimulated by exposure to allergens and immunological adjuvants as already described. Another procedure for stimulating lymphocytes involved injecting PBL, Ton-Ly etc into severe combined immune deficiency (SCID) mice and stimulation of injected mice with allergen preparations such as the whole dust mite extracts (DMA) or purified proteins such as Der p I and Der p II. Mice may also be treated with immunological adjuvants such as bacillus Calmette Guerin (BCG) or by combining immunogen preparations (Der p I/II etc) with aluminium hydroxide gel, variously described as adjuvant alum.

The polymerase chain reaction (PCR) together with appropriate primers is used to amplify the variable heavy ($V_H$) and variable light ($V_L$) genes from the MRNA preparations using well established procedures (Orlandi et al., *Proc. Nat. Acad. Sci. USA* 86:3833–3837, 1989 as an example). The RNA preparations are used to construct Fay combinatorial libraries in phage (Persson et al., *Proc. Nat. Acad. Sci.* 88:2432–2436, 1991; Huse et al., *Science* 246:1275–1281, 1989). Clones selected by screening are plaque-purified and the phagemids excised and used to transform *Escherichia coli*. Fabs from culture tranformants were then produced by procedures well known to those versed in the art (Gusow and Seemann, *Methods in Enzymology*, 99:121, 1991, Pluckthun, *Biotechnology*, 9:545–551, 1991, *Nature*, 347:497–498, 1991.

7.5 Results
7.5.1 DM27 1E11

Human tonsillar lymphocytes ($2 \times 10^6$ cells) were stimulated for three days in medium RPMI 1640 together with adjuvant peptide (Sigma) 10 g and dust mite extract (5 g). Cell preparations were collected, resuspended in RPMI for fusion with human-mouse heteromyeloma EL41. From this fusion, human hybridoma DM27/1Ell was selected. The hybridoma was cloned two times and growth maintained in medium RPMI 1640 supplemented with 10% fetal calf serum. Human Mab DM27/1E11 was obtained from hybridoma supernatant by affinity chromatography on SEPHAROSE protein G (Pharmacia). Antibody DM27/1E11 reacted with dust mite extract and with purified Der p I preparations (Table 5). Isotype characterization of the antibody established it to be IgG1.

TABLE 5

Human anti-dust mite monoclonal antibodies ELISA OD on Plates Coated with:

| Hybridoma | Lymphocyte Donor[1] | DMA[2] | Casein | Reactivity with: Der p I | Der p II[3] |
|---|---|---|---|---|---|
| DM27 1E11 |  | 0.196 | 0.049 | + | − |
| DM27 1A11 | Tonsil | 0.065 | 0.000 | − | + |
| DM27 1F10 |  | 0.094 | 0.000 | − | + |
| DM27 2G9 |  | 0.111 | 0.000 | + | − |
| DM28 1D11 |  | 0.160 | 0.019 | + | − |
| DM28 2A2 | PBL | 0.172 | 0.043 | − | + |
| DM28 2E9 |  | 0.391 | 0.176 | + | − |
| DM31 1H2 |  | 0.138 | 0.072 | − | + |
| DM31 1G7 | Tonsil | 0.179 | 0.096 | + | − |
| DM31 2B2 |  | 0.191 | 0.000 | + | − |
| DM31 2C10 |  | 0.202 | 0.000 | + | − |

[1]Fused with human-mouse heteromyeloma
[2]Dust mite extract
[3]ELISA test

7.5.2 Other human anti-dust mite M

Table 5 lists representative human anti-dust mite allergen monoclonal antibodies generated by fusion of human lymphocytes with human-mouse heteromycloma ELAI. Lymphocytes were obtained from human peripheral blood (hybridomas DM28/1D11, DM28/2B2, DM28/2E9) and from tonsillar tissue (DM27/1E11 to 2G9 and DM31/1H2 to 2C10).

TABLE 6

Immunoreactivity of Human Antibodies From EBV-Transformed Lymphocyte Lines

| EBV - Transformed Tonsillar Lymphocyte[3] | | Tonsillar Tissue[2] | Antibody Reactivity with[1] | | |
|---|---|---|---|---|---|
| | | | DMA | Der p I | Der p II |
| EBA-11 | | T10 | + | + | − |
| EBV-12 | | T14 | + | − | + |
| EBV-13 | A | T13 | + | + | − |
| | B | T13 | + | + | − |
| | C | T13 | + | − | + |
| | D | T13 | + | + | − |
| EBV-14 | A | T14 | + | − | + |
| | B | T14 | + | + | − |

[1]Binding of antibody determined by ELISA assay with dust mite extract and purified proteins
[2]Tonsillar tissue obtained at tonsillectomy from allergic donors
[3]Tonsillar lymphocytes transformed with Epstein Barr Virus (EBV)

The Mabs reacted in ELISA tests with dust mite extracts as compared to control microtiter wells coated only with casein. Specificity tests indicated that 9/11 reacted with Der p I.

7.5.3 In Vivo Testing of Anti-Der p Mab for Down-Regulating T Lymphocyte Mediated Responses to Dust Mite Allergens The importance of T lymphocyte responses in the pathogenesis of allergic conditions resulting from exposure to dust mite allergens is clearly established (Ishizaka, *Ann. Rev. Immunol.*, 2:159–182, 1984; O'Hehir et al., *Int. Allergy Appl. Immunol.*, 88.:170–172, 1989; Frew and Kay, *J. Immunol*, 141:4158, 1988; Alexander et al., *Lancet*, 339:324–328, 1992).

The synthesis of specific IgE antibody and the differentiation and growth of effecter cells such as mast cells and eosinophils are dependent upon the activation of CD4+ cells (O'Hehir et al.,).

Control of T lymphocyte responses to dust mite allergens is an important pathway in treating allergic diseases caused by these substances. This can be effected by treatment with immunosuppressive drugs. In view of the overall toxicities of agents such as cyclosporin A these agents are not considered applicable for the treatment of most asthma patients. Alternative approaches for suppressing T cell responses by manipulating the immune network are more appropriate since these treatments are much less toxic.

From the above considerations evaluation of the potential of anti-dust mite Mabs for controlling allergic diseases is evaluated initially by demonstrating that treatment suppresses T lymphocyte mediated responses.

Inhibition of Delayed Type Hypersensitivity (DTH) Responses in Mice to Dust Mite Allergens 8.1 Induction of DTH in Mice to Dust Mite Extracts Dust mite extract (DMA) 10 to 200 mg mixed with 1:1 v/v with complete Freund's adjuvant (CFA) is injected subcutaneously into two sites in BALB/c mice. Control mice are injected with CFA mixed with PBS or an irrelevant protein. Mice are challenged 5 to 28 days later by injection of DMA (10 mg) or purified Der p I/II preparations given intradermally into the left ear pinna using the procedures described by Austin et al., 1991 (Austin et al., *J. Natl. Cancer Inst.*, 1991). The uninjected right ear serves as the control. Twenty four and 48 hours after challenge, the thickness of the ears is measured. The differences between challenged and nonchallenged ears is calculated and the measurements expressed as increment in ear swelling as a measure of the DTH response. (Austin et al., *J. Nat. Cancer Inst.*, 1991, Kuriboyashi et al., *Cell Immunol.*, 108:366–377, 1987, Morikawa et al., *Immunology*, 74:146–152, 1991.

To measure the effect of anti-dust mite Mab treatment, mice receive antibody at various times before or after sensitization with DNU. Mab may be administered by various routes and immunological adjuvants may be included in the preparation.

Suppression of DTH responses against dust mites may be improved by combination treatment with Mabs reacting with different epitopes on the major allergic proteins such as Der p I and Der p II. The general approach then has been to identify Mabs singly or in combination which are effective for suppressing DTH responses to individual Der p (and Der f) proteins. Further selection of NUB combinations may also be employed for suppression of DTH responses to mixed dust mite allergens such as those contained in crude extracts (DMA).

A DTH response is elicited in BALB/c mice sensitized with DMA (10 µg) and challenged in the ear with DMA 5 days later. There is a significant (p<0.01) increase in ear swelling in DMA-sensitized mice compared to nonsensitized controls DTH responses are be similarly detected in BALB/c mice sensitized with DMA followed by ear challenge with Der p I protein preparations.

8.2 Suppression of Der p I induced DTH Response in Mice Treated with Anti-Der p Mab Mice sensitized with DMA extract (10 µg) and challenged in the ear 28 days later elicit a delayed type hypersensitivity response as assayed by ear swelling. This response is significantly reduced when mice are treated after sensitization with DMA with 10 to 50 µg anti-Der p I Mab H11 (FIG. 17). Prophylactic experiments show that treatment with Mab H11 following sensitization with DMA suppresses the development of DTH responses following ear challenge with Der p I (10 µg) as shown in FIG. 17. When DMA sensitized mice are treated with H11 (3×20 µg days 4, 7 and 14) and ear challenged, on day 28 significantly reduced ear swelling is observed. A significant reduction in DTH responses to Mab H11 treatment is obtained using a range of Mab doses from 1 µg to 1 mg given up to 5 times. This response is further enhanced when Mab H11 is administered with aluminum hydroxide as adjuvant (ALHYDROGEL 85; Superphos Biosector a/s Vedbaek, Denmark).

8.3 Decrease in T cell reactivity by in vitro parameters

In addition, lymphocytes from these sensitized animals are isolated from lymph nodes or spleen, and single cell suspensions are placed in culture and stimulated with either whole DMA or Der p I and Der p II. T cell activation is measured either by incorporation of radiolabeled thymidine, or by production of IL2. Those animals injected with AB1 have significant decrease in either of these activation markers as compared to sensitized animals without this treatment.

TABLE 7

Suppression of Delayed Type Hypersensitivity Responses to Der pI in Mice by treating with Anti-Der pI Antibodies

| Treatment regimen Reagent | Dose µg | Schedule Days[1] | Increase in ear swelling (10 mm) following challenge with Der p I (10 µg)[2] |
|---|---|---|---|
| — | — | — | 120 ± 11 |
| Mab H11[3] | 20 | 4,7,14 | 250 ± 9 |
| Mab 198 | 20 | 4,7,14 | 98 ± 14 |
| Mab H11 | 10 | 4,7,14 | 48 ± 7 |
| Mab H11 in Alum | 10 | 4,7,14 | 13 ± 5 |
| Mab H11 in Alum | 5 | 4,7,14 | 22 ± 8 |
| Mab 198 in Alum | 10 | 4,7,14 | 92 ± 12 |

[1]With respect to DMA sensitization (Day 0)
[2]Challenge on Day 21
[3]Anti Der pI Mab

TABLE 8

Suppression of Der p I-Specific IgE Responses in Mice by Treatment with Anti-Der p I[1]

| Expt | Schedule of Mab H11 TReatment (days)[3] | Mab H11 µg | Serum IgE Titer[2] |
|---|---|---|---|
| 1 | — | — | 60 ± 10 |
|   | 4,7,14 | 3 × 10 | 23 ± 7 |
| 2 | — | — | 75 ± 12 |
|   | 7,14,21 | 3 × 5 | 43 ± 11 |

TABLE 8-continued

Suppression of Der p I-Specific IgE Responses in
Mice by Treatment with Anti-Der p I[1]

| Expt | Schedule of Mab H11 TReatment (days)[3] | Mab H11 μg | Serum IgE Titer[2] |
|---|---|---|---|
| | 7,14,21 | 3 × 10 | 18 ± 12 |
| 3 | — | — | 68 ± 12 |
| | 14,21,28 | 3 × 10 | 21 ± 4 |

[1]Mice Immunized 3 to 5 times at monthly intervals with Der p I
[2]Serum assay 14 days after final treatment with MAB H11
[3]MAB H11 treatment 7 days after final treatment with Der p I extract 8.4 Assessment of down regulation of IgE anti- DMA response 8.4.1 SCID mouse model Down-regulation of antigen processing by injection of anti-DMA monoclonal antibodies can be assessed by use of mice genetically bred to lack an immune system (severe combined immune deficiency - SCID mice. The animals do not have the capacity to be sensitized, but can mount an anamnestic response. These animals are repopulated with human immune systems using either peripheral blood mononuclear cells, lymphocytes from tonsils, or a mixture of T cell clones taken from disease specific organs such as the lung in asthmatics, and mixed with peripheral blood mononuclear cells. Optimally these lymphocytes should be taken from atopic patients suffering from allergic reactions to the target antigen, such as dust mite, as manifest by antigen-specific IgE, skin test positivity to the antigen, and clinical symptoms indicating ongoing exposure. Alternatively subjects may be deliberately exposed to the allergen prior to donation of the tissues.

The SCID mice are injected intravenously with 1–10×10[6] and blood is drawn after 1 week and measured for total and antigen specific IgM, IgG, and IgE, to verify engrafting. They are then injected with either DMA specific monoclonal antibody of an irrelevant monoclonal antibody of the same subclass, and challenged with antigen, 10–100 μg without adjuvant 1–3 days later. The antigen challenge is repeated again 2 weeks later, and blood is drawn weekly for up to 6 weeks thereafter.

8.4.2 Normal mouse model

In a second model, BALB/c or A/j mice are exposed to DMA either as the purified antigen, or as the semipurified extract. The exposure can either be as an injection with and without adjuvant, in a dose range of 20 μg to 1 mg given as 1–3 injections 1 week apart, or as the aerosolized antigen, given in a nebulized form up to 1 mg/day for 10 days. Following exposure the IgG and IgE anti-DMA antibody response is determined.

In order to determine if a candidate Mab is able to down-regulate the response, the Mab is either given prior to sensitization, at a dose from 0.01 μg to 100 μg, with or without adjuvant, as multiple injections ranging from 1–10, up to 1 week prior to sensitization; or after sensitization with or without adjuvant at periods ranging from immediately after the last antigen exposure up to 1 month after exposure. In some cases the latter group of animals may be rechallenged to investigate the effect of such treatment on the secondary response.

Results are shown in Table 9.

TABLE 9

Suppression of Der p I-Specific IgE Responses
in Mice by Treatment with Anti-Der p I

| Schedule of Mab H11 Treatment (days) | H11 μg | Serum IgE Titer |
|---|---|---|
| — | — | 60 ± 10 |
| 4,7,14 | 3 × 10 | 23 ± 7 |
| — | — | 75 ± 12 |
| 7,14,21 | 3 × 5 | 43 ± 11 |
| 7,14,21 | 3 × 10 | 18 ± 12 |
| — | — | 68 ± 12 |
| 4,21,28 | 3 × 10 | 21 ± 4 |

In these experiments, mice were immunized 3 to 5 times at monthly intervals with Der p I. Treatment with Mab H11 was conducted 7 days after final treatment with Der p I extract. Serum assays for IgE titer were performed 14 days after final treatment with Mab H11.

8.4.3 Aerosol-sensitized mouse model

In a third model to measure the ability of the MAb to down-regulate the response either BALB/c or A/j mice or Brown Norway rats are treated with nebulized allergen for 30 minutes each week for 6 weeks, with molecules in the range of less than 1 μM, and tested for production of total and antigen specific IgG and IgE (McMenamin, C., et. al. *Immunology*, 77:592–596, 1992). To test the ability of the candidate MAb to significantly down-regulate either of these antigen-specific classes, the MAb can be given as in the example above, either before or after antigen challenge, with or without adjuvant.

In both cases the IgE and IgG response is determined by the general methods set forth in Section 6 below, except that the antigens will be Der I or Der II instead of Lol p I. In addition, animals are injected intradermally with 1–100 μg of antigen and the cutaneous response is determined 30 minutes later as a measure of IgE response.

Example: Inhibition of Allergic Response to Dust Mite Allergens 9.1 Development of an IgE Dust Mite Murine Model to Detect Serum IgE Responses A model system exists on which to test the IgE-mediated allergic reaction to dust mite. In this model, ovalbumin (OVA) is aerosolized, and used to sensitize BALB/c mice by inhalation. These animals develop immediate hypersensitivity skin test reactions upon challenge, and sera are able to transfer passive cutaneous anaphylaxis. The model is antigen specific. IgE sensitization can be transferred with peribronchial lymph nodes of sensitized animals (Saloga et al. *J. Clin. Invest.* 91:133–140, 1993). Bronchospasm in the animals was demonstrated following electrical field stimulation (Larsen et al. *J. Clin. Invest.* 89:747–752, 1992), although there was no acute inflammatory cells including eosinophils (Renz et al. *J. Allergy Clin. Immunol.* 89:1127–1138, 1992), The OVA system represents a good model for assessing immunotherapeutic agents for treatment of dust mite allergy. Adjuvant is not used in stimulating allergic responses, thus avoiding nonspecific T cell and other inflammatory responses, as well as alteration of cellular functions produced by these agents. The aerosolized route of sensitization is similar to the human situation, and allows specific measurement as to the effect on the airways.

This aerosolized allergen model with Der p I or Der p II has been used to demonstrate that immunization of BALB/c mice with vaccines containing murine anti-Der p I or Der p II monoclonal antibodies suppresses anti-Der p I or Der p II IgE antibody responses. By way of illustration experiments using anti-Der P I Mab 2C7 to suppress Der p I serum IgE responses are described.

9.1.1 Sensitization with Aerosolized Dust Mite Allergen

Particles of 2–3 microns, small enough to reach the lower respiratory tract (Yu, *Powder Tech.* 21:55, 1978) are generated by a jet nebulizer (Micro Cirrus, Intersurgical, Middlesex, UK) under a continuous pressure of 29 PSI. Female BALB/C mice (8–12 weeks old) are sensitized by ultrasonic nebulization, of 1% whole dust mite extract in sterile phosphate buffered saline pH 7.3, based on the procedures developed by Gelfand and associates (Renz et al., *J. Allergy Clin. Immunol.* 89:1127–1138, 1992). Up to 5 mice are placed in a sensitization chamber, and the dust mite solution is aerosolized into the inlet port. They are exposed to the aerosolized allergen 20 minutes for 10 days. Controls include PBS as a negative control, and Ovalbumin (OVA 1%) and crude, soluble rye grass extract (Lol p) obtained from a commercial source as positive controls.

9.2 Immune Response Against Der p I

The Der p I specific IgE response is measured by passive cutaneous anaphylaxis. Positive results are confirmed by measurement of immediate cutaneous hypersensitivity, and measurement of total and antigen specific IgE by ELISA. Airway responsiveness is measured by testing for increased bronchial resistance to allergen challenge.

9.2.1 Passive Cutaneous Anaphylaxis (PCA)

Inbred Sprague-Dawley rats (6/group) are injected intradermally with 100 μl of a range of dilutions of serum samples. In this assay up to 8 intradermal sites are available so that a series of dilutions of test sera can be injected. In controls, rats are injected with serum from control mice exposed to aerosolized saline or other allergens, e.g., ovalbumin or rye grass Lol p I. Forty eight hours later rats are injected intravenously with 10 to 50 μg of purified Der p I (dose determined in pilot studies) in admixture with 1 ml Evans blue dye (1%). Rats are killed 30 minutes later and the response is determined from the infiltration of Evans blue as visualized on the inverted skin surface. A positive skin response is defined as a wheal of greater than 0.3 cm in diameter. A test serum titer is determined by comparison with controls.

9.3 Suppression of Anti-Der p I IgE Responses

BALB/c mice (10/group) were immunized with Mab 2C7 in alum using conditions defined to stimulate anti-idiotypic antibodies. Control mice (10/group) received an irrelevant Mab (anti-CEA Mab 337) or saline. Following immunization mice were exposed to aerosolized dust mite extract or saline as already described and blood samples were taken two days after completing the treatment protocol. Serum samples from groups of 10 mice were pooled and tested for IgE specific antibody by the passive cutaneous anaphylaxis assay and by ELISA assay.

9.3.1 Passive Cutaneous Anaphylaxis Assay

In the experiment summarized in Table 10, treatment of mice with Mab 2C7 prior to sensitization with aerosolized Der p produced a 6 fold reduction in the IgE response to Der p I as measured by passive cutaneous anaphylaxis. In comparison, mice treated with control Mab 337 still generated anti-Der p I IgE antibodies (Titer 1/128) when exposed to aerosolized Der p.

9.3.2 Determination of Murine Serum Anti-Der p I IgE Antibody Levels

Anti-Der p I serum IgE antibody titers are measured by ELISA in the following procedure:

1. ELISA microtiter plates are coated with goat anti-human IgE antibody.
2. The microtiter plates are washed and blocked with casein buffer.
3. Human serum from atopic dermatitis subjects is added and incubated overnight at 4° C.
4. The microtiter plates are washed with PBS-Tween.
5. BALB/c mouse antisera raised against Mab-Keyhole limpet hemocyanin is added to microtiter plates. For a control, normal BALB/c mouse serum is used.
6. The microtiter plates are washed.
7. The bound mouse antibody is detected by reaction with goat anti-mouse IgG labeled with horse radish peroxidase.
8. The substrate ABTS is added.
9. Color development is determined at OD 405 nm Standard ELISA reagents are described in Section 5:2:2

TABLE 10

Inhibition of Anti-Der p I IgE Antibody Responses in Mice Immunized with Anti-Der p I Mab 2C7 Passive Cutaneous Anaphylaxis Test (PCA)

| Group | Immunizing Mab* | Sensitization by Aerosolized Exposure to: | PCA Titer to Der p I |
| --- | --- | --- | --- |
| 1 | 2C7 | Der p | 1:4 |
| 2 | 2C7 | PBS | 0 |
| 3 | Control Mab 337 | Der p | 1:128 |
| 4 | Control Mab 337 | PBS | 1:2 |
| 5 | Saline | Der p | 1:256 |

*5 injections of Mab (10 μg in alum) delivered subcutaneously at two week intervals; Mab 337 is directed against carcinoembryonic antigen.

Treatment of BALB/c mice with Mab 2C7 in alum did not influence the induction of anti-ovalbumin IgE antibody responses in mice receiving aerosolized ovalbumin. In these experiments the PCA titer in mice treated with either saline or Mab 2C7, or Mab 337, and then exposed to aerosolized ovalbumin were 1/512 and 1/256 respectively.

9.3.3 ELISA Assay Anti-Der p I IgE Antibody

Serum samples from mice exposed to aerosolized Der p were assayed for Der p I-specific IgE antibodies using an ELISA assay (described supra). Briefly, serum samples undiluted and diluted ½ to ⅟50 were added to ELISA microtiter plates coated with Der p I. After incubation and washing, bound mouse serum IgE was detected with rat anti-mouse IgE horse radish peroxidase conjugate. A serum dilution titer was determined from the ELISA OD readings (405 nm) in comparison with background OD values with microtiter plates exposed to normal mouse serum.

In the example summarized in Table 11, mice treated with saline or control anti-CEA Mab 337 developed anti-Der p I IgE antibodies when exposed to aerosolized Der p preparation(serum titers ⅟50 and ⅟40 respectively). This response was reduced some ten-fold in mice immunized with anti-Der p I Mab 2C7 in an alum formulation (serum titer ¼). In control studies immunization with Mab 2C7 in alum did not influence the stimulation of anti-ovalbumin IgE antibodies following exposure of mice to aerosolized ovalbumin. In one example the serum anti-IgE titer as determined by ELISA in mice immunized with Mab 2C7 or Mab 337 (⅟400 in each case) was comparable to that obtained in mice initially treated with PBS (titer ⅟500).

9.3.4 Results

In the example described above, treatment of BALB/c mice with anti-Der p I Mab 2C7 in an alum formulation led to the suppression of the ability of mice to generate anti-Der p I IgE antibodies on exposure to aerosolized dust mite extracts (Der p). In further examples anti-Der p I Mab H11 suppressed anti-Der p serum IgE responses and Mab 2H5 suppressed anti-Der p II IgE responses.

TABLE 11

Inhibition of Anti-Der p I IgE Antibody Responses in Mice Treated with Anti-Der p I Mab 2C7: ELISA Assay

| Group | Immunizing Mab* | Sensitization by Aerosolized Exposure to: | Serum Anti-Der p I IgE Titer |
|---|---|---|---|
| 1 | 2C7 | Der p | 1/4 |
| 2 | 2C7 | PBS | 0 |
| 3 | Control Mab 337** | Der p | 1/40 |
| 4 | Control Mab 337 | PBS | 0 |
| 5 | PBS | Der p | 1/50 |

*5 injections of Mab (10 μg in alum) delivered subcutaneously at two week intervals
**Mab 337 - anti-carcinoembryonic antigen Mab 10. Example: Use of anti-urushiol monoclonal antibodies (AB1) to down regulate the T cell response to poison oak and ivy allergy poison oak/ivy allergy is a delayed type hypersensitivity (DTH) response to an allergen (urushiol) in the oil of the plants. The natural allergen is a mixture of 3-n-alkylcatechols with a C15 or C17 side chain either fully saturated e.g. 3-n-pentadecylcatechol, PDC) or having 1 to 3 unsaturated bonds (FIG. 25) (Symes and Dawson, 1954, *J. Ann. Chem. Soc.* 76:2959–2963). In the initiation of an allergic response the allergen first undergoes quinone formation. The quinone then undergoes reaction with cell proteins through Sulfhydryl or amino groups and these products initiate the allergic response.

10.1 Preparation of 3-n-Alkylcatechol conjugates for Use as Immunogens

Urushiol and related 3-n-alkylcatechols produce T cell responses; antibodies have never before been demonstrated. Thus, to generate anti-urushiol antibodies, it has been necessary to synthesize analogs capable of stimulating B cell responses. These have been synthesized by several routes, a preferred pathway being reaction of quinones of urushiol and PDC with proteins, peptides, and amino acids.

10.1.1 Reaction of auto-oxidized urushiol to proteins

The conjugation procedure is based upon that described by Liberato et al., 1981, *J. Med. Chem.* 24:28–33. Urushiol, 1.56 μM dissolved in 1 ml acetone is placed into a conical flask and dried onto the inner surface under a stream of nitrogen. Protein solution (serum albumen 100 mg in 10 phosphate buffered saline pH 7, or keyhole limpet hemocyanin in sodium hydrogen carbonate buffer pH 8.4) is added. Alternatively, urushiol may be added drop-wise e.g. 0.2 ml urushiol added to KLH solution 20 mg in 2 ml of buffer pH 8.4. The heterogeneous mixture is stirred open to air at room temperature for up to 48 hours. During this time the urushiol undergoes o-quinone formation and protein coupling to yield a red-brown colored solution. The solution is chromatographed (e.g. on Sephadex G25) to separate the protein conjugate. In a typical example, the absorbance (480 nM) of the albumin solution increased from zero to 0.59. The final solution is sterilized and stored at 4° C.

10.1.2 Conjugation of Alkylcatechol to Protein through its n Acetyl Cysteine Intermediate to Common Protein Carriers Quinone derivatives of urushiol and 2-n-pentadecylcatechol (PDC) are prepared by oxidation of urushiol or PDC with silver oxide using procedures described by Liberato et al. ibid. to yield N-acetyl-S (2,3)-dihydroxy-4-pentadecylphenyl cysteine (PDC-n-acetyl cysteine). The purity of the product was assessed by thin layer chromatography, elemental analysis and NMR spectroscopy to conform with published data (ibid). The quinone derivative of urushiol is similarly reacted with N-acetyl cysteine.

10.1.3 Conjugation of 3-n-pentadecylcatechol (PDC) to Polyaspartic Acid

Conjugation of PDC to polyaspartic acid is effected through a carbamide complex. PDC (10 mg) was dissolved in dioxase (1 ml). Dicyclohexylcarbodiimide (DCC: 2 mg) was added, and reacted for 18 hours at 4° C. The complex was then added to acid (5 mg; 41.6 μM) in phosphate buffered saline pH 5 and after 30 minutes the conjugate isolated by Sephadex G25 chromatography. Spectroscopy analys (277 nm) indicated the mean substitution ratios was 42.8 μmol/mg.

10.2 Production of Anti-Urushiol Monoclonal Antibodies and TCR's

Methods for producing murine monoclonal antibodies have been described (Section 5). BALB/c mice were immunized on day 0 with PDC—N acetylcysteine (50 μg) subcutaneously in Freunds' complete adjuvant followed by an intravenous boost dose of PDC-N acetyl cysteine on day 7. Spleen cells were harvested on day 11 and fused with myeloma P3 NSO cells. Hybridoma clones are selected as described supra.

Anti-urushiol producing monoclonal antibodies are identified by ELISA assays. Briefly, polyvinyl microliter plates (Falcon) are coated with urushiol—or PDC-conjugates such as PDC and urushiol—N acetylcysteine and PDC-polyaspartate. Hybridoma supernatants are added, incubated 45 minutes, washed and bound with mouse immunoglobulin deleted with horse radish peroxidase conjugated rabbit anti-mouse immunoglobulin. This methodology yielded Mab 991/81/7, of the IgM isotype from a mouse immunized with PDC N acetyl cysteine. Mab 991 is purified from hydridoma culture supernatants by ammonium sulfate precipitation and fractionation by Sephacryl S300 gel filtration chromatography.

10 10.3 Immunoreactivity of Mab 991

The immunoreactivity of Mab 991 is initially determined by its binding in ELISA assay to urushiol and PDC conjugates but not to carrier molecules. The specificity of Mab 991 is further defined by the inhibition of its binding to urea-N-acetyl cysteine by compounds related to 3-N-alkylcatechols. This is illustrated by FIG. 15 which summarizes inhibition of Mab 991 to urea-N-acetyl cysteine. Thus compounds such as catechol and catechin hydrate with features of the catechol moiety inhibits Mab 991 binding. From these experiments Mab 991 is described as reacting with the catechol structure (FIG. 26).

10.4 Down-regulation of Delayed Type Hypersensitivity Responses to Urushiol

The use of anti-urushiol monoclonal antibodies to suppress allergic responses to urushiol has been evaluated using a murine model (Dunn et al., 1982, *Cell Immunol.* 68:377–388). BALB/c mice are sensitized by application of urushiol or PDC (2–4 mg) to the abdomen in acetone (100 μl). Sensitization to the allergen is then detected from day 4 up to day 42 by application of urushiol or PDC (50 μg in 10 μl acetone) to the dorsal side of one ear. The other ear is treated with acetone only (10 μl). Ear thickness is then detected using a sensitive pressure micrometer (Mitutoya, Japan) and the difference between allergen-challenged and control ears determined.

In a prophylactic approach (FIG. 27) mice are treated by a single or multiple intravenous injections of Mab using a range of doses (1 to 25 µg). Mice are then sensitized to the allergen and challenged on the ear. As an example of this approach, Mab 991 treatment (3 times, 10 µg) suppressed to DTH response to urushiol compared to control mice receiving an unrelated IgM Mab (B55: anti-breast cancer).

In therapeutic tests Mab is given after sensitization to urushiol or PDC. This is illustrated in FIG. 28 where urushiol sensitized mice received Mab 991 as a single dose (10 µg) intravenously 21 days after sensitization. When ear challenged on day 42 (50 µg urushiol), the DTH response was significantly reduced.

Mab in adjuvant are even more effective than Mab alone. This is illustrated by experiments where urushiol sensitized mice were treated on day 7 and 14 with Mab 991 (1 µg) in complete and then incomplete Freunds' adjuvant. When ear challenged on day 21 the DTH response was reduced by almost 80 per cent compared to that in control mice receiving control Mab (FIG. 29).

10.5 Anti-urushiol antibodies

Immunoglobulin molecules (Ig) in the form of B lymphocytes to urushiol are induced in mice, rats, rabbits, guinea pigs, or the like by techniques well known to those skilled in the art, wherein such techniques employ urushiol protein carrier conjugates as previously described. For example, animals are immunized with one or more injections of urushiol-protein conjugates. These are administered by any of several routes including intravenous, subcutaneous, intramuscular and intradermal injection with or without an adjuvant capable of potentiating host immune response. An example of such an adjuvant is complete or incomplete Freund's adjuvant. In some instances, immunoglobulin molecule responses to urushiol are enhanced by deleting immune responses to carrier protein. This is accomplished by elimination of responses to carrier protein by treatment with lymphotoxic drugs using the general procedures described by Thomas, W. A., *J. Immunol. Methods,* 1987, 97:237–243. Briefly, animals are immunized with carrier protein. At intervals after immunization, animals are treated with cytotoxic drugs, e.g., cyclophosphamide (0.40 mg/kg body weight) to eliminate lymphocyte clones producing immunoglobulin-molecules to carrier protein. Animals are then allowed to recover from this treatment and then immunized with urushiol-protein conjugate. Immunoglobulin molecules are derived from serum of immunized animals. In some cases, mouse and/or rat monoclonal antibodies are produced by hybridoma production with antibody-producing cells e.g., spleen cells from immune donors (CFpo3).

10.5.1 Production by simple immunization with urushiol-carrier with or without adjuvant Adult BALB/c mice are immunized with urushiol-key hole limpet hemocyanin conjugate (uru-KLH). In a typical protocol, the first dose (day 0) of 100–400 pg protein conjugate in complete Freund's adjuvant (CFA) emulsion is injected intraperitoneally. The second immunization (day 10–14) is injected intra-peritoneally. This consists of uru-KLH (100–400 mg) emulsified in incomplete Freund's adjuvant (ICFA). A third dose of uru-KLH is given without adjuvant by intraperitoneal injection 10–14 days later. Further doses are given at 2–3 week intervals until immunoglobulin molecules to urushiol are detected in serum.

10.5.2 Production of anti-urushiol responses using additional immune manipulation Adult BALB/c mice are immunized intraperitoneally with human serum albumin (10 Mg) in complete Freund's adjuvant. Three days later mice are treated with cyclophosphamide (40 mg/kg intraperitoneally). This treatment destroys lymphocytes producing Ig to human serum albumin (HSA). After resting for 26 25 days, mice are then immunized with uru-HSA (100–200 mg) in complete Freund's adjuvant. As in Example A, supra, the immunization is given at intervals with and without Freund's adjuvant (complete or incomplete) until immunoglobulin molecules are detected in serum.

10.5.3 Use of urushiol alone as B cell immunogen

Adult BALB/c mice are immunized by multiple paintings of free urushiol in acetone, up to about 2.5 mg, on the abdomen and sera is repeatedly drawn for testing. Paintings are continued until anti-urushiol antibodies are found in the serum.

10.5.4 Use of lymphocytes from sensitized humans

Sensitized humans are challenged with urushiol by epicutaneous administration of 0.1–5µg of urushiol in acetone. Sera are tested for anti-urushiol antibodies, and lymphocytes from collected from cutaneous lesions or from peripheral blood are used to produce hybridomas by techniques well known to those skilled in the art.

10.6 Production of Anti-Urushiol Monoclonal Antibody ($Ab_1$)

10.6.1 Murine monoclonal antibodies

Methods of making murine monoclonal antibodies to an antigen of interest are well known to those skilled in the art and have been described previously. (Goding, supra) For example, spleen cells from urushiol-immune mice are obtained by disaggregation of spleen tissue in serum-free medium (RPMI 1640). Mouse myeloma cells (P3-NS1, Sp 2/0, X63-Ag8.653, NSO/1, or the like) are harvested when sub-confluent and still in exponential growth and washed in serum free RPMI 1640 medium. Cell preparations are mixed in a ratio of 1 myeloma cell to 5 spleen cells and pelleted by gentle centrifugation in conical-bottomed flasks. The supernatant is removed, cell pellet loosened and polyethylene glycol (PEG 1500) added, 1.8 ml over 2 minutes. The cells are rapidly hand rotated and allowed to stand 2 minutes. Serum free RPMI 1640 medium is added drop-wise (1 ml over 1 minute then 20 ml over 5 minutes) while rotating the tube, then centrifuge. The supernatant is removed and the cell pellet suspended in RPMI 1640 with 15% fetal calf serum and hypoxanthine, methotrexate, and thymidine.

Further growth medium is added and the mixture is plated at $5\times10^3$ myeloma cells, 100 µl/well in 96 well flatbottomed microtiter plates on a feeder layer of rat peritoneal exudate cells. The cells are incubated at −37° C. in 5% $CO_2$. (Galfre, et al., *Nature,* 1977, 226:550–552). Fusion plates are examined microscopically every 3–4 days and fed by aspirating half of the supernatant from wells and replacing with fresh growth medium. Wells having hybridoma colonies visible to the naked eye are tested for Ig. Murine monoclonal antibodies are obtained from tissue culture supernatants of hybridoma cells grown in vitro. These are purified in various ways, the preferred method being affinity chromatography on a Sepharoseprotein A column. In this procedure hybridoma cell supernatants are passed through chromatography columns containing Sepharoseprotein A. The bound Ig is then eluted from the column using appropriate media.

10.6.2 Production of human monoclonal antibodies 10.6.2.1 From murine monoclonal antibodies The use of murine monoclonal antibodies to produce human monoclonal antibodies by gene fusion techniques are well known to those skilled in the art. They are of two types. The first utilizes the variable region of the murine antibody gene cloned onto a human antibody backbone. The second uses the idiotypic region of the murine monoclonal antibody gene cloned onto a human backbone. (See e.g., Morrison et al., EPO EP173494 (3/5/86); Neuberger et al., PCT WO-8601533 (3/15/86); Robinson et al., PCT WO-8702671; Morrison et al., *PNAS, USA*, 1984, 81:6851–6855; Boulianne et al., *Nature*, 1984, 312:643–646; Neuberger et al., *Nature*, 1985, 314:268–270).

Chimeric antibody production involves isolation of messenger RNA (mRNA) from a murine B cell hybridoma producing the relevant monoclonal antibodies. This is then cloned and a complementary DNA library is prepared. See, e.g., Perbal, B., *A Practical Guide to Molecular Cloning*, 2d ed., John Wiley & Sons (1988), which is incorporated herein by reference. The required variable regions of the light and heavy chain genes are then identified with appropriate probes. These are sequenced and made compatible with a constant region gene segment which is also obtained by construction of cDNA preparations and cloning. Heavy and light chain coding sequences are constructed by linkage of the cloned specific immunoglobulin variable (v) gene segment to cloned human constant gene sequence. On expression in prokaryotic and eukaryotic cells, chimeric antibodies are produced containing the antibody specificity of the mouse monoclonal antibody but with most of the molecule comprising human Ig amino acid sequences.

10.6.2.2 By fusion of human B lymphocytes with a mouse-human heterohybridoma

Human lymphocytes producing a desired antibody are fused with mouse-human heterohybridoma cells to produce humanized monoclonal antibodies. The human lymphocytes may be taken from an active urushiol skin lesion or from the peripheral blood.

In one embodiment, mouse/human heteromyeloma cells such as EL41 (deposited on May 16, 1990 with the European Collection of Animal Cell Cultures and having Accession No. 90051602) as described by Austin et al., *Immunology*, 1989, 67:525–530, are fused with human lymphocytes reactive with urushiol using polyethylene glycol according to the method of Galfre et al., supra. For example, lymphocytes are placed in 30 ml plastic universal bottles and washed twice with growth medium such as Dulbecco's modification of Eagle's medium (DMEM; Flow Laboratories) and the number of lymphocytes is determined by hemocytometer counting. EL41 cells are harvested, washed, and counted in a similar fashion. The two cell populations are then mixed at a lymphocyte:fusion partner ratio of 2:1 and washed for a third time. Following centrifugation the medium is discarded and 0.8 ml of 50% PEG pipetted over a 1 minute period onto the cell pellet with gentle agitation. The mixture is left for 1 minute then 1.0 ml of medium is added over a 1 minute period followed by the addition of 20 ml of medium added slowly over a 5 minute period. The cells are then centrifuged at 1200 rpm for 5 minutes, the medium discarded, and the cells resuspended by gentle pipetting in a 2 ml pipette. Twenty ml of selection medium (DMEM+10% FCS+$10^4$M hypoxanthine+$10^{-5}$M methotrexate+$10^{-6}$M thymidine) is finally added to the cell suspension and the cells aliquoted into two 96 well tissue culture microtiter plates containing rat peritoneal exudate cells ($2.5\times10^3$/well) as a feeder layer. An additional 100 μl of media is also added to each well. The selection medium is changed every 72 hours until resulting hybridomas have reached 50% confluence then every 48 hours. The growth of hybridomas is regularly checked and when the colonies cover 50% of the well the supernatant is analyzed for Ig. Hybridomas producing Ig of interest are immediately cloned. Established hybridomas are frozen down in aliquots of $20\times10^6$ cells/ml in 95% FCS and 5% dimethylsulfoxide (DMSO) and stored in liquid nitrogen.

10.7 Production of Anti-Urushiol T Cell Receptors For Use As Immunogens

Mice are vaccinated against haptens (oxazolone, DNFB), including urushiol, by immunization with T cells derived from lymph nodes of hapten sensitized donors. Mice are vaccinated by immunization with urushiol specific T cells. These may be cloned 20 T cells, T cell hybridomas, or peptides mimicking the TCR of the specific T cells.

10.7.1 Production of urushiol specific T cell lines from sensitized mice

BALB/c mice are sensitized following application of urushiol (0.01–5 mg) in acetone onto the dorsal skin. T cells from sensitized mice are obtained from several sources including lymph nodes or urushiol-induced cutaneous lesions and expanded in culture by in vitro stimulation with urushiol or urushiol-polymer conjugates using stimulation procedures well known to those skilled in the art. Urushiol specific T cell clones or T cell hybridomas are obtained by fusion of T cells with murine thymoma cells (BW 5147 cells as described by Bigby et al., *J. Immunol.,* 1989, 143:3867–3872). These cells produce immune responses to urushiol specific TCR. Such cells have utility as T cell vaccines which may be one of several types including viable or attenuated T cells and T cells modified by cross linking with agents such as glutaraldehyde (Cohen, I. R., and Weiner, H. L., *Immunol. Today,* 1988, 9:332–335). The TCR of the urushiol responding-T cell clone is identified by reaction with monoclonal antibodies which detect variable segments of the TCR (Kappler et al., *Nature,* 1988, 332:35–40).

In another approach, messenger RNA or DNA from cloned T cells reacting with urushiol are probed either directly or after amplification by polymerase chain reaction by specific hybridization with nucleic acid probes for TCR gene families using hybridization methods well known to those skilled in the art. The TCR sequence (in part) is obtained from the amplified DNA or RNA. Regions of TCR amino acid sequences are selected on the basis of their immunogenic or antigenic properties identified using algorithms to predict T cell helper/cytotoxic determinants (Rothbard, J. B., and Taylor, W. R., *EMBO,* 1988, 7:93–100). For example, peptides containing 14 or 15 amino acids are predicted to contain specific TCR sites for urushiol. Peptides of selected amino acid composition are then synthesized using standard procedures well known to those skilled in the art. Synthetic peptides are then used to vaccinate animals.

10.7.2 TCR produced from immune human donors

T lymphocyte clones are established from peripheral blood mononuclear cells (PBMC) or contact dermatitis lesions derived from urushiol sensitized human subjects by methods generally described by Kalish and others. (Kalish, R. S., and Morimoto, C., *J. Clin. Invest.,* 1988, 82:825–832; *J. Invest. Dermatol.,* 1989, 92:46–52). PBMC isolated from venous blood by FICOLL/HYPAQUE separation are cultured in IL-2 containing media and sensitized or expanded by inducing proliferation in vitro by the addition of urushiol in dimethylsulfoxide or on autologous PBMC (Byers et al., *J. Clin. Invest.,* 1979, 64:1437–1448). Other growth factors such as IL-4 may be used (Paliard et al., *J. Immunol.,* 1989, 81438,452–457). Following culture for a period of time to establish satisfactory cell growth, cells are cloned by limiting dilution using standard cell culture techniques. Cells are then grown and positive wells expanded. This phase may include further stimulation of cells with urushiol and autologous irradiated (5000R) PBMC as feeder cells. T cell clones are then established by standard techniques. Alternatively, T cell hybridomas may be employed as a source of TCRs. The T cell vaccine may be composed of one or more formulations including viable or attenuated T cells and T cells modified by cross linking agents, e.g. glutaraldehyde (Cohen, supra). Ideally, T cell vaccines should be of autologous origin since responses are generally restricted by the MHC component of the TCR (Schwartz, R., *Ann. Rev. Immunol.,* 1985, 3:237–261). Since broad MHC restriction is, however, involved in the recognition of certain haptens and antigens (Panina-Bordignon et al., *Eur. J. Immunol.,* 1989, 19:2237–2242). An alternative approach is to administer vaccines composed of pooled preparations of cloned T cells derived from a number of allogeneic donors.

In another approach, specific antigen binding regions of the TCR may be identified, and the peptide comprising that region synthesized as described previously for use as an immunogen.

Figure 1:
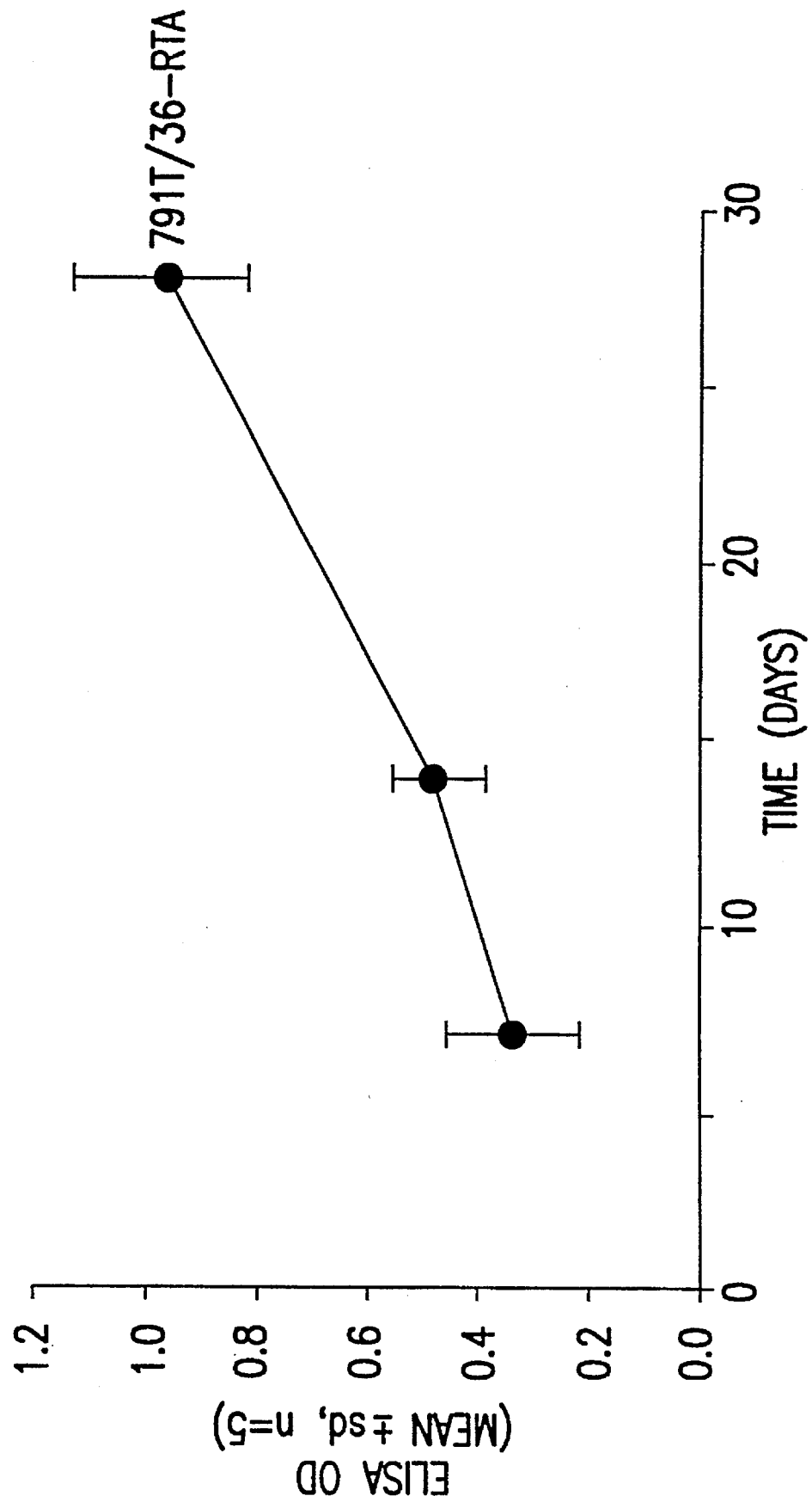

11. Suppression of the IgG antibody response to an exogenous antigen, Ricin A Chain (RTA) by monoclonal anti-RTA antibodies 11.1 Production of Ab1 to RTA BALB/c mice received a single intravenous injection of an immunotoxin composed of the murine monoclonal antibody 791T/36, conjugated by a disulfide bond to RTA. As shown in FIG. 1, significant titers of anti-RTA antibody were noted 7 days after injection, and continued to increase by day 30.

Figure 2A:
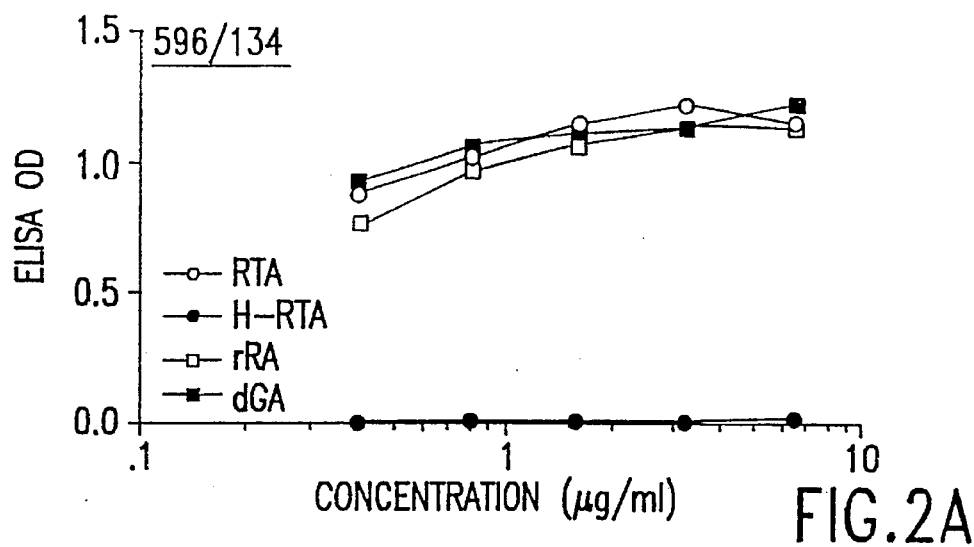
Figure 2B:
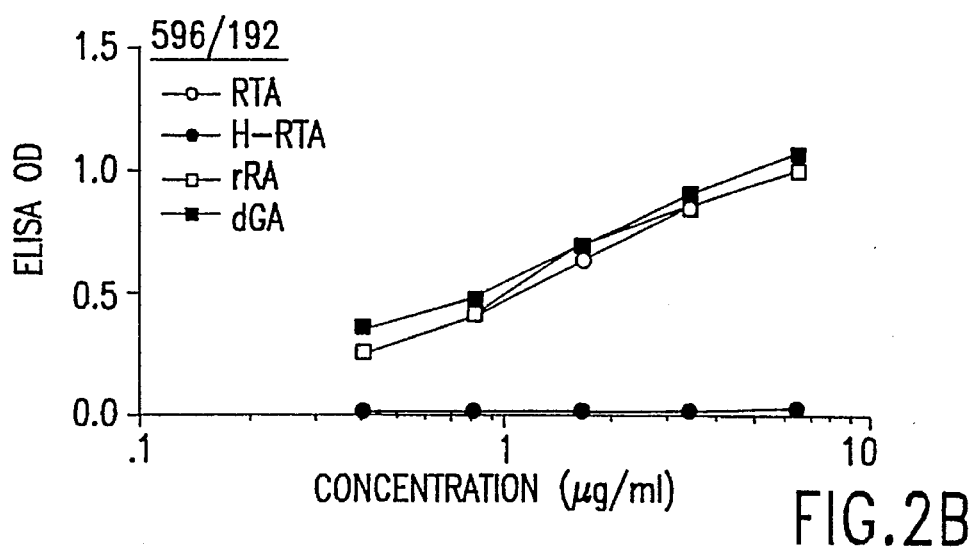
Figure 2C:
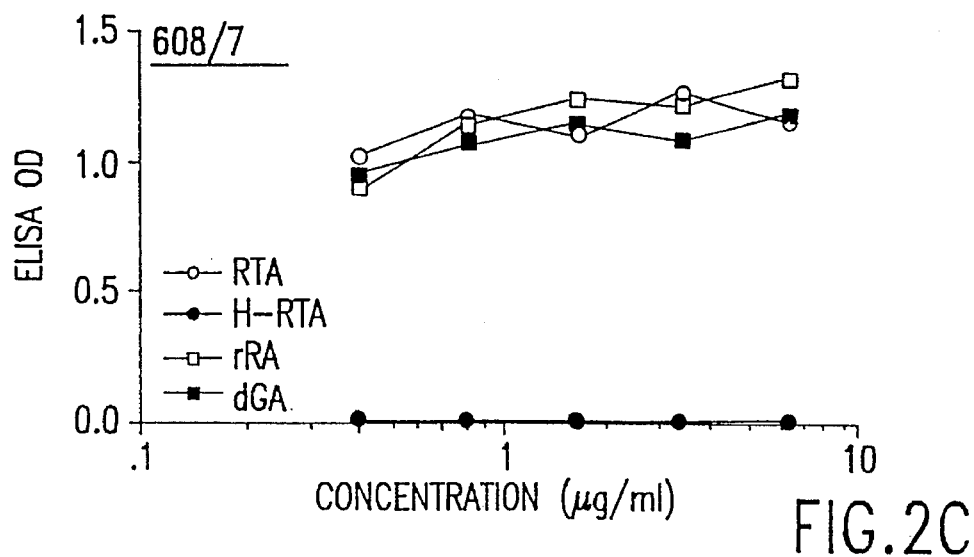
Figure 3A:
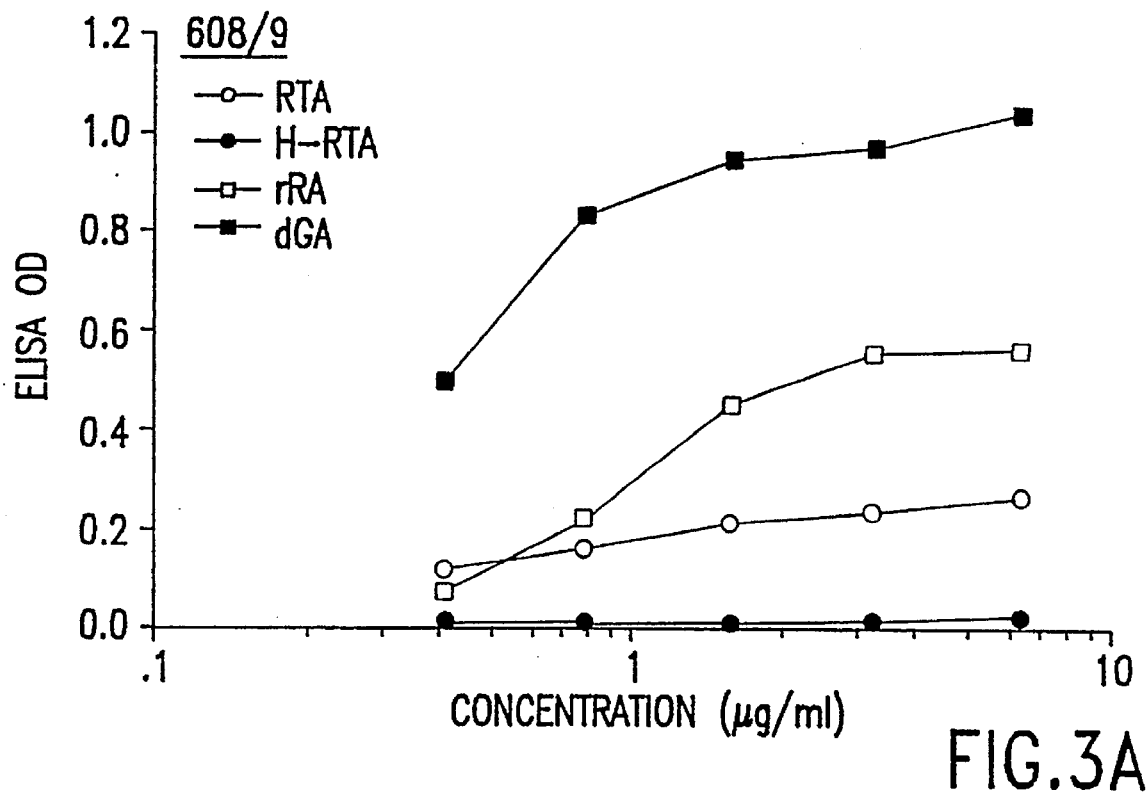
Figure 3B:
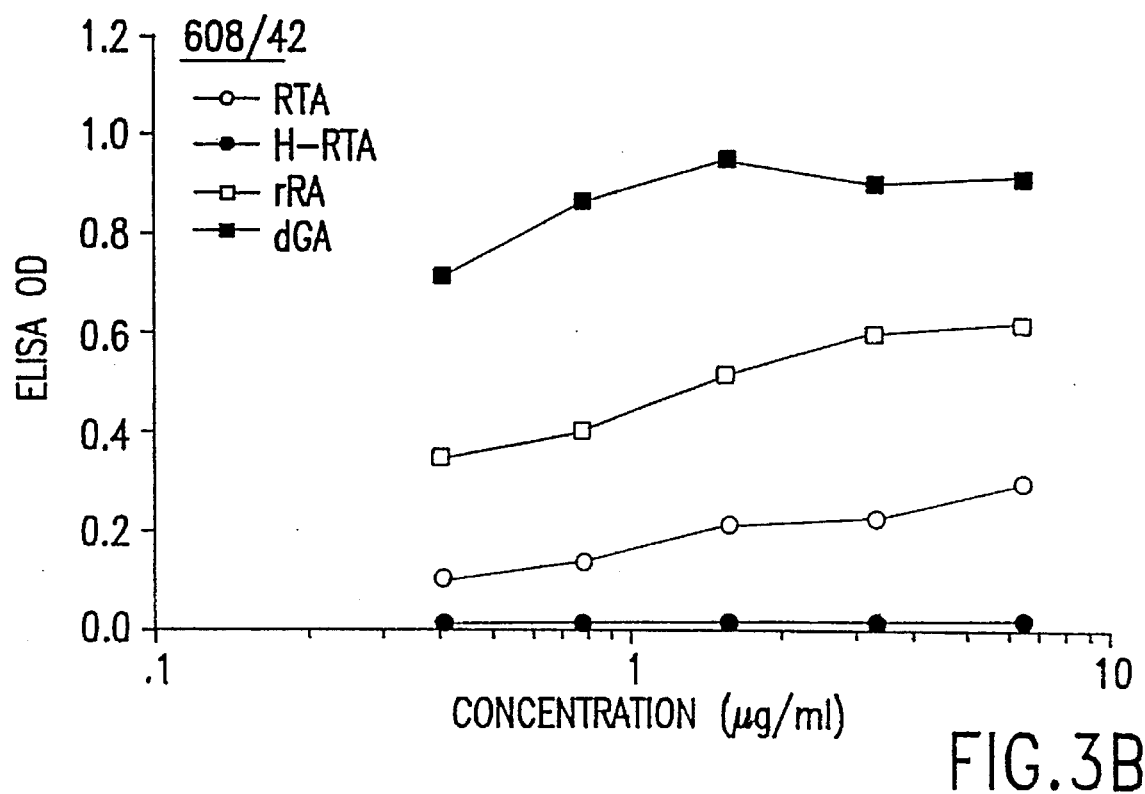

Monoclonal antibodies were generated against RTA using splenocytes from BALB/c mice immunized with the immunotoxin 791T/36, fused with the myeloma cell line P3NS1, and cloned and characterized as previously described. Five Mabs were selected for further study. Three (596/134; 596/192; and 608/7) reacted equally well with native RTA, but not with RTA modified by heating at 56° C., indicating they are directed against peptide epitopes on the molecule but not to oligosaccharide structures on the polypeptide (FIG. 2). RTA is known to carry one or two mannose-containing residues. Of these, monoclonal antibodies, Mab 596/134 and 608/7 had the highest affinity as indicated by their continued high binding at concentrations below 1 µg/ml. Two other Mabs, 608/9 and 608/42, showed weaker binding to the native molecule, but very good binding to deglycosylated RTA, suggesting they recognize a cryptotope which is covered by the sugar residues in the native molecule (FIG. 3).

11.2 Downregulation of IgG with Ab1

Figure 5:
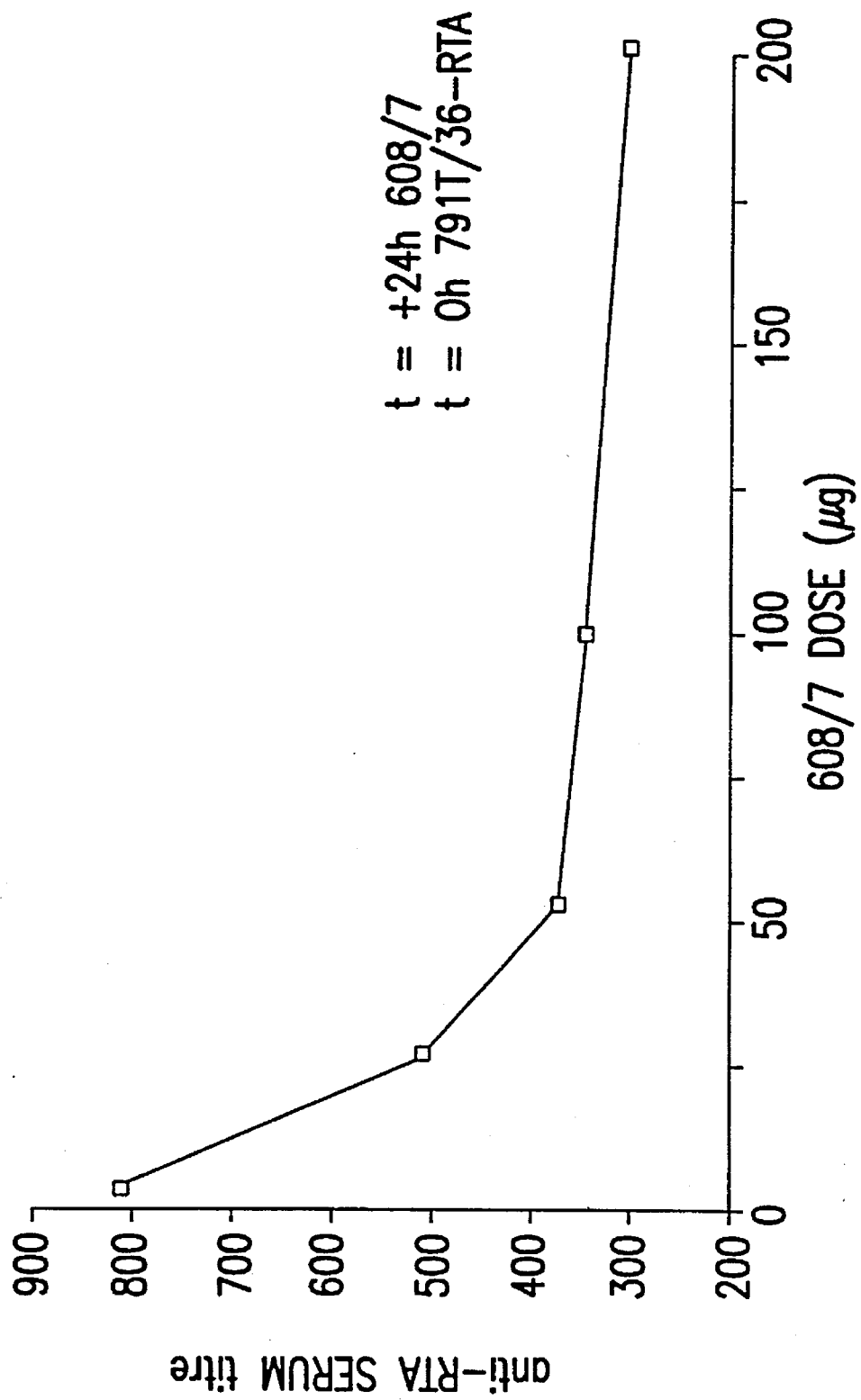
FIG. 5 shows the dose response effect of Mab 608/7, given at doses ranging from 25–200 µg 24 hours after immunization with Immunotoxin.

BALB/c mice were immunized with immunotoxin 791T/36-RTA, and then 24 hours later were treated either with a single injection of 100 µg given intravenously of the anti-RTA Mabs, or with a control Mab, Mab 365, directed against Carcinoembryonic antigen, which does not cross react with RTA. Animals were bled 14 days after initial antigen injection and the IgG anti-RTA serum titers were measured by ELISA, and suppression was compared with that of the control animals treated with the anti-CEA antibody. Three of the five Mabs, 608/7, 596/134 and 596/192 significantly suppressed the anti-RTA response (FIG. 4). The effect was most pronounced with Mabs 608/7 and 596/134, producing 71 and 73% inhibition respectively. Titration of the response with Mab 608/7 (FIG. 5) demonstrated that a single dose of antibody (25–50 µg) resulted in 40–60% reduction in anti-RTA antibody titer.

Figure 6:
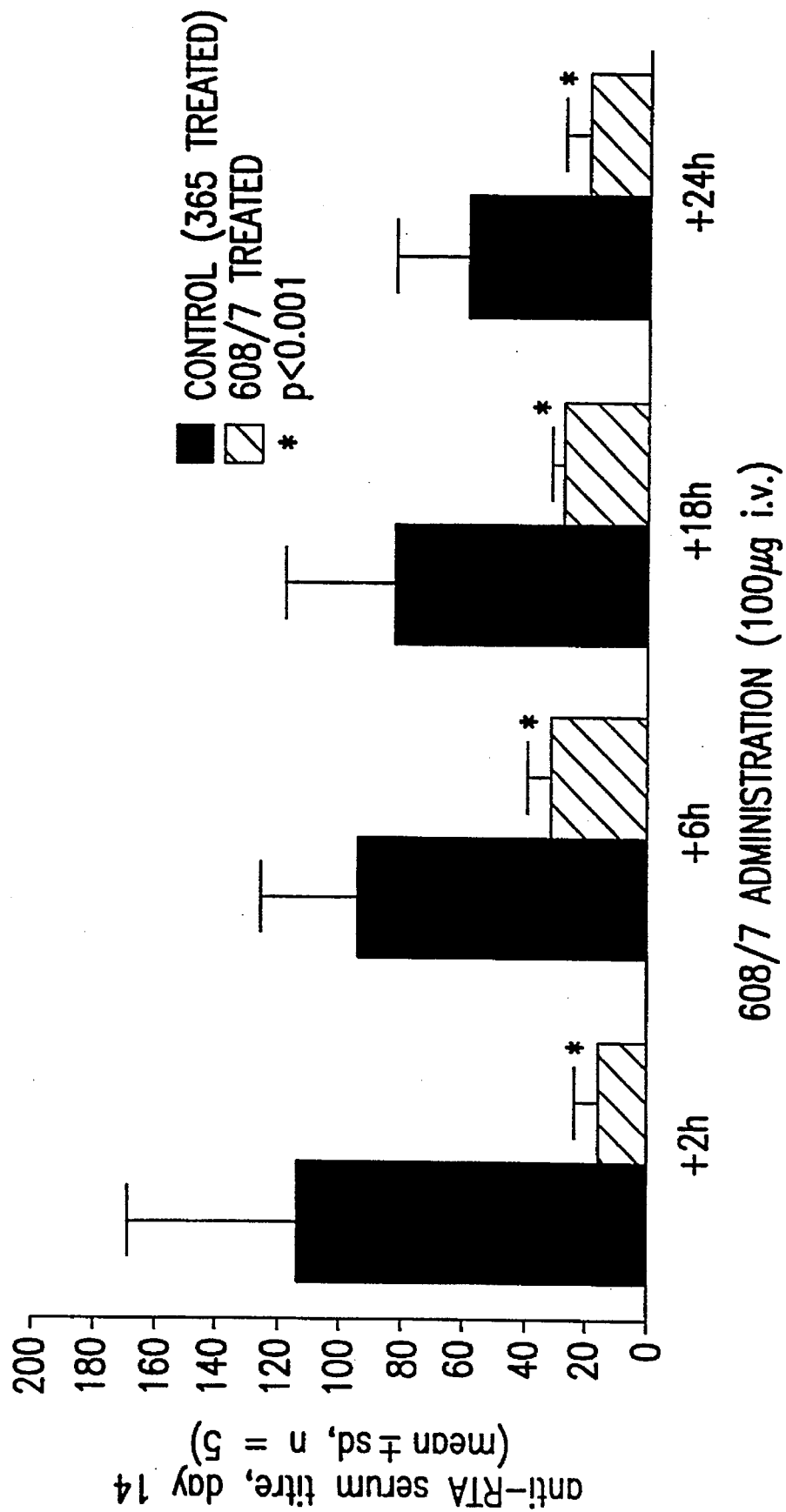
FIG. 6 shows the effect of injection of 100 µg of Mab 608/7 given intravenously at times from 2 to 24 hours after immunization.
Figure 7:
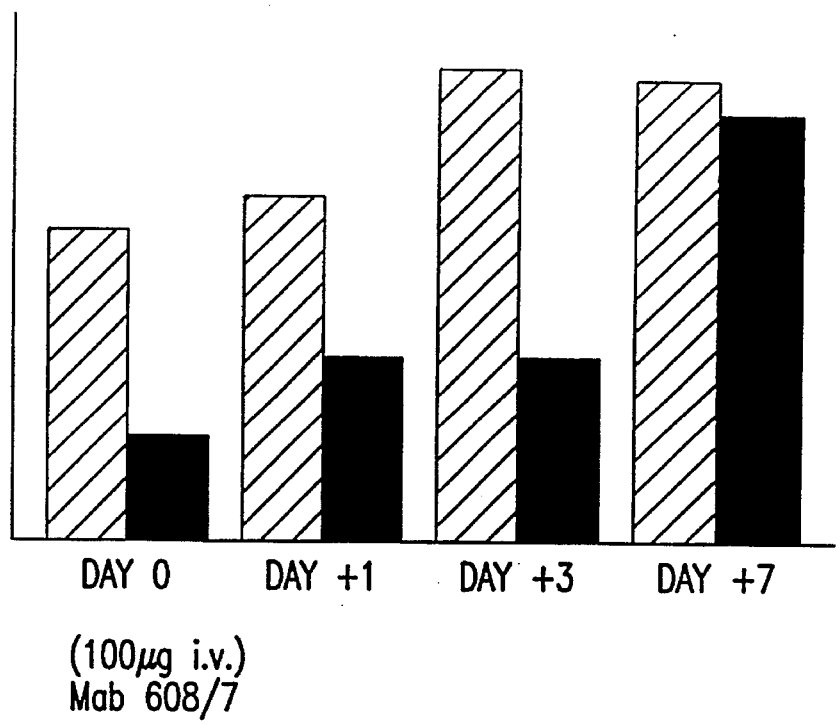
FIG. 7 shows the effect of treatment with 100 µg of Mab 608/7 upon the anti-RTA IgG response of BALB/c mice immunized with immunotoxin, and treated with either Mab 608/7 (solid bars) or an equivalent amount of irrelevant Mab 365 (anti-CEA).
Figure 8:
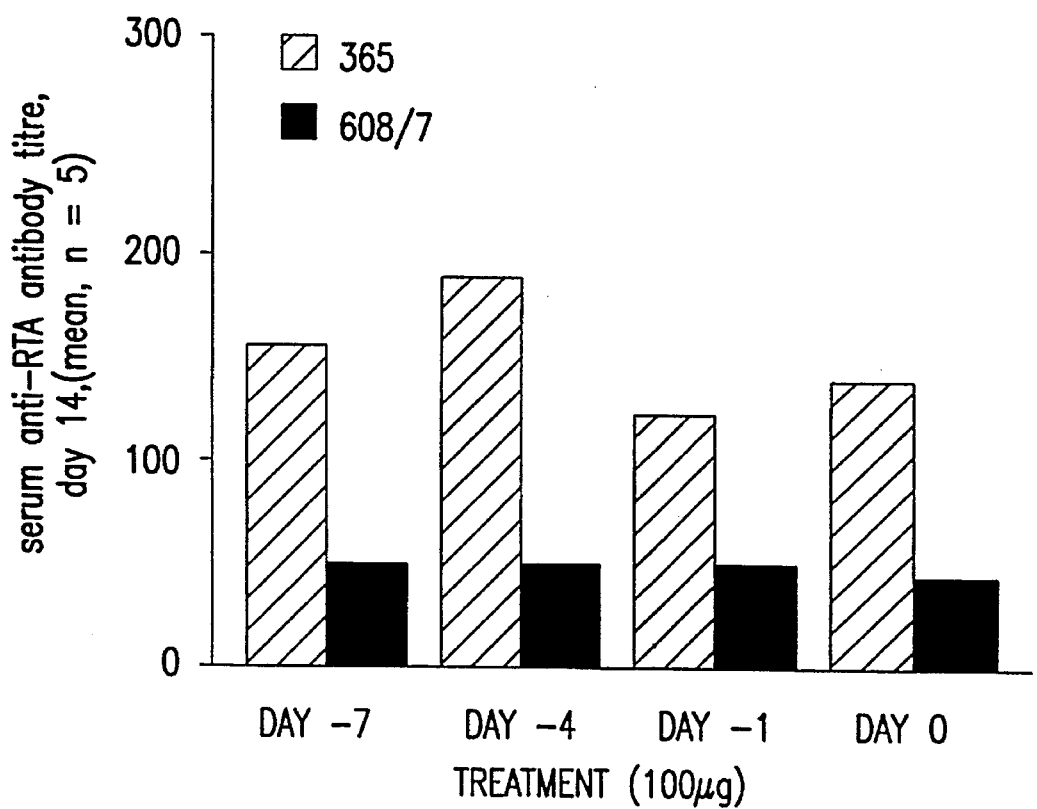
FIG. 8 shows the effect of pretreatment with Mab 608/7 (anti-RTA) or 365 (anti-CEA) given from day −7 to 0 prior to immunization with immunotoxin.
Figure 9:
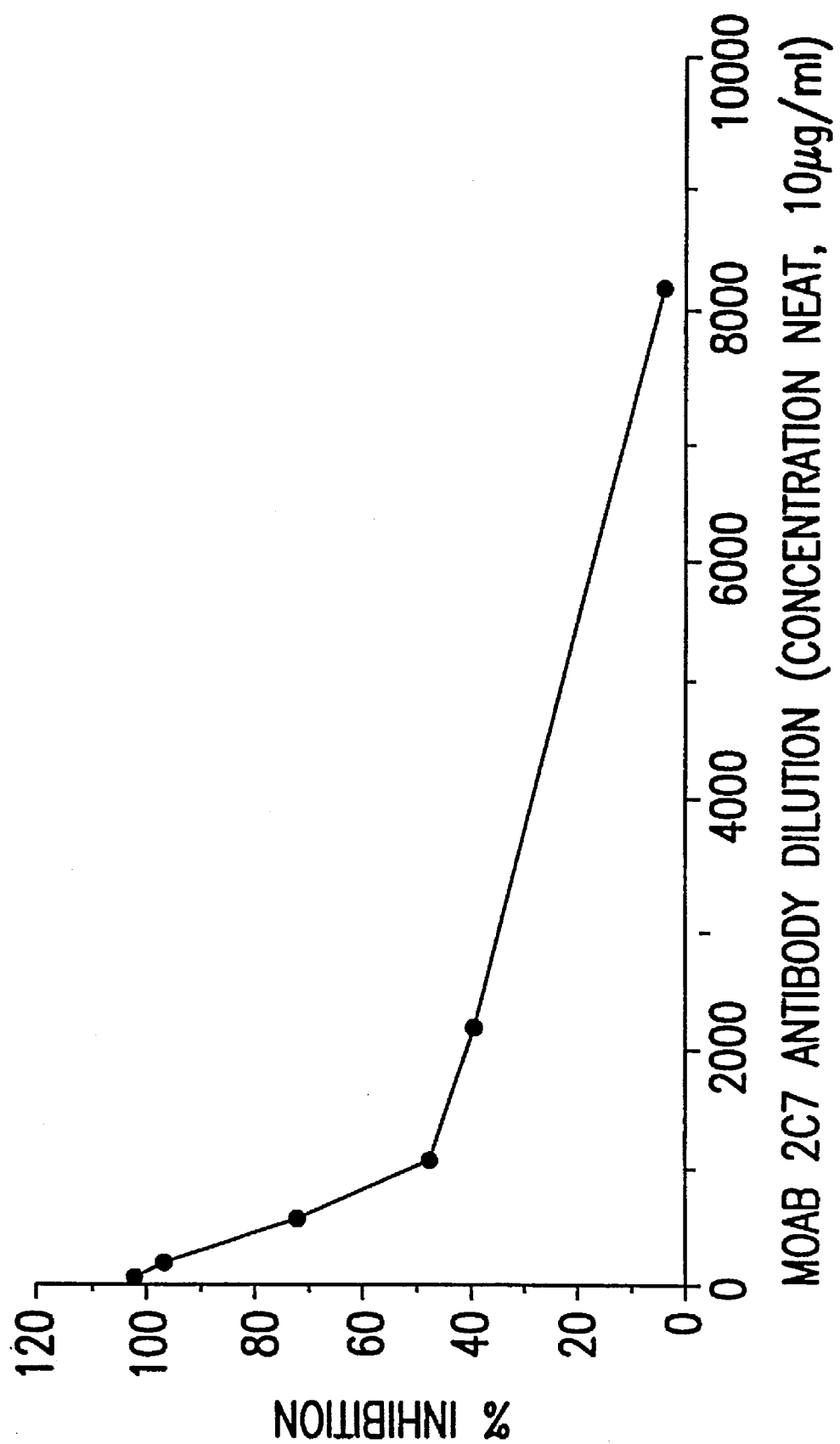
FIG. 9 is a graph showing in vitro inhibition of binding of anti-Der pI monoclonal antibody 4C1 to Der p I by monoclonal antibody 2C7.

Treatment with anti-RTA Mab 608/7 between 2 and 24 hours following immunotoxin treatment produced significant inhibition (p less than 0.001) of anti-RTA antibody production (FIG. 6). In other experiments (FIG. 7), Mab 608/7 was effective up to three days after immunization. In other experiments, (FIG. 8), Mab 608/7 was also effective when administered up to 7 days before immunotoxin treatment, and produced very effective inhibition of anti-RTA responses.

Immunotoxins are rapidly removed from the circulation, with a T ½ of about 20 minutes. This short half life is due to the mannose residues on the RTA, which bind to receptors on the Kuppfer cells of the liver. Since antibody is still capable of down-regulating the IgG anti-RTA response when given as late as 3 days after antigen exposure, it cannot simply be preventing the antigen from reaching the antigen processing cells, since none remains in the circulation. The evidence therefore is that the Mab is inducing tolerance by an effect on antigen processing.

12. Deposit Information

The following hybridomas were deposited with the European Collection of Animal Cell Cultures (ECACC), Vaccine Research and Production Laboratory, Public Health Laboratory Service, Centre for Applied Microbiology and Research, Porton Down, Salisbury, Wiltshire, SP4 0JG, United Kingdom, on Sep. 16, 1993:

| Hybridoma | ECACC No. |
| --- | --- |
| 1. Anti-Der p I | 1122/2C7/B3/A1G (Mab 2C7) 93091612 |
| 2. Anti-Der p I | 1102/H11/A10/E7 (Mab H11) 93091613 |
| 3. Anti-Der p I | 1148/1B12/D6/2A12 (Mab 1B12) 93091615 |
| 4. Anti-Der p II | 1154/2H5/1A10/1E7 (Mab 2H5) 93091614 |

All specific examples and procedures described herein are provided to exemplify the invention, and not for limitation.

All publications and patent applications mentioned herein are hereby incorporated by reference to the same extent as if each were specifically incorporated by reference individually.

What is claimed is:

1. A method for selective suppression of an immune response to dust mite, comprising vaccinating an animal that is sensitized to dust mite Der p I allergen with an effective amount of monoclonal antibody H11, or a monoclonal antibody that recognizes the same epitope as monoclonal antibody H11, to suppress an IgE mediated immune response to dust mite in said animal.

2. A method for selective suppression of an immune response to dust mite, comprising vaccinating an animal that is sensitized to dust mite Der p I allergen with an effective amount of monoclonal antibody H11, or a monoclonal antibody that recognizes the same epitope as monoclonal antibody H11, together with a pharmaceutically acceptable adjuvant to suppress an IgE mediated immune response to dust mite in said animal.

3. The method of claim 1 or 2, wherein vaccinating an animal that is sensitized to dust mite Der p I allergen with an effective amount of the monoclonal antibody stimulates in said animal an anti-idiotype antibody having specificity similar to an anti-idiotype antibody induced in a human hyposensitized to Der p I allergen.

4. The method of claim 1 or 2, wherein the animal is a human.

5. The method of claim 3, wherein the animal is a human.

6. A method for selective suppression of an immune response to dust mite, comprising vaccinating an animal that is sensitized to dust mite Der p I allergen with an effective amount or monoclonal antibody 2C7, or a monoclonal antibody that recognizes the same epitope as monoclonal antibody 2C7, to suppress an IgE mediated immune response to dust mite in said animal.

7. A method for selective suppression of an immune response to dust mite, comprising vaccinating an animal that is sensitized to dust mite Der p I allergen with an effective amount of monoclonal antibody 2C7, or a monoclonal antibody that recognizes the same epitope as monoclonal antibody 2C7, together with a pharmaceutically acceptable adjuvant to suppress an IgE mediated immune response to dust mite in said animal.

8. The method of claim 6 or 7, wherein vaccinating an animal that is sensitized to dust mite Der p I allergen with an effective amount of the monoclonal antibody stimulates in said animal an anti-idiotype antibody having specificity similar to an anti-idiotype antibody induced in a human hyposensitized to Der p I allergen.

9. The method of claim 6 or 7, wherein the animal is a human.

10. The method of claim 8, wherein the animal is a human.

* * * * *